United States Patent
Bruhn et al.

(10) Patent No.: US 11,020,451 B2
(45) Date of Patent: Jun. 1, 2021

(54) METHODS FOR TREATING FIBROTIC CANCERS

(71) Applicant: Promedior, Inc., Lexington, MA (US)

(72) Inventors: Suzanne Bruhn, Bedford, MA (US); Elizabeth Trehu, Duxbury, MA (US); Mark Lupher, Jr., Meridian, ID (US)

(73) Assignee: PROMEDIOR, INC., Lexington, MA (US)

( * ) Notice: Subject to any disclaimer, the term of this patent is extended or adjusted under 35 U.S.C. 154(b) by 0 days.

(21) Appl. No.: 15/027,759

(22) PCT Filed: Oct. 8, 2014

(86) PCT No.: PCT/US2014/059699
§ 371 (c)(1),
(2) Date: Apr. 7, 2016

(87) PCT Pub. No.: WO2015/054390
PCT Pub. Date: Apr. 16, 2015

(65) Prior Publication Data
US 2016/0235812 A1  Aug. 18, 2016

Related U.S. Application Data

(60) Provisional application No. 62/004,828, filed on May 29, 2014, provisional application No. 62/004,836, filed on May 29, 2014, provisional application No. 61/992,807, filed on May 13, 2014, provisional application No. 61/888,269, filed on Oct. 8, 2013.

(51) Int. Cl.
*A61K 38/17* (2006.01)
*A61K 31/519* (2006.01)
*A61K 45/06* (2006.01)

(52) U.S. Cl.
CPC ........ *A61K 38/1716* (2013.01); *A61K 31/519* (2013.01); *A61K 38/1709* (2013.01); *A61K 45/06* (2013.01)

(58) Field of Classification Search
CPC ............ A61K 38/1709; A61K 38/1716; A61K 31/519; A61P 35/00; A61P 35/02
See application file for complete search history.

(56) References Cited

U.S. PATENT DOCUMENTS

| | | | |
|---|---|---|---|
| 8,247,370 B2 | 8/2012 | Pelura | |
| 8,329,659 B2 | 12/2012 | Willett | |
| 8,497,243 B2 | 7/2013 | Hesson et al. | |
| 9,233,140 B2 | 1/2016 | Murray | |
| 9,296,800 B2 | 3/2016 | Willett et al. | |
| 9,556,246 B2 | 1/2017 | Willett | |
| 9,884,899 B2 | 2/2018 | Lupher et al. | |
| 10,702,583 B2 | 7/2020 | Murray | |
| 2007/0065866 A1 | 3/2007 | Gomer et al. | |
| 2008/0044429 A1* | 2/2008 | Johnson | C07K 16/283 424/172.1 |
| 2009/0074754 A1* | 3/2009 | Hesson | A61K 31/7088 424/131.1 |
| 2009/0074771 A1 | 3/2009 | Koenig et al. | |
| 2009/0202520 A1* | 8/2009 | Lupher, Jr. | C07K 14/4737 514/1.1 |
| 2010/0266643 A1 | 10/2010 | Willett et al. | |
| 2010/0317596 A1* | 12/2010 | Willett | C07K 14/47 514/20.9 |
| 2014/0302024 A1 | 10/2014 | Lupher, Jr. et al. | |
| 2018/0318303 A1 | 11/2018 | Trehu et al. | |

FOREIGN PATENT DOCUMENTS

| WO | WO 2008/070117 A1 | 6/2008 |
|---|---|---|
| WO | WO 2010/104961 A1 | 9/2010 |
| WO | WO 2010/141918 A1 | 12/2010 |
| WO | WO 2015/054390 A1 | 4/2015 |

OTHER PUBLICATIONS

Bejanyan et al (Cancer, 2012, vol. 118, pp. 3968-3976).*
Quintas-Cardama et al (Nature Reviews Drug Discovery, 2011, vol. 10, pp. 127-140).*
Thiele et al (Hematologica, 2005, vol. 90, pp. 1128-1132).*
Kontzias et al, Current Opinion in Pharmacology, 2012, vol. 12, pp. 464-470 (Year: 2012).*
Vainchenker et al (Blood, 2011, vol. 118, pp. 1723-1735) (Year: 2011).*
Verstovsek, et al., "Phase 2 Trial of PRM-151, an Anti-Fibrotic Agent, in Patients with Myelofibrosis: Stage 1 Results," *Blood Journal*, 124(21): 6 pages, (Jan. 1, 2014).
Anonymous, "Promedior Pipeline," Retrieved from the Internet: http://web.archive.org/web/20130811080632/http://www.promedior.com/pipeline/pipeline.html. 2 pages, [retrieved on Mar. 7, 2017].
Ganetsky, "Ruxolitinib: A New Treatment Option for Myelofibrosis," *The Journal of Human Pharmacology and Drug Therapy*, 33(1):84-92, (Jan. 1, 2013).
Duffield, et al., "PRM-151 (Recombinant Human Serum Amyloid P/Pentraxin 2) for the Treatment of Fibrosis," *Drug News and Perspectives*, 23(5):305-315, (Jan. 1, 2010).
Mascarenhas, "Rationale for Combination Therapy in Myelofibrosis," *Best Practice & Research Clinical Haematology*, 27:197-208, (2014).
Extended European Search Report for EP 14851638, dated Mar. 24, 2017.
International Search Report from PCT/US2014/059699, dated Nov. 26, 2014.

(Continued)

*Primary Examiner* — Karen A. Canella
(74) *Attorney, Agent, or Firm* — Haley Guiliano LLP; Karen Mangasarian; Brian M. Gummow

(57) ABSTRACT

In part, the disclosure relates to methods of treating fibrotic cancers by administering one or more Serum Amyloid Protein (SAP) agonists. In certain aspects, the method further comprises the conjoint administration of an anti-cancer therapeutic, e.g., a chemotherapeutic agent. In certain aspects, the disclosure relates to methods of treating myelofibrosis by administering an SAP agonist and optionally one or more anti-cancer therapeutic agents.

45 Claims, 4 Drawing Sheets
Specification includes a Sequence Listing.

(56) References Cited

OTHER PUBLICATIONS

Tefferi, et al., "CALR vs JAK2 VS MPL-Mutated or Tripe-Negative Myelofibrosis: Clinical, Cytogenetic and Molecular Comparisons," Leukemia, 28:1472-1477, (2014).

Vannucchi, et al., "Mutation-Enhanced International Prognostic Scoring System (MIPSS) for Primary Myelofibrosis: An AGIMM & IWG-MRT Project," Blood, 124(21):405, (2014).

Vannucchi, et al., "JAK2 Allele Burden in the Myeloproliferative Neoplasms: Effects on Phenotype, Prognosis and Change with Treatment," Therapeutic Advances in Hematology, 2(1):21-32, (2011).

Verstovsek et al., "Phase 2 trial of PRM-151, an antifibrotic agent, in patients with myelofibrosis: Stage 1 results," Journal of Clinical Oncology 32, No. 15 suppl (May 20, 2014): 7114. (Abstract).

Wilson, Steven E., "Corneal myofibroblast biology and pathobiology: Generation, persistence, and transparency," Experimental Eye Research, 2012, vol. 99, pp. 78-88 (25 pages).

* cited by examiner

SEQUENCE LISTING

<160> NUMBER OF SEQ ID NOS: 4

<210> SEQ ID NO 1
<211> LENGTH: 204
<212> TYPE: PRT
<213> ORGANISM: Homo sapiens

<400> SEQUENCE: 1

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
            20                  25                  30

Phe Thr Leu Cys Phe Arg Ala Tyr Ser Asp Leu Ser Arg Ala Tyr Ser
        35                  40                  45

Leu Phe Ser Tyr Asn Thr Gln Gly Arg Asp Asn Glu Leu Leu Val Tyr
    50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
        195                 200

<210> SEQ ID NO 2
<211> LENGTH: 208
<212> TYPE: PRT
<213> ORGANISM: Gallus gallus

<400> SEQUENCE: 2

Gln Glu Asp Leu Tyr Arg Lys Val Phe Val Phe Arg Glu Asp Pro Ser
1               5                   10                  15

Asp Ala Tyr Val Leu Leu Gln Val Gln Leu Glu Arg Pro Leu Leu Asn
            20                  25                  30

Phe Thr Val Cys Leu Arg Ser Tyr Thr Asp Leu Thr Arg Pro His Ser
        35                  40                  45

Leu Phe Ser Tyr Ala Thr Lys Ala Gln Asp Asn Glu Ile Leu Leu Phe
    50                  55                  60

```
Lys Pro Lys Pro Gly Glu Tyr Arg Phe Tyr Val Gly Lys Tyr Val
 65                  70                  75                  80

Thr Phe Arg Val Pro Glu Asn Arg Gly Glu Trp Glu His Val Cys Ala
                 85                  90                  95

Ser Trp Glu Ser Gly Ser Gly Ile Ala Glu Phe Trp Leu Asn Gly Arg
            100                 105                 110

Pro Trp Pro Arg Lys Gly Leu Gln Lys Gly Tyr Glu Val Gly Asn Glu
            115                 120                 125

Ala Val Val Met Leu Gly Gln Glu Gln Asp Ala Tyr Gly Gly Gly Phe
            130                 135                 140

Asp Val Tyr Asn Ser Phe Thr Gly Glu Met Ala Asp Val His Leu Trp
145                 150                 155                 160

Asp Ala Gly Leu Ser Pro Asp Lys Met Arg Ser Ala Tyr Leu Ala Leu
                165                 170                 175

Arg Leu Pro Pro Ala Pro Leu Ala Trp Gly Arg Leu Arg Tyr Glu Ala
            180                 185                 190

Lys Gly Asp Val Val Lys Pro Arg Leu Arg Glu Ala Leu Gly Ala
            195                 200                 205

<210> SEQ ID NO 3
<211> LENGTH: 205
<212> TYPE: PRT
<213> ORGANISM: Bos taurus

<400> SEQUENCE: 3

Gln Thr Asp Leu Arg Gly Lys Val Phe Val Phe Pro Arg Glu Ser Ser
  1               5                  10                  15

Thr Asp His Val Thr Leu Ile Thr Lys Leu Glu Lys Pro Leu Lys Asn
                 20                  25                  30

Leu Thr Leu Cys Leu Arg Ala Tyr Ser Asp Leu Ser Arg Gly Tyr Ser
             35                  40                  45

Leu Phe Ser Tyr Asn Ile His Ser Lys Asp Asn Glu Leu Leu Val Phe
 50                  55                  60

Lys Asn Gly Ile Gly Glu Tyr Ser Leu Tyr Ile Gly Lys Thr Lys Val
 65                  70                  75                  80

Thr Val Arg Ala Thr Glu Lys Phe Pro Ser Pro Val His Ile Cys Thr
                 85                  90                  95

Ser Trp Glu Ser Ser Thr Gly Ile Ala Glu Phe Trp Ile Asn Gly Lys
            100                 105                 110

Pro Leu Val Lys Arg Gly Leu Lys Gln Gly Tyr Ala Val Gly Ala His
            115                 120                 125

Pro Lys Ile Val Leu Gly Gln Glu Gln Asp Ser Tyr Gly Gly Gly Phe
            130                 135                 140

Asp Lys Asn Gln Ser Phe Met Gly Glu Ile Gly Asp Leu Tyr Met Trp
145                 150                 155                 160

Asp Ser Val Leu Ser Pro Glu Glu Ile Leu Leu Val Tyr Gln Gly Ser
                165                 170                 175

Ser Ser Ile Ser Pro Thr Ile Leu Asp Trp Gln Ala Leu Lys Tyr Glu
            180                 185                 190

Ile Lys Gly Tyr Val Ile Val Lys Pro Met Val Trp Gly
            195                 200                 205

<210> SEQ ID NO 4
<211> LENGTH: 204
<212> TYPE: PRT
```

```
<213> ORGANISM: Cricetulus migratorius

<400> SEQUENCE: 4

Gln Thr Asp Leu Thr Gly Lys Val Phe Val Phe Pro Arg Glu Ser Glu
1               5                   10                  15

Ser Asp Tyr Val Lys Leu Ile Pro Arg Leu Glu Lys Pro Leu Glu Asn
            20                  25                  30

Phe Thr Leu Cys Phe Arg Thr Tyr Thr Asp Leu Ser Arg Pro His Ser
        35                  40                  45

Leu Phe Ser Tyr Asn Thr Lys Asn Lys Asp Asn Glu Leu Leu Ile Tyr
    50                  55                  60

Lys Glu Arg Met Gly Glu Tyr Gly Leu Tyr Ile Glu Asn Val Gly Ala
65                  70                  75                  80

Ile Val Arg Gly Val Glu Glu Phe Ala Ser Pro Val His Phe Cys Thr
                85                  90                  95

Ser Trp Glu Ser Ser Ser Gly Ile Ala Asp Phe Trp Val Asn Gly Ile
            100                 105                 110

Pro Trp Val Lys Lys Gly Leu Lys Lys Gly Tyr Thr Val Lys Thr Gln
        115                 120                 125

Pro Ser Ile Ile Leu Gly Gln Glu Gln Asp Asn Tyr Gly Gly Gly Phe
    130                 135                 140

Asp Lys Ser Gln Ser Phe Val Gly Glu Met Gly Asp Leu Asn Met Trp
145                 150                 155                 160

Asp Ser Val Leu Thr Pro Glu Glu Ile Lys Ser Val Tyr Glu Gly Ser
                165                 170                 175

Trp Leu Glu Pro Asn Ile Leu Asp Trp Arg Ala Leu Asn Tyr Glu Met
            180                 185                 190

Ser Gly Tyr Ala Val Ile Arg Pro Arg Val Trp His
        195                 200
```

METHODS FOR TREATING FIBROTIC CANCERS

CROSS REFERENCE TO RELATED APPLICATIONS

This application is a United States National Stage under 35 U.S.C. § 371 of International Application No. PCT/US2014/059699, filed Oct. 8, 2014, which claims priority to and the benefit of U.S. provisional patent application Ser. Nos. 61/888,269 filed on Oct. 8, 2013, 61/992,807 filed on May 13, 2014, 62/004,828 filed on May 29, 2014, and 62/004,836 filed on May 29, 2014, the disclosures of which are incorporated herein by reference in their entirety

SEQUENCE LISTING

The instant application contains a Sequence Listing which has been submitted electronically in ASCII format and is hereby incorporated by reference in its entirety. Said ASCII copy, created on Apr. 7, 2016, is named 104112-0033-301-SL.txt and is 7,651 bytes in size.

BACKGROUND OF THE INVENTION

Certain cancers and proliferative conditions are characterized by the growth of dense connective tissue within and around a neoplasm, replacing normal tissue. Such fibrotic cancers are difficult to treat because chemotherapeutic agents often cannot penetrate the dense fibrotic stroma surrounding the cancer cells. In other cancers, such as myelofibrosis, replacement of healthy organ tissue by fibrosis results in inadequate organ function, which contributes to the symptoms of the cancer. Despite aggressive treatment regimens, resistance of fibrotic cancers to chemotherapeutic agents has resulted in poor clinical outcome. Therefore, a need remains for developing novel therapeutic strategies for the treatment of fibrotic cancers.

SUMMARY OF THE INVENTION

In certain aspects, the disclosure provides a method for treating a fibrotic cancer or improving the efficacy of an anti-cancer therapeutic in a patient, comprising administering to a patient in need thereof a therapeutically effective amount of a serum amyloid P (SAP) agonist.

In certain aspects, the disclosure provides a method for treating a fibrotic cancer or improving the efficacy of an anti-cancer therapeutic in a patient, the method comprising administering to said patient in need thereof a therapeutically effective amount of one or more SAP agonists in combination with one or more additional active agents.

In some embodiments, the SAP agonist is selected from an anti-FcγRI antibody, an anti-FcγRII antibody, an anti-FcγRIII antibody, a cross-linked anti-FcγR antibody, an aggregated IgG antibody, or a cross-linked IgG antibody.

In some embodiments, the SAP agonist is selected from a small molecule, nucleic acid, or polypeptide.

In some embodiments, the SAP agonist is an SAP polypeptide, such as a glycosylated human SAP polypeptide. By way of example, the SAP agonist may comprise an SAP polypeptide, such as a glycosylated human SAP polypeptide, such as a glycosylated human SAP polypeptide having glycosylation that differs from SAP isolated from human serum (e.g., human SAP comprising an N-linked oligosaccharide chain, wherein at least one branch of the oligosaccharide chain terminates with a α2,3-linked sialic acid moiety). In certain embodiments, the SAP agonist is recombinant human SAP (e.g., rhSAP). In certain embodiments, the SAP agonist comprises the recombinant human SAP also known in the art as PRM-151. Duffield (2010) Drug News & Perspectives, 23(5): 305-315. Optionally, rhSAP may be prepared in CHO cells or in another suitable cell line. Any of the methods described herein comprise, in certain embodiments, administering the recombinant human SAP known as PRM-151.

In some embodiments, the SAP agonist is a glycosylated human SAP polypeptide comprising an N-linked oligosaccharide chain, wherein at least one branch of the oligosaccharide chain terminates with a α2,3-linked sialic acid moiety. In some embodiments, all the sialylated branches of the oligosaccharide chain terminate with α2,3-linked sialic acid moieties. In some embodiments, the oligosaccharide chain is substantially free of α2,6-linked sialic acid moieties. By way of example, the SAP agonist may comprise such a glycosylated human SAP polypeptide. In some embodiments, the glycosylated human SAP comprises recombinant human SAP also referred to as recombinant human pentraxin-2 (hPTX-2), as described in Duffield and Lupher, Drug News & Perspectives 2010, 23(5):305-315.

In some embodiments, the SAP polypeptide comprises an amino acid sequence at least 85% identical to SEQ ID NO: 1. In some embodiments, the SAP polypeptide comprises an amino acid sequence at least 95% identical to SEQ ID NO: 1. In some embodiments, the SAP polypeptide is a glycosylated SAP polypeptide having glycosylation that differs from human SAP purified from serum. In some embodiments, the SAP polypeptide comprises five polypeptide chains each of which comprise an amino acid sequence at least 85% (at least 90%, 95%, 98%, or event 100%) identical to SEQ ID NO: 1.

In some embodiments, the SAP polypeptide is a fusion protein comprising an SAP domain and one or more heterologous domains. In some embodiments, the one or more heterologous domains enhance one or more of in vivo stability, in vivo half-life, uptake/administration, tissue localization or distribution, formation of protein complexes, and/or purification.

In some embodiments, the SAP polypeptide comprises one or more modified amino acid residues. In some embodiments, the one or more modified amino acid residues comprise a PEGylated amino acid, a prenylated amino acid, an acetylated amino acid, a biotinylated amino acid, and/or an amino acid conjugated to an organic derivatizing agent.

In some embodiments, the SAP agonist is administered by a mode selected from: topically, by injection, by intravenous injection, by subcutaneous injection, by inhalation, continuous release by depot or pump, or a combination thereof.

In some embodiments, the method further comprises administering to the patient an anti-cancer therapeutic (e.g., an additional anti-cancer therapeutic).

In some embodiments, the anti-cancer therapeutic is selected from: chemotherapy agents, antibody-based agents, tyrosine kinase inhibitors, immunomodulatory agents, biologic agents, and combinations thereof. A single additional agent or multiple additional agents or treatment modalities may be co-administered (at the same or differing time points and/or via the same or differing routes of administration and/or on the same or a differing dosing schedule). In certain embodiments, treatment with the SAP agonist improves the safety and/or efficacy and/or reduces one or more side effects of the additional anti-cancer therapeutic, relative to that experienced when the additional anti-cancer therapeutic is administered in the absence of the SAP agonist. In certain embodiments, prior to addition of the SAP agonist, a patient (the patient in need of treatment) is unresponsive or resistant or refractory to, or the patient is receiving a suboptimal or declining benefit from treatment with the anti-cancer therapeutic, and addition of an SAP agonist to the therapeutic regimen results in increased clinical benefit due to the SAP agonist and/or improves responsiveness of the additional anti-cancer therapeutic. In certain embodiments, treatment with the SAP agonist is such that the additional anti-cancer therapeutic can be administered at a different dose than that recommended when the additional anti-cancer therapeutic is administered alone, for example, the anti-cancer therapeutic can be (or is) administered at a lower dose or at a higher dose. This difference in dose can be assessed relative to a specific patient's regimen or relative to the recommended dose or dose range. In certain embodiments, the SAP agonist comprises an SAP polypeptide, such as a glycosylated SAP polypeptide, such as a glycosylated SAP polypeptide having glycosylation that differs from human SAP purified from serum. In certain embodiments, the combination of an SAP agonist and the additional anti-cancer therapeutic is indicated for a condition, patient population or sub-population for which the additional anti-cancer therapeutic alone is not indicated.

In some embodiments, the chemotherapy agent is selected from but not limited to: actinomycin D, aldesleukin, alitretinoin, all-trans retinoic acid/ATRA, altretamine, amascrine, asparaginase, azacitidine, azathioprine, bacillus calmette-guerin/BCG, bendamustine hydrochloride, bexarotene, bicalutamide, bleomycin, bortezomib, busulfan, capecitabine, carboplatin, carfilzomib, carmustine, chlorambucil, cisplatin/cisplatinum, cladribine, cyclophosphamide/cytophosphane, cytabarine, dacarbazine, daunorubicin/daunomycin, denileukin diftitox, dexrazoxane, docetaxel, doxorubicin, epirubicin, etoposide, fludarabine, fluorouracil (5-FU), gemcitabine, goserelin, hydrocortisone, hydroxyurea, idarubicin, ifosfamide, interferon alfa, irinotecan CPT-11, lapatinib, lenalidomide, leuprolide, mechlorethamine/chlormethine/mustine/HN2, mercaptopurine, methotrexate, methylprednisolone, mitomycin, mitotane, mitoxantrone, octreotide, oprelvekin, oxaliplatin, paclitaxel, pamidronate, pegaspargase, pegfilgrastim, PEG interferon, pemetrexed, pentostatin, phenylalanine mustard, plicamycin/mithramycin, prednisone, prednisolone, procarbazine, raloxifene, romiplostim, sargramostim, streptozocin, tamoxifen, temozolomide, temsirolimus, teniposide, thalidomide, thioguanine, thiophosphoamide/thiotepa, thiotepa, topotecan hydrochloride, toremifene, tretinoin, valrubicin, vinblastine, vincristine, vindesine, vinorelbine, vorinostat, zoledronic acid, and combinations thereof. In certain embodiments, the method comprises administration of the SAP agonist and an additional anti-cancer therapeutic, which additional anti-cancer therapeutic is a chemotherapeutic agent, such as a single chemotherapeutic agent or a combination of two or more chemotherapeutic agents. In certain embodiments, the SAP agonist comprises an SAP polypeptide, such as a glycosylated SAP polypeptide, such as a SAP polypeptide having glycosylation that differs from human SAP purified from serum. In certain embodiments, the patient in need of treatment is a patient having a cancer that is refractory, unresponsive, or sub-optimally responsive to chemotherapy alone, and the method improves efficacy and/or responsiveness to chemotherapy. In certain embodiments, the patient in need of treatment is a patient who had previously experienced therapeutic benefit from the chemotherapy alone, but for whom the therapeutic benefit of treatment with chemotherapy alone has plateaued or substantially plateaued, or for whom such treatment is no longer effective or is decreasing in effectiveness. In certain embodiments, the patient in need thereof is a patient having pancreatic cancer.

In some embodiments, the antibody-based agent is selected from but not limited to: alemtuzumab, bevacizumab, cetuximab, fresolimumab, gemtuzumab ozogamicin, ibritumomab tiuxetan, ipilimumab, ofatumumab, panitumumab, rituximab, tositumomab, trastuzumab, trastuzumab DM1, and combinations thereof. In certain embodiments, the method comprises administration of the SAP agonist and an additional anti-cancer therapeutic, which additional anti-cancer therapeutic is an antibody-based agent. In certain embodiments, the SAP agonist comprises an SAP polypeptide, such as a glycosylated SAP polypeptide, such as a SAP polypeptide having glycosylation that differs from human SAP purified from serum. In certain embodiments, the patient in need of treatment is a patient having a cancer that is refractory, unresponsive, or sub-optimally responsive to the particular antibody-based agent alone, and the method improves efficacy and/or responsiveness to that agent. In certain embodiments, the patient in need of treatment is a patient who had previously experienced therapeutic benefit from the antibody-based agent alone, but for whom the therapeutic benefit of treatment with the antibody-based agent alone has plateaued or substantially plateaued, or for whom such treatment is no longer effective or is decreasing in effectiveness. In certain embodiments, the combination is indicated for treating patients for whom the antibody-based agent alone is not indicated.

In some embodiments, the tyrosine kinase inhibitor is selected from but not limited to: axitinib, bafetinib, bosutinib, cediranib, crizotinib, dasatinib, erlotinib, gefitinib, imatinib, lapatinib, neratinib, nilotinib, pazopanib, ponatinib, quizartinib, regorafenib, sorafenib, sunitinib, vandetanib, vatalanib, and combinations thereof. In certain embodiments, the method comprises administration of the SAP agonist and an additional anti-cancer therapeutic, which additional anti-cancer therapeutic is a tyrosine kinase inhibitor. In certain embodiments, the SAP agonist comprises an SAP polypeptide, such as a glycosylated SAP polypeptide, such as a SAP polypeptide having glycosylation that differs from human SAP purified from serum. In certain embodiments, the patient in need of treatment is a patient having a cancer that is refractory, unresponsive, or sub-optimally responsive to the particular tyrosine kinase inhibitor, and the method improves efficacy and/or responsiveness to that agent. In certain embodiments, the patient in need of treatment is a patient who had previously experienced therapeutic benefit from the tyrosine kinase inhibitor alone, but for whom the therapeutic benefit of treatment with the tyrosine kinase inhibitor alone has plateaued or substantially plateaued, or for whom such treatment is no longer effective or is decreasing in effectiveness. In certain embodiments, the combination is indicated for treating patients for whom the tyrosine kinase inhibitor alone is not indicated.

In some embodiments, the immunomodulatory agent is selected from but not limited to: thalidomide, lenalidomide, pomalidomide, methotrexate, leflunomide, cyclophosphamide, cyclosporine A, minocycline, azathioprine, tacrolimus, methylprednisolone, mycophenolate mofetil, rapamycin, mizoribine, deoxyspergualin, brequinar, 5,6-dimethylxanthenone-4-acetic acid (DMXAA), lactoferrin, poly AU, polyI:polyC12U, poly-ICLC, imiquimod, resiquimod, unmethylated CpG dinucleotide (CpG-ODN), and ipilumumab. In certain embodiments, the method comprises administration of the SAP agonist and an additional anti-cancer therapeutic, which additional anti-cancer therapeutic is an immunomodulatory agent. In certain embodiments, the SAP agonist comprises an SAP polypeptide, such as a glycosylated SAP polypeptide, such as a SAP polypeptide having glycosylation that differs from human SAP purified from serum. In certain embodiments, the SAP agonist comprises an SAP polypeptide, such as a glycosylated SAP polypeptide, such as a SAP polypeptide having glycosylation that differs from human SAP purified from serum. In certain embodiments, the patient in need of treatment is a patient having a cancer that is refractory, unresponsive, or sub-optimally responsive to the particular tyrosine kinase inhibitor, and the method improves efficacy and/or responsiveness to that agent. In certain embodiments, the patient in need of treatment is a patient who had previously experienced therapeutic benefit from the immunomodulatory agent alone, but for whom the therapeutic benefit of treatment with the immunomodulatory agent alone has plateaued or substantially plateaued, or for whom such treatment is no longer effective or is decreasing in effectiveness. In certain embodiments, the combination is indicated for treating patients for whom the immunomodulatory agent alone is not indicated.

In some embodiments, the tyrosine kinase inhibitor is a Janus kinase inhibitor selected from but not limited to: AC-430, AZD1480, baricitinib, BMS-911453, CEP-33779, CYT387, GLPG-0634, INCB18424, lestaurtinib, LY2784544, NS-018, pacritinib, ruxolitinib, TG101348 (SAR302503), tofacitinib, VX-509, R-348, R723 and combinations thereof. In certain embodiments, the method comprises administration of the SAP agonist and an additional anti-cancer therapeutic, which additional anti-cancer therapeutic is a Janus kinase inhibitor. In certain embodiments, the SAP agonist comprises an SAP polypeptide, such as a glycosylated SAP polypeptide, such as a SAP polypeptide having glycosylation that differs from human SAP purified from serum. In certain embodiments, the Janus kinase inhibitor is ruxolitinib. In certain embodiments, the SAP agonist comprises an SAP polypeptide and the Janus kinase inhibitor comprises ruxolitinib. In certain embodiments, the patient in need of treatment is a patient having a cancer that is refractory, unresponsive, or sub-optimally responsive to the particular Janus kinase inhibitor, and the method improves efficacy and/or responsiveness to that agent. In certain embodiments, the patient in need of treatment is a patient who had previously experienced therapeutic benefit from the Janus kinase inhibitor alone, but for whom the therapeutic benefit of treatment with the Janus kinase inhibitor alone has plateaued or substantially plateaued, or for whom such treatment is no longer effective or is decreasing in effectiveness. In certain embodiments, the combination is indicated for treating patients for whom the Janus kinase inhibitor alone is not indicated. In certain embodiments, the cancer is myelofibrosis.

In some embodiments, the biologic agent is selected from but not limited to: IL-2, IL-3, erythropoietin, G-CSF, filgrastim, interferon alfa, bortezomib and combinations thereof.

In some embodiments, the anti-cancer therapeutic is selected from but not limited to: AB0024, AZD1480, AT-9283, BMS-911543, CYT387, everolimus, givinostat, imetelstat, lestaurtinib, LY2784544, NS-018, oral arsenic, pacritinib, panobinostat, peginterferon alfa-2a, pomalidomide, pracinostat, ruxolitinib, TAK-901, and TG101438 (SAR302503).

In some embodiments, the anti-cancer therapeutic is ruxolitinib.

In certain embodiments, the patient in need of treatment is naïve and has not been previously treated with another anti-cancer therapeutic prior to initiation of treatment with a SAP agonist. Once therapy is initiated it is, in certain embodiments, monotherapy with an SAP agonist and in other embodiments a combination therapy with one or more additional anti-cancer therapeutics.

In some embodiments, the SAP agonist and the one or more additional active agents (e.g., the additional anti-cancer therapeutic) are co-formulated. In some embodiments, the SAP agonist and the one or more additional active agents are administered simultaneously. In some embodiments, the SAP agonist and the one or more additional active agents are administered within a time of each other to produce overlapping therapeutic effects in the patient. When the SAP agonist and the one or more additional active agents are administered simultaneously or within a time of each other to produce overlapping therapeutic effects, the agents may be administered by the same or a different route of administration (e.g., oral versus infusion).

In some embodiments, the cancer is selected from but not limited to myelofibrosis, gastric cancer, pancreatic cancer, Hodgkin's lymphoma, non-Hodgkin's lymphoma, hairy cell leukemia, multiple myeloma, medulloblastoma, myeloid leukemia, and acute lymphocytic leukemia.

In some embodiments, the cancer is myelofibrosis. In some embodiments, the myelofibrosis is primary myelofibrosis, post-polycythemia vera myelofibrosis, or post-essential thrombocythemia myelofibrosis.

In some embodiments, the cancer is pancreatic cancer.

In certain embodiments, treatment of any of the foregoing or following (e.g., any of the foregoing or following cancers) is with SAP monotherapy, such as described herein. In other embodiments, treatment of any of the foregoing or following (e.g., any of the foregoing or following cancers) is with a combination therapy comprising an SAP agonist and an additional anti-cancer agent, such as described herein. In certain embodiments, the subject in need of treatment is treatment naïve, and treatment with an SAP agonist, such as an SAP agonist comprising an SAP polypeptide, either alone or in combination with an additional anti-cancer agent, is the first anti-cancer therapy received. In other embodiments, the subject in need of treatment has had one or more prior treatments with a non-SAP therapy or therapies. In certain embodiments, the subject has had one or more previous non-SAP therapies and has either (i) failed to respond, or (ii) initially responded but is no longer responding, or (iii) after initially responding is now having decreasing responsiveness. Regardless of whether the subject has ceased responding to an additional anti-cancer agent, in certain embodiments, the disclosure contemplates continued administration of that anti-cancer agent in combination with an SAP agonist, such as an SAP agonist as described herein.

In certain embodiments, the method comprises treating a fibrotic cancer, such as treating any one of the cancers described herein, without inducing or resulting in treatment-related myelosuppression. In other words, in certain embodiments, methods of the present disclosure do not induce or result in worsening of myelosuppression in comparison to, for example, that observed prior to initiation of treatment. Myelosuppression may be assessed according to the Common Terminology for Coding of Adverse Events (CTCAE) on a scale of Grade 0-Grade 5 (See National Cancer Institute Common Terminology Criteria for Adverse Events v4.0, NCI, NIH, DHHS. May 29, 2009 NIH publication #09-7473). In some embodiments, one or more measures of myelosuppression, such as anemia, do not deteriorate (e.g., from a Grade 3 to Grade 4 adverse event; from a Grade 2 to Grade 3 adverse event) as a result of treatment.

In certain embodiments, treatment with an SAP agonist of the disclosure has a safety profile that supports use as a monotherapy or a combination therapy.

In certain embodiments, treatment comprises administering the SAP agonist according to a dosing schedule, such as any of the dosing schedules described herein. In certain embodiments, administration and/or the therapeutically effective amount is understood in the art to comprise administration according to a dose and dosing schedule effective to produce therapeutic benefit as defined in a clinical study protocol, full prescribing information, the Investigator's Brochure, or by improvement in measures generally understood by experts in the field to be of benefit to patients with the respective disease. In certain embodiments, the SAP agonist, whether administered alone or as part of a combination therapy, can be administered according to a dosing schedule providing administration less than once per week. In certain embodiments, such less frequent dosing occurs following an initial loading phase wherein, for example, during the first week of a treatment cycle, the SAP agonist is administered multiple times.

In certain embodiments, treatment improves organ function (e.g., therapeutic efficacy comprises improvement in organ function; SAP agonist is administered alone or in combination and improves organ function). In certain embodiments, the organ is the bone marrow and improvement in organ function is evaluated by assessing improvement in hemoglobin and/or platelets (e.g., improvement in one or both of these metrics evinces improvement in organ function; in the case of platelets, improvement in platelets refers to increasing platelets in subjects suffering from low platelet levels; in the case of hemoglobin, improvement in hemoglobin refers to increasing hemoglobin in subjects suffering from low hemoglobin levels). In certain embodiments, treatment restores normal tissue, such as by decreasing fibrosis (e.g., therapeutic efficacy comprises restoration of normal tissue). In certain embodiments, restoring normal tissue is evaluated by assessing bone marrow fibrosis.

The disclosure contemplates all suitable combinations of any of the features of the invention, such as combinations of any of the aspects and embodiments described herein. For example, the disclosure contemplates that any of the foregoing aspects and embodiments may be combined with each other and/or with any of the embodiments disclosed herein. For example, SAP agonists described using any combination of functional and/or structural features may be used alone or in a combination therapy in any of the methods described herein, to treat any of the conditions, patient populations, or sub-populations of patients described herein.

DETAILED DESCRIPTION OF THE INVENTION

Overview

Figure 1:
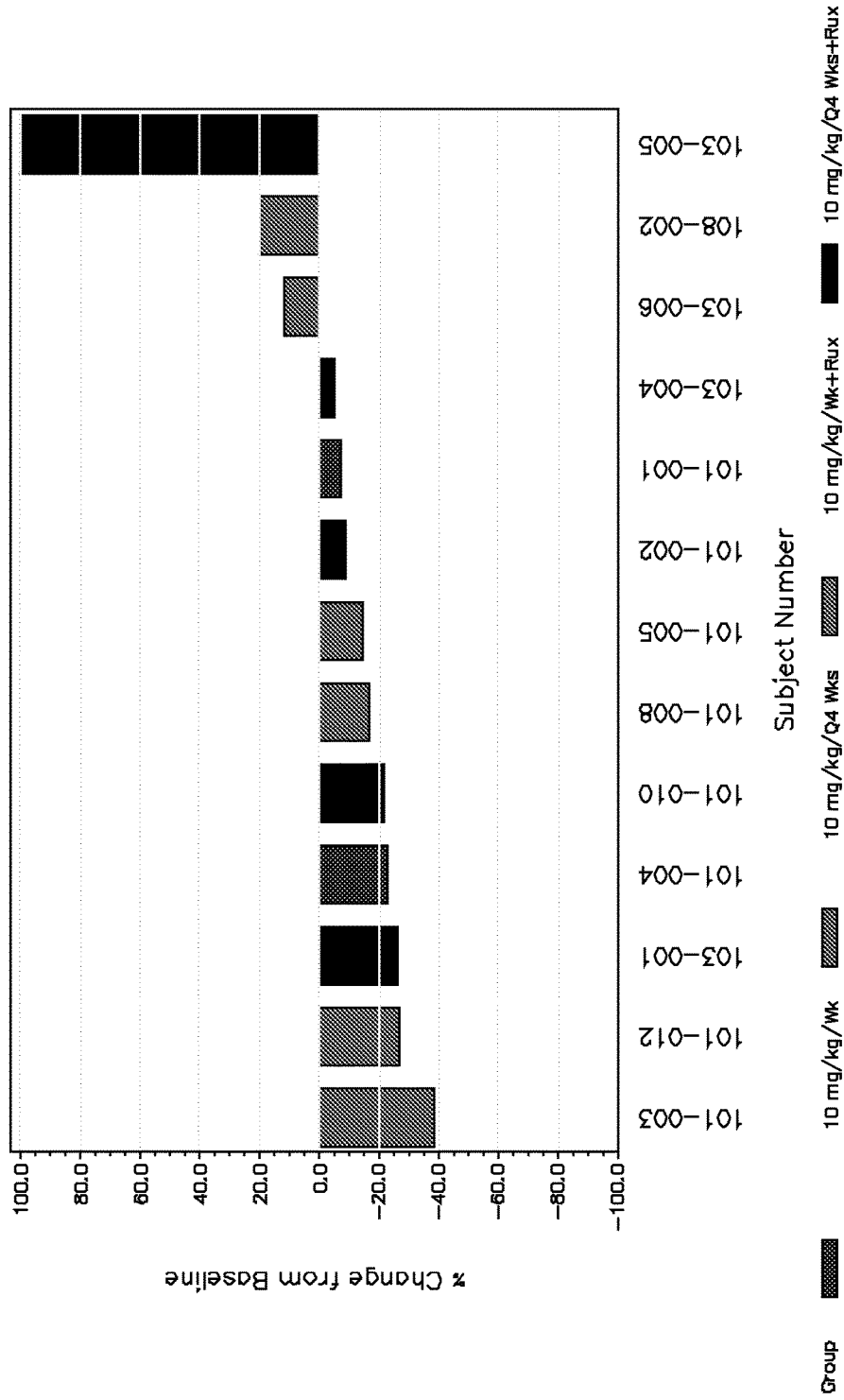
FIG. 1 is a waterfall plot depicting the percentage change in spleen size in subjects with palpable spleen who were followed to C6D29 (Cycle 6, Day 29) or end of study. The Y-axis indicates the percentage change in spleen size from baseline. The evaluated subjects are shown on the X-axis. As is evident from FIG. 1, decrease in spleen size from baseline, even over this time period, was observed in at least one patient from each treatment group (e.g., mono- and combination therapy on two different dosing schedules).

The present invention provides new therapeutic regimens for treating fibrotic cancers and cancer-associated fibrosis using an SAP polypeptide or SAP agonist, as a single agent, or in combination with an anti-cancer therapeutic.

The present invention is based on the discovery that an SAP polypeptide or SAP agonist may effectively treat some fibrotic cancers as a single agent, and that a combination of strategies may be warranted to treat some fibrotic cancers. A variety of cancers and proliferative conditions are characterized by the presence of dense fibrotic tissue. The present invention is based on the discovery that a combination of strategies may be warranted to treat fibrotic cancers and cancer-associated fibrosis. One goal of therapeutic intervention is to prevent or reduce excess accumulation of fibrotic tissue, in order to allow the anti-cancer therapeutics access to the cancer cells. Another goal of therapeutic intervention is to restore normal organ function by preventing or reducing excess fibrotic tissue.

The regulation of events leading to fibrosis involves at least two major events. One is the proliferation and differentiation of fibrocytes. Fibrocytes are a distinct population of fibroblast-like cells derived from peripheral blood monocytes that normally enter sites of tissue injury to promote angiogenesis and wound healing. Fibrocytes are important in the formation of tumors, particularly stromal tissue in tumors. Fibrocytes differentiate from CD14+ peripheral blood monocytes, and may differentiate from other PBMC cells. The presence of SAP, IL-12, Laminin-1, anti-FcγR antibodies, crosslinked IgG and/or aggregated IgG may inhibit or at least partially delay this process.

The second major event is the formation and maintenance of fibrotic tissue. Fibrotic tissue may be formed and maintained by the differentiation of monocytes into fibrocytes, fibroblasts, macrophages or myofibroblasts, the recruitment and proliferation of fibroblast cells, the formation of new extracellular matrix, and the growth of new vascular tissue. In pathologic fibrosis, such as following chronic inflammation, injury, malignancy, or idiopathic fibrosis, it is this excess fibrotic tissue that can lead to tissue damage and destruction.

Recently, it has been suggested that serum amyloid P (SAP) or pentraxin-2 (PTX-2) can be used as a therapeutic agent to treat various disorders, including fibrosis-related disorders, hypersensitivity disorders, autoimmune disorders, mucositis, and inflammatory disorders such as those caused by microbial infection. See, for example, U.S. Pat. Nos. 8,247,370 and 8,497,243 and U.S. patent application Ser. Nos. 12/720,845 and 12/720,847. SAP binding to FcγR provides an inhibitory signal for fibrocyte, fibrocyte precursor, myofibroblast precursor, and/or hematopoietic monocyte precursor differentiation. The use of SAP and SAP agonists as a therapeutic treatment for fibrosis is described in U.S. Pat. Nos. 7,763,256, and 8,247,370, which are hereby incorporated by reference. In certain embodiments of any of the methods described herein, the method comprises administration of SAP, such as SAP comprising an SAP polypeptide (see the Examples). In certain embodiments, the SAP is recombinant human SAP, also referred to as recombinant human pentraxin-2, such as recombinant human SAP produced in CHO cells. In certain embodiments, the SAP polypeptide comprises a human SAP polypeptide, such as a human SAP polypeptide having glycosylation that differs from that of SAP purified from human serum.

The present invention provides methods for treating fibrotic cancers or cancer-associated fibrosis. The method generally involves administering an effective amount of an anti-fibrotic agent such as an SAP polypeptide or SAP agonist, as a single agent, or in combination with an effective amount of an anti-cancer therapeutic. The SAP polypeptide or SAP agonist and the anti-cancer therapeutic may be targeted to different cell populations. For example, the SAP polypeptide or SAP agonist can be targeted to cells involved in regulating fibrosis while the anti-cancer therapeutic is targeted to cancer cells. In selected embodiments, these components may be formulated or administered as a combined composition, or may be separately and/or independently administered, e.g., systemically or to the target location(s). The methods include methods for treating cancer-associated fibrosis or fibrotic cancers (e.g., fibrotic cancers such as myelofibrosis, cancers of the breast, uterus, pancreas or colon, including fibroids, fibroma, fibroadenomas and fibrosarcomas).

In some embodiments, an effective amount of an SAP polypeptide or SAP agonist is an amount that, when administered alone, or in combination therapy, is effective to reduce fibrosis by at least about 10%, and more preferably at least about 15%, 20%, 25%, 30%, 35%, 40%, 45%, or even at least about 50%, or more, compared with the degree of fibrosis in the individual prior to treatment with the SAP polypeptide or SAP agonist. In certain embodiments, the SAP polypeptide or SAP agonist is SAP comprising an SAP polypeptide, and is administered according to a dosing schedule, and when administered alone or in a combination therapy, is effective to reduce fibrosis by at least about 10%, and more preferably at least about 15%, 20%, 25%, 30%, 35%, 40%, 45%, or even at least about 50%, or more, compared with the degree of fibrosis in the individual prior to treatment with SAP.

In other embodiments, the present invention provides methods that involve administering a synergistic combination of an SAP polypeptide or SAP agonist and an anti-cancer therapeutic. As used herein, a "synergistic combination" of an SAP polypeptide or SAP agonist and anti-cancer therapeutic is a combined dosage that is more effective in the therapeutic or prophylactic treatment than the incremental improvement in treatment outcome that could be predicted or expected from a merely additive combination of (i) the therapeutic or prophylactic benefit of an SAP polypeptide or SAP agonist when administered at that same dosage as a monotherapy and (ii) the therapeutic or prophylactic benefit of the anti-cancer agent when administered at the same dosage as a monotherapy.

It is shown here that administering an SAP polypeptide or SAP agonist, in one example the SAP agonist comprises a glycosylated SAP polypeptide (e.g., SAP comprising a glycosylated SAP polypeptide, such as a glycosylated SAP polypeptide having glycosylation that differs from that of SAP purified from human serum; recombinant human SAP, such as recombinant human pentraxin-2 or PRM-151), resulted in the amelioration of fibrotic cancer (e.g. myelofibrosis) symptoms, physical findings, and blood count abnormalities including anemia, thrombocytopenia, thrombocytosis, and leukocytosis relative to baseline levels at the start of therapy. It is also shown that administering a combination of an SAP polypeptide or SAP agonist, such as an SAP agonist comprising a glycosylated SAP polypeptide (e.g., SAP comprising a glycosylated SAP polypeptide, such as a glycosylated SAP polypeptide having glycosylation that differs from that of SAP purified from human serum; recombinant human SAP, such as recombinant human pentraxin-2 or PRM-151), and an anti-cancer therapeutic (e.g. a Jak kinase inhibitor, such as ruxolitinib) resulted in amelioration of fibrotic cancer (e.g. myelofibrosis) symptoms, splenomegaly, and blood count abnormalities including anemia, thrombocytopenia, thrombocytosis, and leukocytosis, relative to baseline levels. The methods of the disclosure are also based on the finding that an SAP polypeptide or SAP agonist of the disclosure was well tolerated both alone and in combination with another anti-cancer therapeutic, with no evidence of clinically significant myelosuppression induced by or related to SAP treatment (e.g., with no evidence of treatment related myelosuppression). In fact, in certain embodiments, improvements in measures indicative of myelosuppression, such as anemia, were achieved following treatment. Not only was the combination therapy efficacious, but it may be suitable for patients for whom the benefits of the additional anti-cancer therapeutic alone had begun to wane. In addition, the combination therapy also resulted in improvement in some of the side effects often experienced in patients treated with the anti-cancer therapeutic alone. In this case, for patients who were being treated with ruxolitinib (a Janus kinase inhibitor) alone prior to addition of SAP to their therapeutic regimen, we observed improvements in anemia and thrombocytopenia, as assessed by increased hemoglobin levels and platelet counts, relative to those side effects experienced in those patients prior to addition of SAP (e.g., relative to treatment with Janus kinase inhibitor alone). These results not only demonstrate efficacy of SAP as a monotherapy or as a combination therapy for a fibrotic cancer, but also the use of SAP to expand the therapeutic window and patient population for other therapeutics, to provide treatment modalities for patients and subpopulations of patients for whom available treatments failed or are inadequate, and to improve the safety profile of available therapies while itself having therapeutic efficacy. Moreover, it is shown here that administering an SAP polypeptide or SAP agonist, such as SAP comprising a glycosylated SAP polypeptide, as a single agent or as part of a combination therapy, resulted in a decrease in organ fibrosis, leading to restoration of organ function and improvement in fibrotic cancer symptoms. The ability of SAP to precisely target the fundamental fibrotic pathology validates its broad potential to treat and reverse fibrosis in a wide range of fibrotic cancers.

Definitions

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and nucleic acid chemistry and hybridization are those well known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, N.Y.), which are provided throughout this document.

The articles "a" and "an" are used herein to refer to one or to more than one (i.e., to at least one) of the grammatical object of the article. By way of example, "an element" means one element or more than one element.

As used herein, the term "about" means plus or minus 10% of the numerical value of the number with which it is being used. Therefore, about 50% means in the range of 45%-55%.

As used herein, the term "substantially" means being largely but not wholly what is specified. For example, the term "substantially similar" with regard to a nucleotide sequence indicates that the sequence is largely identical to another reported sequence for the same protein or peptide; however, the nucleotide sequence may include any number of variations or mutations that do not affect the structure or function of the resulting protein.

"Administering" when used in conjunction with a therapeutic means to administer a therapeutic directly into or onto a target tissue or to administer a therapeutic to a patient, whereby the therapeutic positively impacts the tissue to which it is targeted. Thus, as used herein, the term "administering," when used in conjunction with an SAP polypeptide or SAP agonist can include, but is not limited to, providing an SAP polypeptide or SAP agonist to a subject systemically by, for example, intravenous injection (e.g., which may be intravenous infusion), whereby the therapeutic reaches the target tissue. "Administering" a composition may be accomplished by, for example, intravenous, subcutaneous, intramuscular, or intralesional injection, oral administration, topical administration, or by these methods in combination with other known techniques. Such combination techniques include heating, radiation, ultrasound and the use of delivery agents. When more than one different therapeutic agent is administered, the agents may be administered by the same or different routes of administration and/or at the same or differing times. As is understood in the art, an agent can be administered according to a dosing schedule.

"Providing," when used in conjunction with a therapeutic, means to administer a therapeutic directly into or onto a target tissue, or to administer a therapeutic to a patient whereby the therapeutic positively impacts the tissue to which it is targeted.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

As used herein, "isolated" means altered or removed from the natural state through human intervention. For example, SAP naturally present in a living animal is not "isolated," but a synthetic SAP polypeptide, or an SAP polypeptide partially or completely separated from the coexisting materials of its natural state is "isolated." An isolated SAP polypeptide can exist in substantially purified form, or can exist in a non-native environment such as, for example, a cell into which the SAP polypeptide has been delivered.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

As used herein, the term "nucleic acid" refers to a polynucleotide such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotide.

"Optional" or "optionally" means that the subsequently described event or circumstance may or may not occur, and that the description includes instances where the event occurs and instances where it does not.

The terms "peptides", "proteins" and "polypeptides" are used interchangeably herein. The term "purified protein" refers to a preparation of a protein or proteins that are preferably isolated from, or otherwise substantially free of, other proteins normally associated with the protein(s) in a cell or cell lysate. The term "substantially free of other cellular proteins" or "substantially free of other contaminating proteins" is defined as encompassing individual preparations of each of the proteins comprising less than 20% (by dry weight) contaminating protein, and preferably comprises less than 5% contaminating protein. Functional forms of each of the proteins can be prepared as purified preparations by using a cloned gene as is well known in the art. By "purified", it is meant that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

By "pharmaceutically acceptable," "physiologically tolerable," and grammatical variations thereof, as they refer to compositions, carriers, diluents, and reagents or other ingredients of the formulation, can be used interchangeably and indicate that the materials are capable of administration without the production of undesirable physiological effects such as nausea, dizziness, rash, gastric upset or other deleterious effects to the recipient thereof.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable and formed with inorganic acids, such as hydrochloric acid, hydrobromic acid, sulfuric acid, nitric acid, carbonic acid, phosphoric acid, and the like. Organic acids may be selected from aliphatic, cycloaliphatic, aromatic, araliphatic, heterocyclic, carboxylic, and sulfonic classes of organic acids, such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid, and the like.

As used herein, the term "pharmaceutically acceptable salts, esters, amides, and prodrugs" refers to those carboxylate salts, amino acid addition salts, esters, amides, and prodrugs of the compounds which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

As used herein, the term "therapeutic" means an agent utilized to treat, combat, ameliorate, prevent or improve an unwanted condition or disease of a patient. In part, embodiments of the present invention are directed to the treatment of cancer, myeloproliferative diseases, or the aberrant proliferation of cells.

A "therapeutically effective amount" or "effective amount" of a composition is a predetermined amount calculated to achieve the desired result. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. A therapeutically effective amount of compound of this invention is typically an amount such that when it is administered in a physiologically tolerable excipient composition, it is sufficient. Therapeutically effective amounts may be administered according to a dosing schedule.

"N-linked" oligosaccharides are those oligosaccharides that are linked to a peptide backbone through asparagine, by way of an asparagine-N-acetylglucosamine linkage. N-linked oligosaccharides are also called "N-glycans." Naturally occurring N-linked oligosaccharides have a common pentasaccharide core of Man[($\alpha$1,6-)-(Man($\alpha$1,3)]-Man($\beta$1,4)-GlcNAc($\beta$1,4)-GlcNAc($\beta$1,N). They differ in the presence of, and in the number of branches (also called antennae) of peripheral sugars such as N-acetylglucosamine, galactose, N-acetylgalactosamine, fucose, and sialic acid. Optionally, this structure may also contain a core fucose molecule and/or a xylose molecule.

The term "sialic acid" refers to any member of a family of nine-carbon carboxylated sugars. The most common member of the sialic acid family is N-acetyl-neuraminic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261: 11550-11557; Kanamori et al., J. Biol. Chem. 265: 21811-21819 (1990)). Also included are 9-substituted sialic acids such as a 9-O—$C_1C_6$-acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For a review of the sialic acid family, see, e.g., Varki, Glycobiology 2: 25-40 (1992); Sialic Acids: Chemistry, Metabolism and Function, R. Schauer, Ed. (Springer-Verlag, New York (1992)).

A "genetically engineered" or "recombinant" cell is a cell having one or more modifications to the genetic material of the cell. Such modifications include, but are not limited to, insertions of genetic material, deletions of genetic material and insertion of genetic material that is extrachromasomal whether such material is stably maintained or not.

As used herein, the term "modified sugar," refers to a naturally- or non-naturally-occurring carbohydrate that is enzymatically added onto an amino acid or a glycosyl residue of a peptide in a process of the invention. The modified sugar is selected from a number of enzyme substrates including, but not limited to, sugar nucleotides (mono-, di-, and tri-phosphates), activated sugars (e.g., glycosyl halides, glycosyl mesylates) and sugars that are neither activated nor nucleotides. A "modified sugar" may be covalently functionalized with a "modifying group." Useful modifying groups include, but are not limited to, water-soluble and -insoluble polymers, therapeutic moieties, diagnostic moieties, and biomolecules. The locus of functionalization with the modifying group is selected such that it does not prevent the "modified sugar" from being added enzymatically to a peptide or glycosyl residue of the peptide.

SAP Polypeptides and SAP Agonists

One aspect of the disclosure provides SAP polypeptides or SAP agonists useful in the treatment of fibrotic cancers and cancer-associated fibrosis. SAP agonists encompass all compounds and compositions that increase or otherwise mimic endogenous SAP signaling, including compounds that increase SAP activity. Throughout the disclosure, "SAP polypeptides or SAP agonists" or "SAP polypeptides or SAP agonists of the disclosure" are referred to. Unless otherwise specified, such reference contemplates the use of any of the SAP agonists disclosed herein, including use of recombinant SAP, such as pentameric SAP comprising an SAP polypeptide comprising human SAP, which SAP polypeptide has a glycosylation that differs from that of SAP isolated from human serum. The invention contemplates use of any of the SAP polypeptides and SAP agonists disclosed herein in any of the methods described herein, including use alone or as a combination therapy.

SAP

SAP or pentraxin-2 is a naturally occurring serum protein in mammals composed of five identical subunits, or protomers, which are non-covalently associated in a disk-like complex. SAP belongs to the pentraxin superfamily of proteins, which are characterized by this cyclic pentameric structure. The classical short pentraxins include SAP as well as C-reactive protein (Osmand, A. P., et al., Proc. Nat. Acad. Sci., 74: 739-743, 1997). The long pentraxins include pentraxin-3. SAP is normally synthesized in the liver and has a physiological half-life of twenty-four hours. Human SAP (hSAP) circulates at approximately 20-40 µg/ml in plasma as a homopentamer. The sequence of the human SAP subunit is disclosed in SEQ ID NO: 1, which corresponds to amino acids 20-223 of Genbank Accession NO. NP 001630 (signal sequence not depicted).

Previous research demonstrates that SAP has an important role in both the initiation and resolution phases of the immune response. hSAP functions in innate resistance to microbes and in the scavenging and phagocytosis of cellular debris and appears to play a role in regulation of wound healing and fibrosis. These functions may involve (i) binding to ligands associated with microbes and cellular debris, as specified above, and various extracellular matrix proteins in a $Ca^{2+}$-dependent manner, (ii) binding to Clq for complement activation by promoting opsonization by C3b and iC3b, (iii) binding to Fcγ receptors to initiate direct opsonization and subsequent phagocytosis or endocytosis, and (iv) subsequent regulation of monocyte function and differentiation. Accordingly, hSAP molecules localize to sites of injury and repair and may target and/or concentrate in these locations through binding these molecules.

The 3D structure of hSAP has been determined by X-ray crystallography and several crystal structures complexed with different ligands have also been reported. The pentameric structure of hSAP has 5-fold rotational symmetry and is fairly rigid with a pore. The diameter of the hSAP pentamer is approximately 100 Å, and the central pore is 20 Å in diameter and 35 Å deep. Each protomer is constructed of antiparallel β-strands arranged in two sheets, with a hydrophobic core with a jellyroll topology. The hSAP pentamer has 2 faces, an A-face, which possesses five α helices, one on each protomer, and a B face with 5 sets of double calcium-binding sites. The B-face is thought to provide a calcium-dependent ligand binding face, and several calcium-dependent ligands that bind the B-face have been identified, including phosphorylethanolamine, DNA, heparan sulfate, dermatan sulfate and dextran sulfate, laminin and collagen IV. The A-face of hSAP also appears to bind molecules such as Clq and may mediate phagocytosis through binding to Fcγ receptors. Each protomer may be glycosylated at Asn32, a single site.

N- and C-termini are solvent accessible and are located on the inner edge of each protomer molecule. The N-terminus is located on the outer edge of each protomer and on the perimeter of the ring formed by the 5 protomers. The C-terminus is located more toward the inner perimeter and pore of the pentamer ring but is directed outward toward the A face. N- and C-termini within one protomer are about 25 Å apart. The termini do not appear to be involved in subunit interactions and they are away from the glycan chain attached at Asn32. The subunits of hSAP are held together non-covalently with approximately 15% of the surface of each subunit involved in these interactions. These extensive interactions account for the considerable stability of the hSAP pentamer.

The SAP encompassed by embodiments described herein includes SAP from any source such as, for example, human SAP or isomers or analogs from other vertebrate or mammalian sources. SAP further encompasses SAP molecules having modifications from the native PTX-2 amino acid sequence introduced by, for example, site-directed mutagenesis. Such modification may alter specific amino acids and/or other features of the molecule, while retaining the general pentameric pentraxin nature of the molecule. The "SAP" may be used to encompass both SAP pentamers and SAP protomers. "SAP pentamer" or "pentameric SAP" refers to a protein complex at least including five SAP protomers, and "SAP protomer" refers to one individual protein unit of the SAP pentamer. In certain embodiments of any of the aspects and embodiments of the disclosure, the invention comprises administration of an SAP agonist, wherein the SAP agonist comprises an SAP pentamer comprising an SAP polypeptide comprising the amino acid sequence set forth in SEQ ID NO: 1. In certain embodiments, the SAP polypeptide comprises recombinant human SAP. An exemplary recombinant human SAP comprises PRM-151. In certain embodiments, the SAP agonist comprises recombinant SAP. Methods of making proteins generally, and human pentraxin-2 specifically, recombinantly are known in the art. Suitable cells for recombinant expression, such as insect or mammalian cells may be selected.

Modification of a glycan structure on a human SAP polypeptide can increase the biological activity of the SAP polypeptide relative to a corresponding sample of wild-type SAP isolated from human serum. Isolated SAP from human serum contains only α2,6-linked sialic acid residues. In contrast, recombinant human SAP (rhSAP) produced in CHO cells contains only α2,3-linked sialic acid residues. In in vitro cell-based bioassays, α2,3-linked sialic acid SAP polypeptides demonstrate consistently higher activity than wild-type SAP (i.e., α2,6-linked sialic acid) isolated from human serum. The variant SAP polypeptides of the invention would be more effective as therapeutic agents due to their increased biological potency. For example, more potent SAP variants may require lower dosing and/or less frequent dosing relative to wild-type SAP isolated from human serum. The disclosure provides both variant human SAP polypeptides and methods for making the same. In particular, the present invention includes methods and compositions for in vitro and in vivo addition, deletion, or modification of sugar residues to produce a human SAP polypeptide having a desired glycosylation pattern.

Variant SAP Polypeptides

In part, the disclosure provides variant Serum Amyloid P (SAP) polypeptides for use in treatment of fibrotic cancers and cancer-associated fibrosis. In particular, SAP variants of the invention include glycosylated human SAP polypeptides that comprise one or more N-linked or O-linked oligosaccharide chains each independently having one, two, three, four, or five branches terminating with an α2,3-linked sialic acid moiety. In some embodiments, all the sialylated branches of the N-linked or O-linked oligosaccharide chains terminate in α2,3-linked moieties. Other SAP variants of the invention include glycosylated human SAP polypeptides that contain an N-linked or O-linked oligosaccharide chains having at least 20%, 25%, 30%, 35% 40%, 45%, 50%, 55%, 60%, 65% 75%, 80%, 85%, or even at least 95% fewer α2,6-linked sialic acid moieties than a wild-type SAP polypeptide derived from human serum. In some embodiments, the N-linked or O-linked oligosaccharide chains are substantially free of α2,6-linked sialic acid moieties. Glycovariant SAP polypeptides of the invention may comprise an N-linked oligosaccharide or O-linked chain having one or more branches (e.g., having a bi-antennary, tri-antennary, tetra-antennary, penta-antennary, etc. structure). In certain embodiments, SAP polypeptides of the invention comprise an N-linked or O-linked oligosaccharide chain wherein one, two, three, four, or five branches of the oligosaccharide chain are substantially free of galactose and N-acetylglucosamine. Certain SAP polypeptides of the invention have N-linked or O-linked oligosaccharide chains that are substantially free of galactose and N-acetylglucosamine. In some embodiments, SAP polypeptides of the invention comprise an N-linked or O-linked oligosaccharide chain wherein one, two, three, four, or five branches of the oligosaccharide chain contain one or more mannose residues. In certain embodiments, the SAP polypeptide of the invention comprises an N-linked oligosaccharide having a pentasaccharide core of Man[($\alpha$1,6-)-(Man($\alpha$1,3)]-Man($\beta$1,4)-GlcNAc($\beta$1,4)-GlcNAc($\beta$1,N)-Asn. This pentasaccharide core also may comprise one or more fucose or xylose residues. In certain embodiments, SAP polypeptides of the invention comprise an N-linked oligosaccharide chain wherein one, two, three, four, or five branches of the oligosaccharide chain have the structure NeuNAc2$\alpha$3Gal$\beta$4GlcNAc$\beta$2Man$\alpha$6. SAP polypeptides of the invention also may comprise an N-linked oligosaccharide chain wherein all branches have the structure NeuNAc2$\alpha$3Gal$\beta$4GlcNAc$\beta$2Man$\alpha$6.

Variant SAP polypeptides of the invention may comprise one or more "modified" sugar residues. Modified sugars are substituted at any position that allows for the attachment of the modifying moiety or group, yet which still allows the sugar to function as a substrate for the enzyme used to couple the modified sugar to the peptide. A modifying group can be attached to a sugar moiety by enzymatic means, chemical means or a combination thereof, thereby producing a modified sugar, e.g., modified galactose, fucose, or sialic acid. Modifying groups suitable for use in the present invention as well as methods for conjugating these modifying groups to sugar residues are described in the following section.

In some embodiments, the SAP polypeptides of the invention may comprise amino acid sequences at least 60%, at least 70%, at least 80%, at least 85%, at least 90%, at least 95%, at least 96%, at least 97%, at least 98%, at least 99%, or 100% identical to the amino acid sequence of SEQ ID NO: 1, as determined using the FASTDB computer program based on the algorithm of Brutlag et al. (Comp. App. Biosci., 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

Polypeptides sharing at least 95% identity with SEQ ID NO: 1 may include polypeptides having conservative substitutions in these areas of divergence. The term "SAP polypeptide" encompasses functional fragments and fusion proteins comprising any of the preceding. Generally, an SAP polypeptide will be soluble in aqueous solutions at biologically relevant temperatures, pH levels and osmolarity. The SAP protomers that non-covalently associate together to form a pentameric SAP complex may have identical amino acid sequences and/or post-translational modifications or, alternatively, individual SAP protomers within a single complex may have different sequences and/or modifications. The term SAP polypeptide includes polypeptides comprising any naturally occurring SAP polypeptide as well as any variant thereof (including mutants, fragments, and fusions). An SAP polypeptide of the invention may be a recombinant polypeptide. In preferred embodiments, the SAP polypeptide of the invention is a human SAP polypeptide.

In some embodiments, pharmaceutical compositions are provided comprising a variant SAP polypeptide of the invention, or a functional fragment thereof. In some aspects, the amino acid sequence of an SAP variant may differ from SEQ ID NO: 1 by one or more conservative or non-conservative substitutions. In other aspects, the amino acid sequence of an SAP variant may differ from SEQ ID NO: 1 by one or more conservative substitutions. As used herein, "conservative substitutions" are residues that are physically or functionally similar to the corresponding reference residues, i.e., a conservative substitution and its reference residue have similar size, shape, electrical charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. Additional guidance concerning which amino acid changes are likely to be phenotypically silent can be found in Bowie et al., Science 247:1306-1310 (1990).

Variant SAP polypeptides and fragments thereof that retain biological function are useful in the pharmaceutical compositions and methods described herein. In some embodiments, a variant SAP polypeptide or fragment thereof binds Fc$\gamma$RI, Fc$\gamma$RIIA, and/or Fc$\gamma$RIIIB. In some embodiments, a variant SAP polypeptide or fragment thereof inhibits one or more of fibrocyte, fibrocyte precursor, myofibroblast precursor, and/or hematopoetic monocyte precursor differentiation. SAP variants may be generated by modifying the structure of an SAP polypeptide for such purposes as enhancing therapeutic efficacy or stability (e.g., ex vivo shelf life and resistance to proteolytic degradation in vivo).

In certain aspects, the variant SAP polypeptides of the disclosure may further comprise post-translational modifications in addition to any that are naturally present in the SAP polypeptide. Such modifications include, but are not limited to, acetylation, carboxylation, glycosylation (e.g., O-linked oligosaccharides, N-linked oligosaccharides, etc.), phosphorylation, lipidation, and acylation. As a result, the modified SAP polypeptide may contain non-amino acid elements, such as polyethylene glycols, lipids, poly- or mono-saccharides, and phosphates.

Methods of producing variant hSAP polypeptides with altered N-glycosylation are described in U.S. patent application Ser. No. 12/794,132, which is hereby incorporated by reference.

In certain aspects, one or more modifications to the SAP polypeptide described herein may enhance the stability of the SAP polypeptide. For example, such modifications may enhance the in vivo half-life of the SAP polypeptide or reduce proteolytic degradation of the SAP polypeptide.

In certain aspects, variant SAP polypeptides of the invention include fusion proteins having at least a portion of the human SAP polypeptide and one or more fusion domains or heterologous portions. Well known examples of such fusion domains include, but are not limited to, polyhistidine, Glu-Glu, glutathione S transferase (GST), thioredoxin, protein A, protein G, and immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel-, or cobalt-conjugated resins are used. As another example, a fusion domain may be selected so as to facilitate detection of the SAP polypeptides. Examples of such detection domains include the various fluorescent protein (e.g., GFP) as well as "epitope tags," which are usually short peptide sequences for which a specific antibody is available. Well known epitope tags for which specific monoclonal antibodies are readily available include FLAG, influenza virus hemagglutinin (HA) and c-myc tags. In some cases, the fusion domains have a protease cleavage site that allows the relevant protease to partially digest the fusion proteins and thereby liberate the recombinant protein therefrom. The liberated proteins can then be isolated from the fusion domain by subsequent chromatographic separation. In some cases, the SAP polypeptide may be fused to a heterologous domain that stabilizes the SAP polypeptide in vivo. By "stabilizing" is meant anything that increases serum half-life, regardless of whether this is because of decreased destruction, decreased clearance by the liver and/or kidney, or other pharmacokinetic effect. Fusions with the Fc portion of an immunoglobulin and serum albumin are known to confer increased stability.

It is understood that different elements of the fusion proteins may be arranged in any manner that is consistent with the desired functionality. For example, an SAP polypeptide may be placed C-terminal to a heterologous domain, or, alternatively, a heterologous domain may be placed C-terminal to an SAP polypeptide. The SAP polypeptide and the heterologous domain need not be adjacent in a fusion protein, and additional domains or amino acid sequences (e.g., linker sequences) may be included C- or N-terminal to either domain or between the domains.

SAP polypeptides of the invention may comprise one or more "modified" sugar residues. A modifying group can be attached to a sugar moiety by enzymatic means, chemical means or a combination thereof, thereby producing a modified sugar, e.g., modified galactose, fucose, or sialic acid. When a modified sialic acid is used, either a sialyltransferase or a trans-sialidase can be used in these methods. The sugars may be substituted at any position that allows for the attachment of the modifying moiety, yet which still allows the sugar to function as a substrate for the enzyme used to couple the modified sugar to the peptide.

In general, the sugar moiety and the modifying group are linked together through the use of reactive groups, which are typically transformed by the linking process into a new organic functional group or unreactive species. The sugar reactive functional group(s) may be located at any position on the sugar moiety. Reactive groups and classes of reactions useful in practicing the present invention are generally those that are well known in the art of bioconjugate chemistry. Currently favored classes of reactions available with reactive sugar moieties are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, Smith and March, Advanced Organic Chemistry, 5th Ed., John Wiley & Sons, New York, 2001; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive functional groups pendent from a sugar nucleus or modifying group include, but are not limited to: (a) carboxyl groups and various derivatives thereof (e.g., N-hydroxysuccinimide esters, N-hydroxybenzotriazole esters, acid halides, acyl imidazoles, thioesters, p-nitrophenyl esters, alkyl, alkenyl, alkynyl and aromatic esters); (b) hydroxyl groups, which can be converted to, e.g., esters, ethers, aldehydes, etc.; (c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom; (d) dienophile groups, which are capable of participating in Diels-Alder reactions such as, for example, maleimido groups (e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (e) thiol groups, which can be, for example, converted to disulfides or reacted with alkyl and acyl halides; (h) amine or sulfhydryl groups, which can be, for example, acylated, alkylated or oxidized; (i) alkenes, which can undergo, for example, cycloadditions, acylation, Michael addition, metathesis, Heck reaction, etc.; (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., Protective Groups in Organic Synthesis, John Wiley & Sons, New York, 1991.

In some embodiments, the modified sugar is an activated sugar. Activated modified sugars useful in the present invention are typically glycosides which have been synthetically altered to include an activated leaving group. As used herein, the term "activated leaving group" refers to those moieties which are easily displaced in enzyme-regulated nucleophilic substitution reactions. Many activated sugars are known in the art. See, for example, Vocadlo et al., In Carbohydrate Chemistry and Biology, Vol. 2, Ernst et al. Ed., Wiley-VCH Verlag: Weinheim, Germany, 2000; Kodama et al., Tetrahedron Lett. 34: 6419 (1993); Lougheed, et al., J. Biol. Chem. 274: 37717 (1999)). Examples of such leaving groups include fluoro, chloro, bromo, tosylate, mesylate, triflate and the like. Preferred activated leaving groups for use in the present invention are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are most preferred.

In certain aspects, a modified sugar residue is conjugated to one or more water-soluble polymers. Many water-soluble polymers are known to those of skill in the art and are useful in practicing the present invention. The term water-soluble polymer encompasses species such as saccharides (e.g., dextran, amylose, hyaluronic acid, poly(sialic acid), heparans, heparins, etc.); poly(amino acids); nucleic acids; synthetic polymers (e.g., poly(acrylic acid), poly(ethers), e.g., poly(ethylene glycol)); peptides, proteins, and the like. The present invention may be practiced with any water-soluble polymer with the sole limitation that the polymer must include a point at which the remainder of the conjugate can be attached.

Methods and chemistry for activation of water-soluble polymers and saccharides as well as methods for conjugating saccharides and polymers to various species are described in the literature. Commonly used methods for activation of polymers include activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), Protein Immobilisation, Fundamentals and Applications, Marcel Dekker, N.Y.; S. S. Wong, (1992), Chemistry of Protein Conjugation and Crosslinking, CRC Press, Boca Raton; G. T. Hermanson et al., (1993), Immobilized Affinity Ligand Techniques, Academic Press, N.Y.; Dunn, R. L., et al., Eds. Polymeric Drugs and Drug Delivery Systems, ACS Symposium Series Vol. 469, American Chemical Society, Washington, D.C. 1991).

In certain aspects, a modified sugar residue is conjugated to one or more water-insoluble polymers. In some embodiments, conjugation to a water-insoluble polymer can be used to deliver a therapeutic peptide in a controlled manner. Polymeric drug delivery systems are known in the art. See, for example, Dunn et al., Eds. Polymeric drugs and Drug Delivery Systems, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly (ethyl methacrylate), poly(butyl methacrylate), poly (isobutyl methacrylate), poly(hexyl methacrylate), poly (isodecyl methacrylate), poly(lauryl methacrylate), poly (phenyl methacrylate), poly(methyl acrylate), poly (isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics, and polyvinylphenol, and copolymers thereof.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques. Representative biodegradable polymers useful in the conjugates of the invention include, but are not limited to, polylactides, polyglycolides and copolymers thereof poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, and pluronics.

In a preferred embodiment, one or more modified sugar residues are conjugated to one or more PEG molecules.

In certain aspects, the modified sugar is conjugated to a biomolecule. Biomolecule of the invention may include, but are not limited to, functional proteins, enzymes, antigens, antibodies, peptides, nucleic acids (e.g., single nucleotides or nucleosides, oligonucleotides, polynucleotides and single- and higher-stranded nucleic acids), lectins, receptors or a combination thereof.

Some preferred biomolecules are essentially non-fluorescent, or emit such a minimal amount of fluorescence that they are inappropriate for use as a fluorescent marker in an assay. Other biomolecules may be fluorescent.

In some embodiments, the biomolecule is a targeting moiety. A "targeting moiety" and "targeting agent", as used herein, refer to species that will selectively localize in a particular tissue or region of the body. In some embodiments, a biomolecule is selected to direct the SAP polypeptide of the invention to a specific intracellular compartment, thereby enhancing the delivery of the peptide to that intracellular compartment relative to the amount of underivatized peptide that is delivered to the tissue. The localization is mediated by specific recognition of molecular determinants, molecular size of the targeting agent or conjugate, ionic interactions, hydrophobic interactions and the like. Other mechanisms of targeting an agent to a particular tissue or region are known to those of still in the art.

In some embodiments, the modified sugar includes a therapeutic moiety. Those of skill in the art will appreciate that there is overlap between the category of therapeutic moieties and biomolecules, i.e., many biomolecules have therapeutic properties or potential.

Classes of useful therapeutic moieties include, for example, non-steroidal anti-inflammatory drugs; steroidal anti-inflammatory drugs; adjuvants; antihistaminic drugs; antitussive drugs; antipruritic drugs; anticholinergic drugs; anti-emetic and antinauseant drugs; anorexic drugs; central stimulant drugs; antiarrhythmic drugs; β-adrenergic blocker drugs; cardiotonic drugs; antihypertensive drugs; diuretic drugs; vasodilator drugs; vasoconstrictor drugs; antiulcer drugs; anesthetic drugs; antidepressant drugs; tranquilizer and sedative drugs; antipsychotic drugs; and antimicrobial drugs.

Other drug moieties useful in practicing the present invention include antineoplastic drugs, cytocidal agents, anti-estrogens, and antimetabolites. Also included within this class are radioisotope-based agents for both diagnosis (e.g., imaging) and therapy, and conjugated toxins.

The therapeutic moiety can also be a hormone, a muscle relaxant, an antispasmodic, bone activating agent, endocrine modulating agent, modulator of diabetes, androgen, antidiuretics, or calxitonin drug.

Other useful modifying groups include immunomodulating drugs, immunosuppressants, etc. Groups with anti-inflammatory activity, such as sulindac, etodolac, ketoprofen and ketorolac, are also of use. Other drugs of use in conjunction with the present invention will be apparent to those of skill in the art.

The altered N-glycosylation SAP polypeptides produced by the methods of the disclosure can be homogeneous (i.e., the sample of SAP polypeptide is uniform in specific N-glycan structure) or substantially homogeneous. By "substantially homogeneous" is meant that at least about 25% (e.g., at least about 27%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, or at least about 99%) of the SAP polypeptides contain the same specific N-glycan structure.

In some embodiments, variant SAP polypeptides of the invention have an $IC_{50}$ for inhibiting the differentiation of monocytes into fibrocytes in vitro that is less than ½, less than ⅓, less than ¼, less than 1/10, or less than 1/100 that of a corresponding sample of wild-type SAP isolated from human serum. In some embodiments, variant SAP polypeptides of the invention have an $IC_{50}$ for inhibiting the differentiation of monocytes into fibrocytes in vitro that is less than one-half that of a corresponding sample of wild-type SAP isolated from human serum. There are many well characterized methods for determining the responsiveness of Peripheral Blood Mononuclear Cells (PBMCs) or monocyte cells to SAP for fibrocyte differentiation. These methods may be used to determine the relative potency of any of the SAP variant polypeptides of the invention in comparison to a sample of human serum-derived SAP, any other SAP variant polypeptide, or other fibrocyte suppressant or activating agent. PBMCs or monocytes suitable for use in these methods may be obtained from various tissue culture lines. Alternatively, suitable cells for fibrocyte differentiation assays may be obtained from any biological sample that contains PBMC or monocyte cells. The biological sample may be obtained from serum, plasma, healthy tissue, or fibrotic tissue. In general, fibrocyte differentiation assays are conducted by incubating PBMC or monocyte cells in media with various concentrations of an SAP polypeptide to determine the degree of fibrocyte differentiation. The concentration of SAP can range from 0.0001 μg/mL to 1 mg/ml, and in some embodiments is 0.001 μg/mL, 1.0 μg/mL, 5 μg/mL, 10 μg/mL, 15 μg/mL, 20 μg/mL, 25 μg/mL, 30 μg/mL, 35 μg/mL, 40 μg/mL, 45 μg/mL, 50 μg/mL, 100 μg/mL, 200 μg/mL, 300 μg/mL, or 500 μg/mL. In some assays, the media can be supplemented with between 1-100 ng/ml hMCSF; the preferred concentration of hMCSF being 25 ng/mL. The indication that PBMC and monocytes have differentiated into fibrocytes can be determined by one skilled in the art. In general, fibrocytes are morphologically defined as adherent cells with an elongated spindle-shape and the presence of an oval nucleus. In some assays, cells are fixed and stained with Hema 3 before enumerating fibrocytes by direct counting, e.g., using an inverted microscope. The amount of fibrocyte differentiation is interpreted by one skilled in the art as an indication of a cell's responsiveness to SAP. As indicated by the examples of the disclosure, a greater suppression of fibrocyte differentiation indicates a greater degree of SAP responsiveness. An alternative method of measuring fibrocyte differentiation involves determining the expression of fibrocyte-specific cell surface markers or secreted factors, e.g., cytokines (such as IL-Ira, ENA-78/CXCL-5, PAI-1), fibronectin, collagen-1). Methods of detecting and/or quantifying cell surface markers or secreted factors are well known in the art, including but not limited to various ELISA- and FACS-based techniques using immunoreactive antibodies against one or more fibrocyte-specific markers. As described in the examples of the disclosure, measuring the expression of Macrophage Derived Chemokine (MDC) is an effective method of determining fibrocyte differentiation.

Methods for detecting and/or characterizing N-glycosylation (e.g., altered N-glycosylation) of an SAP polypeptide include DNA sequencer-assisted (DSA), fluorophore-assisted carbohydrate electrophoresis (FACE) or surface-enhanced laser desorption/ionization time-of-flight mass spectrometry (SELDI-TOF MS). For example, an analysis can utilize DSA-FACE in which, for example, glycoproteins are denatured followed by immobilization on, e.g., a membrane. The glycoproteins can then be reduced with a suitable reducing agent such as dithiothreitol (DTT) or β-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. The derivatized N-glycans can then be concentrated. Instrumentation suitable for N-glycan analysis includes, for example, the ABI PRISM® 377 DNA sequencer (Applied Biosystems). Data analysis can be performed using, for example, GENESCAN® 3.1 software (Applied Biosystems). Optionally, isolated mannoproteins can be further treated with one or more enzymes to confirm their N-glycan status. Exemplary enzymes include, for example, α-mannosidase or α-1,2 mannosidase. Additional methods of N-glycan analysis include, for example, mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al. (2001) Glycobiology 11(4):275-281 and Freire et al. (2006) Bioconjug. Chem. 17(2):559-564, the disclosures of each of which are incorporated herein by reference in their entirety.

Anti-FcγR Antibodies as SAP Agonists

In one aspect of the invention, one or more compounds are provided that mimic SAP signaling. In some embodiments, the SAP signaling agonists are anti-FcγR antibodies, wherein the antibodies are selected from a class of anti-FcγRI, anti-FcγRIIA, and anti-FcγRIII antibodies that are able to bind to either FcγRI, FcγRIIA, or FcγRIII, respectively. Anti-FcγR antibodies are IgG antibodies that bind to receptors for the Fc portion of IgG antibodies (FcγR). The anti-FcγR antibodies bind through their variable region, and not through their constant (Fc) region. Anti-FcγR antibodies may include any isotype of antibody. The anti-FcγR antibodies may be further cross-linked or aggregated with or without additional antibodies or other means. This process initiates intracellular signaling events consistent with FcγR activation. In some embodiments, the SAP signaling agonist may be a cross-linked FcγR.

Aggregated Fc Domains and Fc-Containing Antibodies

In some embodiments, the SAP signaling agonists are cross-linked or aggregated IgG. Cross-linked or aggregated IgG may include any IgG able to bind the target FcγR through its Fc region, provided that at least two such IgG antibodies are physically connected to one another.

Cross-linked or aggregated IgG may include whole antibodies or a portion thereof, preferably the portion functional in suppression of fibrotic disorders. For example, they may include any antibody portion able to cross-link FcγR. This may include aggregated or cross-linked antibodies or fragments thereof, such as aggregated or cross-linked whole antibodies, F(ab')$_2$ fragments, and possible even Fc fragments.

Aggregation or cross-linking of antibodies may be accomplished by any known method, such as heat or chemical aggregation. Any level of aggregation or cross-linking may be sufficient, although increased aggregation may result in increased fibrotic disorder suppression. Antibodies may be polyclonal or monoclonal, such as antibodies produced from hybridoma cells. Compositions and methods may employ mixtures of antibodies, such as mixtures of multiple monoclonal antibodies, which may be cross-linked or aggregated to like or different antibodies.

SAP Peptidomimetic

In certain embodiments, the SAP agonists include peptidomimetics. As used herein, the term "peptidomimetic" includes chemically modified peptides and peptide-like molecules that contain non-naturally occurring amino acids, peptoids, and the like. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of SAP polypeptides.

Increase SAP Activity

In some embodiments, an SAP agonist increases SAP activity. SAP activity can be increased by increasing the concentration of SAP by, for example, increasing SAP transcription, increasing translation, increasing SAP secretion, increasing SAP RNA stability, increasing SAP protein stability, or decreasing SAP protein degradation. SAP activity can also be increased by increasing specifically the "free concentration" of SAP, or rather the unbound form by, for example, decreasing SAP endogenous binding partners.

FcγR Crosslinkers

In some embodiments, fibronectin-based scaffold domain proteins may be used as SAP agonists to crosslink FcγRs. Fibronectin-based scaffold domain proteins may comprise a fibronectin type III domain (Fn3), in particular a fibronectin type III tenth domain ($^{10}$Fn3).

In order to crosslink FcγRs, multimers of FcγR binding Fn3 domains may be generated as described in U.S. Pat. No. 7,115,396.

Fibronectin type III (Fn3) domains comprise, in order from N-terminus to C-terminus, a beta or beta-like strand, A; a loop, AB; a beta or beta-like strand, B; a loop, BC; a beta or beta-like strand C; a loop CD; a beta or beta-like strand D; a loop DE; a beta or beta-like strand, E; a loop, EF; a beta or beta-like strand F; a loop FG; and a beta or beta-like strand G. The BC, DE, and FG loops are both structurally and functionally analogous to the complementarity-determining regions (CDRs) from immunoglobulins Fn3 domains can be designed to bind almost any compound by altering the sequence of one or more of the BC, DE, and FG loops. Methods for generating specific binders have been described in U.S. Pat. No. 7,115,396, disclosing high affinity TNFα binders, and U.S. Publication No. 2007/0148126, disclosing high affinity VEGFR2 binders. An example of fibronectin-based scaffold proteins are Adnectins™ (Adnexus, a Bristol-Myers Squibb R&D Company).

In some embodiments, the SAP agonist is an aptamer. In order to crosslink FcγRs, multimers of FcγR binding aptamers may be generated.

Aptamers are oligonucleotides, which can be synthetic or natural, that bind to a particular target molecule, such as a protein or metabolite. Typically, the binding is through interactions other than classic Watson-Crick base pairing. Aptamers represent a promising class of therapeutic agents currently in pre-clinical and clinical development. Like biologics, e.g., peptides or monoclonal antibodies, aptamers are capable of binding specifically to molecular targets and, through binding, inhibiting target function. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), Gene 137(1): 25-31; Jenison, et al. (1998), Antisense Nucleic Acid Drug Dev. 8(4): 265-79; Bell, et al. (1999), In vitro Cell. Dev. Biol. Anim 35(9): 533-42; Watson, et al. (2000), Antisense Nucleic Acid Drug Dev. 10(2): 63-75; Daniels, et al. (2002), Anal. Biochem. 305(2): 214-26; Chen, et al. (2003), Proc. Natl. Acad. Sci. U.S.A. 100(16): 9226-31; Khati, et al. (2003), J. Virol. 77(23): 12692-8; Vaish, et al. (2003), Biochemistry 42(29): 8842-51).

Aptamers have a number of attractive characteristics for use as therapeutics. In addition to high target affinity and specificity, aptamers have shown little or no toxicity or immunogenicity in standard assays (Wlotzka, et al. (2002), Proc. Natl. Acad. Sci. U.S.A. 99(13): 8898-902). Indeed, several therapeutic aptamers have been optimized and advanced through varying stages of pre-clinical development, including pharmacokinetic analysis, characterization of biological efficacy in cellular and animal disease models, and preliminary safety pharmacology assessment (Reyderman and Stavchansky (1998), Pharmaceutical Research 15(6): 904-10; Tucker et al., (1999), J. Chromatography B. 732: 203-212; Watson, et al. (2000), Antisense Nucleic Acid Drug Dev. 10(2): 63-75).

A suitable method for generating an aptamer to a target of interest is with the process entitled "Systematic Evolution of Ligands by EXponential Enrichment" ("SELEX™"). The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand is a specific ligand of a given target compound or molecule. The SELEX™ process is based on the insight that nucleic acids can form a variety of two- and three-dimensional structures and have sufficient chemical versatility available within their monomers to act as ligands (form specific binding pairs) with virtually any chemical compound, whether monomeric or polymeric. Molecules of any size or composition can serve as targets. The SELEX™ method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule. SELEX™ is a method for making a nucleic acid ligand for any desired target, as described, e.g., in U.S. Pat. Nos. 5,475,096 and 5,270,163, and PCT/US91/04078, each of which is specifically incorporated herein by reference.

In some embodiments, SAP agonists are Nanobodies®. Nanobodies® are antibody-derived therapeutic proteins that contain the unique structural and functional properties of naturally-occurring heavy-chain antibodies. The Nanobody® technology was originally developed following the discovery that camelidae (camels and llamas) possess fully functional antibodies that lack light chains. These heavy-chain antibodies contain a single variable domain (VHH) and two constant domains (CH2 and CH3). Importantly, the cloned and isolated VHH domain is a stable polypeptide harboring the full antigen-binding capacity of the original heavy-chain antibody. These VHH domains with their unique structural and functional properties form the basis of a new generation of therapeutic antibodies.

Cancer-Associated Fibrosis

A number of cancers are characterized by the presence of fibrosis. In part, the SAP polypeptides or SAP agonists of the disclosure are used, alone or in combination with an anti-cancer therapeutic, to treat a cancer characterized by such fibrosis (e.g., fibrotic cancers such as myelofibrosis, gastric cancer, pancreatic cancer, Hodgkin's lymphoma, non-Hodgkin's lymphoma, hairy cell leukemia, multiple myeloma, medulloblastoma, myeloid leukemia, acute lymphocytic leukemia, and cancers of the breast, uterus, or colon, including fibroids, fibroma, fibroadenomas and fibrosarcomas). In other embodiments, an SAP agonist of the disclosure, such as an SAP polypeptide (such as a recombinant human SAP polypeptide, such as a glycosylated SAP polypeptide) is used as a monotherapy.

In certain embodiments, the SAP polypeptides or SAP agonists of the disclosure (e.g., an SAP agonist comprising a glycosylated SAP polypeptide; SAP comprising a glycosylated SAP polypeptide; recombinant human SAP; etc.) are used, alone or in combination with an anti-cancer therapeutic, to treat a fibrotic cancer (e.g., fibrotic cancers such as myelofibrosis, gastric cancer, pancreatic cancer, Hodgkin's lymphoma, non-Hodgkin's lymphoma, hairy cell leukemia, multiple myeloma, medulloblastoma, myeloid leukemia, acute lymphocytic leukemia, and cancers of the breast, uterus, or colon, including fibroids, fibroma, fibroadenomas and fibrosarcomas) by decreasing fibrosis to restore organ function. It is shown here that administering an SAP polypeptide or SAP agonist of the disclosure as a single agent or as part of a combination therapy, resulted in a decrease in organ fibrosis (e.g. bone marrow fibrosis), leading to improvements and/or restoration of organ function and improvement in fibrotic cancer symptoms (e.g. improvement in complete blood counts (CBC)). Improvement in organ function can be evaluated for example, by assessing improvement in platelet levels and/or hemoglobin in the subject over the course of treatment, such as over 12, 20, 24, or greater than 24 weeks of treatment. In some embodiments, the organ is the bone marrow, and treatment decreases organ fibrosis and/or improves organ function. In some embodiments, the fibrotic organ is the lung, stomach, pancreas, colon, liver, kidney, bladder, breast, uterus, cervix, ovary, or brain. In some embodiments, the fibrotic cancer is myelofibrosis.

As described herein, in certain embodiments, addition of SAP to a therapeutic regimen is used in a subject who is unresponsive, resistant or otherwise refractory to a treatment (in the absence of the SAP) or for whom efficacy of the treatment is or has waned. In certain embodiments, the addition of SAP is used to expand the patient population for which treatment with another therapeutic agent is suitable (e.g., SAP expands the therapeutic window or patient population for another drug). By way of example, certain cancers are known to be unresponsive to chemotherapy. Without being bound by theory, fibrosis may hinder effective access of the drugs to the tumor.

In certain embodiments, as described herein, addition of SAP to a therapeutic regimen is used to improve the safety of treatment, such as by reducing one or more side effects observed in subjects treated with the additional anti-cancer therapeutic alone.

In certain embodiments, an SAP agonist or SAP polypeptide is used as a monotherapy and/or is used to treat naïve patients. In certain embodiments, an SAP agonist or SAP polypeptide is used in patients whose disease has a certain fibrotic score, such as bone marrow fibrosis of Grade 2 or Grade 3, as assessed by the European Consensus on Grading of Bone Marrow Fibrosis.

In certain aspects, the invention encompasses the use of an SAP polypeptide or SAP agonist, as a single agent or in combination with another agent, for the treatment of myelofibrosis. Myelofibrosis ("MF") is a BCR-ABL1-negative myeloproliferative neoplasm ("MPN") that presents de novo (primary) or may be preceded by polycythemia vera ("PV") or essential thrombocythemia ("ET"). Primary myelofibrosis (PMF) (also referred to in the literature as idiopathic myeloid metaplasia, and Agnogenic myeloid metaplasia) is a clonal disorder of multipotent hematopoietic progenitor cells of monocytic lineage (reviewed in Abdel-Wahab, O. et al. (2009) Annu Rev. Med. 60:233-45; Varicchio, L. et al. (2009) Expert Rev. Hematol. 2(3):315-334; Agrawal, M. et al. (2011) Cancer 117(4):662-76). The disease is characterized by anemia, splenomegaly and extramedullary hematopoiesis, and is marked by progressive marrow fibrosis and a typical megakaryocytic hyperplasia. CD34+ stem/progenitor cells abnormally traffic in the peripheral blood and multi organ extramedullary erythropoiesis is a hallmark of the disease, especially in the spleen and liver. The bone marrow structure is altered due to progressive fibrosis, neoangiogenesis, and increased bone deposits. Median survival ranges from less than 2 years to over 15 years based on currently identified prognostic factors (Cervantes F et al., Blood 113:2895-2901, 2009; Hussein K et al. Blood 115:496-499, 2010; Patnaik M M et al., Eur J Haematol 84:105-108, 2010). A significant percentage of patients with PMF have gain-of-function mutations in genes that regulate hematopoiesis, including Janus kinase 2 (JAK2) (about 50%) (e.g., JAK2 V617F) or the thrombopoietin receptor (MPL) (5-10%), resulting in abnormal megakaryocyte growth and differentiation. Studies have suggested that the clonal hematopoietic disorder leads to secondary proliferation of fibroblasts and excessive collagen deposition. Decreased bone marrow fibrosis can improve clinical signs and symptoms, including anemia, thrombocytopenia, leukopenia, and splenomegaly.

It is known in the literature that inhibitors of JAK2 are useful in the treatment and/or prevention of myeloproliferative disorders. See, e.g., Tefferi, A. and Gilliland, D. G. Mayo Clin. Proc. 80(7): 947-958 (2005); Fernandez-Luna, J. L. et al. Haematologica 83(2): 97-98 (1998); Harrison, C. N. Br. J. Haematol. 130(2): 153-165 (2005); Leukemia (2005) 19, 1843-1844; and Tefferi, A. and Barbui, T. Mayo Clin. Proc. 80(9): 1220-1232 (2005). However, the management options of MF are currently inadequate to meet the needs of all patients. Therefore, there is a need to provide additional therapy options for MF patients.

In some embodiments of the methods provided herein, the subject has primary myelofibrosis. In some embodiments of the compositions and methods provided herein, the subject has post polycythemia vera myelofibrosis (post-PV MF). In some embodiments, the subject has post essential thrombocythemia myelofibrosis (post-ET MF). In some embodiments, the subject has high risk myelofibrosis. In some embodiments, the subject has intermediate risk myelofibrosis (such as intermediate risk level 1 or intermediate risk level 2). In some embodiments, the subject has low risk myelofibrosis. In some embodiments, the subject has PV or ET without fibrosis. In some embodiments, the subject is positive for the valine 617 to phenylalanine mutation of human Janus Kinase 2 (JAK2) or positive for the mutation corresponding to the valine 617 to phenylalanine mutation of human JAK2. In some embodiments, the subject is negative for the valine 617 to phenylalanine mutation of human Janus Kinase 2 (JAK2) or negative for the mutation corresponding to the valine 617 to phenylalanine mutation of human JAK2. In some embodiments, prior to initiation of treatment with a SAP agonist or SAP polypeptide of the disclosure, the subject has bone marrow fibrosis and the fibrosis is measurable according to the grading system of the European Consensus on Grading of Bone Marrow Fibrosis. In some embodiments, prior to initiation of treatment with a SAP agonist or SAP polypeptide of the disclosure, the subject has bone marrow fibrosis of greater than or equal to Grade 2. In other embodiments, prior to initiation of treatment with a SAP agonist or SAP polypeptide of the disclosure, the subject has bone marrow fibrosis of Grade 3.

In certain aspects, the fibrotic cancer is a desmoplastic tumor, such as pancreatic cancer and/or neuroendocrine tumors. Pancreatic cancer is characterized by a prominent desmoplastic reaction, a key histopathological feature of pancreatic cancer that contributes to its well known resistance to chemotherapeutic agents. This feature of pancreatic cancer is now considered to be an alternative therapeutic target in pancreatic cancer. The SAP polypeptides and SAP agonists of the disclosure are believed to be effective in depleting or reducing desmoplastic stroma and/or fibrosis, rendering the tumor more accessible to chemotherapy.

In certain aspects, the cancer-associated fibrosis is bone marrow fibrosis. In certain embodiments, the fibrotic condition of the bone marrow is an intrinsic feature of a chronic myeloproliferative neoplasm of the bone marrow, such as primary myelofibrosis. In other embodiments, the bone marrow fibrosis is associated with a malignant condition or a condition caused by a clonal proliferative disease or a hematologic disorder such as but not limited to hairy cell leukemia, lymphoma (e.g., Hodgkin or non-Hodgkin lymphoma), multiple myeloma or chronic myelogeneous leukemia (CML). In yet other embodiments, the bone marrow fibrosis is associated with a solid tumor metastasis to the bone marrow.

In some embodiments, the fibrosis is associated with a cancer including, but not limited to, biliary cancer (e.g., cholangiocarcinoma), bladder cancer, breast cancer (e.g., adenocarcinoma of the breast, inflammatory carcinoma of the breast, papillary carcinoma of the breast, medullary carcinoma of the breast), brain cancer (e.g., meningioma; glioma, e.g., astrocytoma, oligodendroglioma; medulloblastoma), cervical cancer (e.g., squamous cell carcinoma of the cervix, cervical adenocarcinoma), colorectal cancer (e.g., colon cancer, rectal cancer, colorectal adenocarcinoma), esophageal cancer, gastric cancer, gastrointestinal stromal tumor (GIST), head and neck cancer (e.g., head and neck squamous cell carcinoma, oral cancer (e.g., oral squamous cell carcinoma (OSCC)), keloids, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphocytic leukemia (ALL), acute myelogenous leukemia (AML), chronic myelogenous leukemia (CML), chronic lymphocytic leukemia (CLL)), lymphoma (e.g., Hodgkin lymphoma (HL), non-Hodgkin lymphoma (NHL) including, but not limited to follicular lymphoma, diffuse large B-cell lymphoma (DLBCL), mantle cell lymphoma (MCL)), medulloblastoma, multiple myeloma (MM), myelodysplastic syndrome (MDS), myeloproliferative disorder (MPD) (e.g., polycythemia vera (PV), essential thrombocythemia (ET), agnogenic myeloid metaplasia (AMM) a.k.a. primary myelofibrosis (PMF), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), pancreatic cancer (e.g., pancreatic adenocarcinoma, intraductal papillary mucinous neoplasm (IPMN)), prostate cancer (e.g., prostate adenocarcinoma), skin cancer (e.g., squamous cell carcinoma (SCC), keratoacanthoma (KA), melanoma, basal cell carcinoma (BCC), dermatofibroma), soft tissue tumors (e.g., angiolipoma, angioleiomyoma, malignant fibrous histiocytoma (MFH), liposarcoma, malignant peripheral nerve sheath tumor (MPNST), chondrosarcoma, fibrosarcoma, myxosarcoma, osteosarcoma), and any other tumors associated with desmoplasia. In such embodiments, the SAP polypeptides or SAP agonist can decrease fibrosis, thus leading to improved drug delivery and/or survival.

Treatment Methods

In one aspect, the disclosure provides methods for treating a fibrotic cancer or cancer-associated fibrosis in a patient by administering a therapeutically effective amount of an SAP polypeptide or SAP agonist of the disclosure, as a single agent or in combination with an anti-cancer therapeutic, to a patient in need thereof. The dosage and frequency of treatment can be determined by one skilled in the art and will vary depending on the symptoms, age and body weight of the patient, and the nature and severity of the disorder to be treated or prevented. The present disclosure has identified dosing regimens that are effective in treating myelofibrosis.

Administration of an SAP polypeptide or SAP agonist of the disclosure, singly or in combination with another anti-cancer therapeutic, according to either a weekly dosing schedule or a less frequent dosing schedule (e.g., less than weekly, such as every 4 weeks), resulted in significant improvements in fibrotic cancer symptoms. Moreover, the methods of the disclosure are also based on the finding that an SAP polypeptide or SAP agonist of the disclosure was well tolerated both alone and in combination with another anti-cancer therapeutic, with no evidence of clinically significant myelosuppression induced by the SAP treatment, e.g., treatment-related myelosuppression.

In certain aspects, the disclosure provides methods for treating a fibrotic cancer or cancer-associated fibrosis in a patient by administering to a patient in need thereof an SAP polypeptide or SAP agonist of the disclosure, as a single agent or in combination with an anti-cancer therapeutic, in an amount effective to improve the functioning of the affected organ. Improvement in function may be evaluated by, for example, evaluating a decrease in organ fibrosis, an improvement in platelet levels, and/or an increase in hemoglobin. In some embodiments, the fibrotic organ is the bone marrow. In some embodiments, the fibrotic cancer is myelofibrosis. In some embodiments, the fibrotic organ is the lung, stomach, pancreas, colon, liver, kidney, bladder, breast, uterus, cervix, ovary, or brain.

In some embodiments, an SAP polypeptide or SAP agonist is administered to a patient once or twice per day, once or twice per week, once or twice per month, or just prior to or at the onset of symptoms. In some embodiments, an SAP polypeptide or SAP agonist is administered to a patient with PV or ET who has not yet developed fibrosis, to prevent development of fibrosis.

Dosages may be readily determined by techniques known to those of skill in the art or as taught herein. Toxicity and therapeutic efficacy of an SAP polypeptide or SAP agonist may be determined by standard pharmaceutical procedures in experimental animals, for example, determining the $LD_{50}$ and the $ED_{50}$. The $ED_{50}$ (Effective Dose 50) is the amount of drug required to produce a specified effect in 50% of an animal population. The $LD_{50}$ (Lethal Dose 50) is the dose of drug which kills 50% of a sample population.

In certain aspects, an SAP polypeptide or SAP agonist is administered as a single agent for treating a fibrotic cancer or cancer-associated fibrosis in a subject. In certain aspects, administering a combination of an SAP polypeptide or SAP agonist (e.g., a variant SAP polypeptide of the disclosure) and an anti-cancer therapeutic (e.g., a chemotherapeutic agent or a tyrosine kinase inhibitor) provides synergistic effects for treating a fibrotic cancer, e.g., myelofibrosis or pancreatic cancer in a subject. Such an approach, combination or co-administration of the two types of agents, can be useful for treating individuals suffering from fibrotic cancers who do not respond to or are resistant to currently-available therapies. The combination therapy provided herein is also useful for improving the efficacy and/or reducing the side effects of currently-available cancer therapies for individuals who do respond to such therapies.

A tested combination therapy resulted in improvement of negative side effects (e.g. anemia and thrombocytopenia) observed in the patients who, prior to initiation of treatment with SAP, were being treated with a Jak kinase inhibitor alone.

In certain embodiments, the disclosure provides methods of treating myelofibrosis, comprising administering an amount of an SAP agonist, such as an SAP polypeptide, to a subject in need thereof according to a dosing regimen (e.g., a dose and dosing schedule) and/or dosing schedule effective to ameliorate one or more symptoms of myelofibrosis, wherein the subject in need thereof was previously treated with and has ceased responding to treatment with a JAK kinase inhibitor. This is similarly applicable more broadly to patients having other fibrotic cancers and/or being treated with other anti-cancer therapeutics.

In certain embodiments, the disclosure provides methods of treating myelofibrosis, comprising administering an amount of an SAP agonist, such as an SAP polypeptide, to a subject in need thereof according to a dosing regimen (e.g., a dose and dosing schedule) and/or dosing schedule effective to ameliorate one or more symptoms of myelofibrosis, wherein the subject in need thereof is currently being treated with a JAK kinase inhibitor. Accordingly, the present disclosure provides, in part, methods in which an SAP agonist, such as an SAP polypeptide, can be used in a combination with a JAK kinase inhibitor to achieve a greater therapeutic effect at ameliorating one or more symptoms of myelofibrosis than is observed with treating a myelofibrosis patient with a JAK kinase inhibitor alone. In some embodiments, the methods of the disclosure do not induce treatment-related myelosuppression (e.g., the SAP agonist does not induce clinically significant myelosuppression and/or does not increase (and may even decrease) myelosuppression present at baseline. In other words, in certain embodiments, methods of the present disclosure do not induce or result in worsening of myelosuppression in comparison to, for example, that observed prior to initiation of treatment. Myelosuppression may be assessed according to the Common Terminology for Coding of Adverse Events (CTCAE) on a scale of Grade 0-Grade 5 (See National Cancer Institute Common Terminology Criteria for Adverse Events v4.0, NCI, NIH, DHHS. May 29, 2009 NIH publication #09-7473). In some embodiments, one or more measures of myelosuppression, such as anemia, do not deteriorate (e.g., from a Grade 3 to Grade 4 adverse event; from a Grade 2 to Grade 3 adverse event) as a result of treatment.

By "ceased responding to treatment" is meant that the subject is no longer having any response to the treatment or has decreased responsiveness to the treatment, such as requiring increased dose or receiving a decreased benefit. In certain embodiments, the subject in need thereof was previously treated with and has ceased responding to treatment with ruxolitinib, or with another Jak kinase inhibitor. In certain embodiments, the method further comprises administering an additional anti-cancer therapy. In certain embodiments, the additional anti-cancer therapy is the same therapy to which the subject has previously ceased responding.

In one aspect, the disclosure provides methods for treating cancer-associated fibrosis or fibrotic cancers by administering an SAP polypeptide or SAP agonist in combination with an anti-cancer therapeutic. As used herein, "in combination with" or "conjoint administration" refers to any form of administration such that the second compound is still effective in the body (e.g., the two compounds are simultaneously effective in the patient, which may include synergistic effects of the two compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapeutics. The SAP polypeptide or SAP agonist can be administered concurrently with, prior to, or subsequent to, one or more other additional agents.

In some embodiments, the SAP polypeptide or SAP agonist is administered to patients who are already receiving stable anti-cancer therapy. In some embodiments, the patients have been receiving stable anti-cancer therapy for at least 3 months. In some embodiments, the patients have been receiving stable anti-cancer therapy for less than 3 months. In some embodiments, the patients have been receiving stable anti-cancer therapy for at least 2 weeks, at least 3 weeks, at least 1 month, at least 2 months, at least 3 months, at least 4 months, at least 6 months, at least 7 months, at least 8 months, at least 9 months, at least 10 months, at least 11 months, or at least a year. In certain embodiments, the stable anti-cancer therapy is a JAK kinase inhibitor, such as ruxolitinib.

In general, each therapeutic agent will be administered at a dose and/or on a time schedule determined for that particular agent. The particular combination to employ in a regimen will take into account compatibility of the SAP polypeptide or SAP agonist with the agent and/or the desired therapeutic effect to be achieved.

Anti-cancer therapeutics of the invention may include, but are not limited to chemotherapy agents, antibody-based agents, tyrosine kinase inhibitors, immunomodulatory agents and biologic agents or combinations thereof. Chemotherapy agents include, but are not limited to actinomycin D, aldesleukin, alitretinoin, all-trans retinoic acid/ATRA, altretamine, amascrine, asparaginase, azacitidine, azathioprine, bacillus calmette-guerin/BCG, bendamustine hydrochloride, bexarotene, bicalutamide, bleomycin, bortezomib, busulfan, capecitabine, carboplatin, carfilzomib, carmustine, chlorambucil, cisplatin/cisplatinum, cladribine, cyclophosphamide/cytophosphane, cytabarine, dacarbazine, daunorubicin/daunomycin, denileukin diftitox, dexrazoxane, docetaxel, doxorubicin, epirubicin, etoposide, fludarabine, fluorouracil (5-FU), gemcitabine, goserelin, hydrocortisone, hydroxyurea, idarubicin, ifosfamide, interferon alfa, irinotecan CPT-11, lapatinib, lenalidomide, leuprolide, mechlorethamine/chlormethine/mustine/HN2, mercaptopurine, methotrexate, methylprednisolone, mitomycin, mitotane, mitoxantrone, octreotide, oprelvekin, oxaliplatin, paclitaxel, pamidronate, pazopanib, pegaspargase, pegfilgrastim, PEG interferon, pemetrexed, pentostatin, phenylalanine mustard, plicamycin/mithramycin, prednisone, prednisolone, procarbazine, raloxifene, romiplostim, sargramostim, streptozocin, tamoxifen, temozolomide, temsirolimus, teniposide, thalidomide, thioguanine, thiophosphoamide/thiotepa, thiotepa, topotecan hydrochloride, toremifene, tretinoin, valrubicin, vinblastine, vincristine, vindesine, vinorelbine, vorinostat, zoledronic acid, or combinations thereof. Antibody-based agents include, but are not limited to alemtuzumab, bevacizumab, cetuximab, fresolimumab, gemtuzumab ozogamicin, ibritumomab tiuxetan, ofatumumab, panitumumab, rituximab, tositumomab, trastuzumab, trastuzumab DM1, and combinations thereof. Immunomodulatory compounds include, but are not limited to small organic molecules that inhibit TNFα, LPS induced monocyte IL1β, IL12, and IL6 production. In some embodiments, immunomodulatory compounds include but are not limited to methotrexate, leflunomide, cyclophosphamide, cyclosporine A, minocycline, azathioprine, an antibiotic (e.g., tacrolimus), methylprednisolone, a corticosteroid, a steroid, mycophenolate mofetil, rapamycin, mizoribine, deoxyspergualin, brequinar, a T cell receptor modulator, or a cytokine receptor modulator, and a Toll-like receptor (TLR) agonist. In some embodiments, immunomodulatory compounds include 5,6-dimethylxanthenone-4-acetic acid (DMXAA), thalidomide, lenalidomide, pomalidomide, lactoferrin, polyadenosine-polyuridylic acid (poly AU), rintatolimod (polyI:polyCl2U; Hemispherx Biopharma), polyinosinic-polycytidylic acid stabilized with poly-L-lysine and carboxymethylcellulose (Poly-ICLC, Hiltonol®), imiquimod (3M) and resiquimod (R848; 3M), unmethylated CpG dinucleotide (CpG-ODN), and ipilumumab. Biologic agents include monoclonal antibodies (MABs), CSFs, interferons and interleukins. In some embodiments, the biologic agent is IL-2, IL-3, erythropoietin, G-CSF, filgrastim, interferon alfa, alemtuzumab, bevacizumab, cetuximab, gemtuzumab ozogamicin, ibritumomab tiuxetan, ofatumumab, panitumumab, rituximab, tositumomab or trastuzumab.

Tyrosine kinase inhibitors include, but are not limited to axitinib, bafetinib, bosutinib, cediranib, crizotinib, dasatinib, erlotinib, gefitinib, imatinib, lapatinib, neratinib, nilotinib, ponatinib, quizartinib, regorafenib, sorafenib, sunitinib, vandetanib, vatalanib, and combinations thereof.

In some embodiments, the anti-cancer therapeutic is a JAK kinase inhibitor such as, but not limited to AC-430, AZD1480, baricitinib, BMS-911453, CEP-33779, CYT387, GLPG-0634, lestaurtinib, LY2784544, NS-018, pacritinib, R-348, R723, ruxolitinib, TG101348 (SAR302503), tofacitinib, and VX-509.

In certain embodiments, the anti-cancer therapeutic includes but is not limited to antimetabolites (e.g., 5-fluorouracil, cytarabine, methotrexate, fludarabine and others), antimicrotubule agents (e.g., vinca alkaloids such as vincristine, vinblastine; taxanes such as paclitaxel and docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, satraplatin and CI-973), anthracyclines (e.g., doxrubicin and daunorubicin), antitumor antibiotics (e.g., mitomycin, idarubicin, adriamycin and daunomycin), topoisomerase inhibitors (e.g., etoposide and camptothecins), anti-angiogenesis agents (e.g., sunitinib, sorafenib and bevacizumab) or any other cytotoxic agents, (e.g. estramustine phosphate, prednimustine), hormones or hormone agonists, antagonists, partial agonists or partial antagonists, kinase inhibitors (such as imatinib), and radiation treatment.

Any treatment method of the disclosure may be repeated as needed or required. For example, the treatment may be done on a periodic basis. The frequency of administering treatment may be determined by one of skill in the art. For example, treatment may be administered once a week for a period of weeks, or multiple times a week for a period of time (e.g., 3 times over the first week of treatment). In some embodiments, an initial loading dose period is followed by a maintenance dose. In some embodiments, the loading dose is periodically repeated. In some embodiments, the initial loading dose period includes administering the treatment multiple times a week (e.g., 3 times over the first week of treatment). In some embodiments, the loading dose may be repeated every other week, every month, every two months, every 3 months, or every 6 months, or as needed, with or without continued periodic dosing between loading doses. Generally, the amelioration of the cancer-associated fibrosis persists for some period of time, preferably at least months, but maintenance of the anti-fibrotic effect and/or prevention of recurrence of fibrosis may require continued periodic dosing of an SAP polypeptide or SAP agonist over an unlimited period of time. Over time, the patient may experience a relapse of symptoms, at which point the treatments may be repeated.

In certain aspects, methods are provided herein for treating, delaying development, and/or preventing myelofibrosis in a subject comprising administering to the subject an effective amount of an SAP polypeptide or SAP agonist, or a pharmaceutically acceptable salt thereof, alone or in combination with an anti-cancer therapeutic. In some embodiments, the subject has myelofibrosis. In some embodiments, the subject is at risk of developing myelofibrosis. In some embodiments, the subject is a human subject. Any one of the formulations described herein such as capsule or unit dosage forms described herein may be used to treat a subject with myelofibrosis.

Myelofibrosis that may be treated by the methods described herein includes primary myelofibrosis (PMF) and secondary myelofibrosis (e.g., myelofibrosis arising from antecedent polycythemia vera (post-PV MF) or essential thrombocythemia (post-ET MF)). Myelofibrosis that may be treated by the methods described herein also includes myelofibrosis of high risk, intermediate risk such as intermediate risk level 1 or intermediate risk level 2, and low risk. Methods for diagnosing various types of myelofibrosis are known in the art. See, e.g., Cervantes et al., Blood 2009, 113(13):2895-901. In some embodiments, a dynamic prognostic model that accounts for modifications to the risk profile after diagnosis may prove useful. See, e.g., Passamonti et al., Blood 2010, 115:1703-1708. In some embodiments, the subject has palpable splenomegaly. In some embodiments, the subject with myelofibrosis has spleen of at least 5 cm below costal margin as measured by palpation. In some embodiments, the subject has anemia and/or thrombocytopenia and/or leukopenia. In some embodiments, the subject does not have anemia or thrombocytopenia or leukopenia. In some embodiments, the subject is transfusion dependent. In some embodiments, the subject is not transfusion dependent. In some embodiments, the subject has a pathologically confirmed diagnosis of PMF as per the WHO diagnostic criteria or post ET/PV MF, including the presence of at least Grade 2 marrow fibrosis with intermediate −1, intermediate −2, or high risk disease according to the IWG-MRT Dynamic International Prognostic Scoring System. In some embodiments, the subject has a pathologically confirmed diagnosis of PMF as per the WHO diagnostic criteria or post ET/PV MF, with Grade 0 or 1 bone marrow fibrosis and low risk, intermediate −1, intermediate −2, high risk, or low risk disease according to the IWG-MRT Dynamic International Prognostic Scoring System. In some embodiments, the subject has "prefibrotic" myelofibrosis. In some embodiments, the subject has PV or ET and receives an SAP polypeptide or SAP agonist to prevent development of myelofibrosis.

In some embodiments, the subject has a point mutation from valine 617 to phenylalanie in the Janus kinase 2 (JAK2 kinase) (JAK2V617F) if the subject is a human, or a point mutation corresponding to the valine 617 to phenylalanie in the Janus kinase 2 (JAK2 kinase) if the subject is not a human. In some embodiments, the subject is negative for the valine 617 to phenylalanine mutation of JAK2 if the subject is a human, or negative for a mutation corresponding to the valine 617 to phenylalanie in the Janus kinase 2 (JAK2 kinase) if the subject is not a human. Whether a subject is positive or negative for JAK2V617F can be determined by a polymerase chain reaction ("PCR") analysis using genomic DNA from bone marrow cells or blood cells (e.g., whole blood leukocytes). The PCR analysis can be an allele-specific PCR (e.g., allele-specific quantitative PCR) or PCR sequencing. See Kittur J et al., Cancer 2007, 109(11): 2279-84 and McLornan D et al., Ulster Med J. 2006, 75(2): 112-9, each of which is expressly incorporated herein by reference.

In some embodiments, the subject treated with the methods described herein has previously received or is currently receiving another myelofibrosis therapy or treatment. In some embodiments, the subject is a non-responder to the other myelofibrosis therapy or has a relapse after receiving the other myelofibrosis therapy. The previous therapy may be a JAK2 inhibitor (e.g. INCB018424 (also known as ruxolitinib, available from Incyte), CEP-701 (lestaurtinib, available from Cephalon), or XL019 (available from Exelixis)) (See Verstovsek S., Hematology Am Soc Hematol Educ Program. 2009:636-42) or a non-JAK2 inhibitor (such as hydroxyurea). In some embodiments, the previous therapy may be JAK kinase inhibitor such as, but not limited to AC-430, AZD1480, baricitinib, BMS-911453, CEP-33779, CYT387, GLPG-0634, INCB18424, lestaurtinib, LY2784544, NS-018, pacritinib, ruxolitinib, TG101348 (SAR302503), tofacitinib, VX-509, R-348, or R723. In some embodiments, the subject has received ruxolitinib treatment for primary myelofibrosis, post-polycythemia vera myelofibrosis (Post-PV MF), post-essential thrombocythemia myelofibrosis (Post-ET MF), polycythemia vera, or essential thrombocythemia for at least three months. In some embodiments, the subject has received ruxolitinib treatment for primary myelofibrosis, post-polycythemia vera myelofibrosis (Post-PV MF), post-essential thrombocythemia myelofibrosis (Post-ET MF), polycythemia vera, or essential thrombocythemia for less than three months. In some embodiments, the subject has received ruxolitinib treatment for primary myelofibrosis, post-polycythemia vera myelofibrosis (Post-PV MF), post-essential thrombocythemia myelofibrosis (Post-ET MF), polycythemia vera, or essential thrombocythemia for at least three months. In some embodiments, at least one or more symptoms have ceased to improve on continued ruxolitinib therapy. In some embodiments, the subject is no longer responsive to ruxolitinib. In some embodiments, the subject has previously received another myelofibrosis therapy for at least 6 months, at least 5 months, at least 4 months, at least 3 months, at least 2 months, at least 1 month, at least 3 weeks, or at least 2 weeks. In some embodiments, the subject is no longer responsive to the other myelofibrosis therapy. In some embodiments, the previous therapy is an anti-cancer therapeutic described herein and the previous therapy has been discontinued upon indication of one or more elevated levels of amylase, lipase, aspartate aminotransferase (AST), alanine aminotransferase (ALT), and/or creatinine in the serum from the subject, and/or upon indication of a hematologic condition selected from the group consisting of anemia, thrombocytopenia, and neutropenia, or for any other reason based on a decision by the treating physician or the patient's request. In some embodiments, the dose of the compound in the second treatment is the same or lower than the dose in the previous therapy. In some embodiments, the subject has not received any therapy other than transfusions. In some embodiments, the subject has not received any prior therapy.

In some embodiments, the SAP polypeptide or SAP agonist is administered in combination with a JAK kinase inhibitor such as, but not limited to AC-430, AZD1480, baricitinib, BMS-911453, CEP-33779, CYT387, GLPG-0634, INCB18424, lestaurtinib, LY2784544, NS-018, pacritinib, ruxolitinib, TG101348 (SAR302503), tofacitinib, VX-509, R-348, or R723 (See Kontzias et al. Curr Opin Pharmacol. 2012, 12(4):464-470). In some embodiments, the SAP polypeptide or SAP agonist is administered in combination with an agent known to reduce the symptoms of myelofibrosis, such as, but not limited to AB0024, AZD1480, AT-9283, BMS-911543, CYT387, everolimus, givinostat, imetelstat, lestaurtinib, LY2784544, oral arsenic, NS-018, pacritinib, panobinostat, peginterferon alfa-2a, pomalidomide, pracinostat, ruxolitinib, TAK-901, and TG101438 (SAR302503) (Mesa, Leuk Lymphoma 2013, 54(2):242-251; Gupta et al. 2012, 2(3):170-186; Kucine and Levine 2011, 2(4):203-211).

The subject (such as a human) may be treated by administering the SAP polypeptide or SAP agonist at a dose of about 0.1 mg/kg to about 40 mg/kg. In some embodiments, the SAP polypeptide or SAP agonist is administered at a dose of 10 mg/kg. In some embodiments, the compound is administered at a dose of about any of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 8 mg/kg, 10 mg/kg, 12 mg/kg, 15 mg/kg, 18 mg/kg, 20 mg/kg, 25 mg/kg, 30 mg/kg, 35 mg/kg, or 40 mg/kg. In some embodiments, the SAP polypeptide or SAP agonist is administered at a dose of about 0.1-0.3, 0.3-0.5, 0.5-0.8, 0.8-1, 1-5, 5-10, 10-15, 15-20, 20-25, 25-30, 30-35, or 35-40 mg/kg. The compound may be in a capsule and/or a unit dosage form described herein. In some embodiments, the compound is administered intravenously (IV). In some embodiments, the compound is administered by injection (e.g. SubQ, IM, IP), by inhalation or insufflation (either through the mouth or the nose) or the administration is oral, buccal, sublingual, transdermal, nasal, parenteral or rectal. In some embodiments, the SAP agonist, such as an SAP polypeptide, is administered by intravenous infusion. In certain embodiments, for each dose, infusion is over a period of approximately one hour. However, longer or shorter infusion periods may be used (e.g., 30 minutes, 40 minutes, 45 minutes, 50 minutes, 55 minutes, 1 hour ten minutes, 1 hour fifteen minutes, 90 minutes, and the like). When the method comprises administering an additional anti-cancer therapeutic, that therapeutic may be administered by the same route of administration or by a different route of administration. In certain embodiments, an additional anti-cancer therapeutic is administered orally.

Also provided herein are methods for ameliorating one or more signs or symptoms associated with myelofibrosis. For example, the treatment using the methods described herein is effective in reducing spleen size, ameliorating constitutional symptoms (such as early satiety, fatigue, night sweats, cough, and pruritus), reducing the MPN-SAF Total Symptom Score, reducing leukocytosis, reducing thrombocytosis, improving anemia, improving thrombocytopenia, improving leukopenia, reducing transfusion dependence, decreasing JAK2V617F allele burden, decrease in peripheral blood blasts, decrease in bone marrow blasts, reducing bone marrow fibrosis, improving pruritus, improving cachexia, and/or reducing or increasing bone marrow cellularity. The reduction, decrease, amelioration, or improvement can be at least by 5, 10, 20, 30, 40, 50, 60, 70, 80, or 90% compared to the level prior to commencing treatment with the methods provided herein. In some embodiments, bone marrow fibrosis is reduced in the subject after treatment. In some embodiments, bone marrow fibrosis becomes Grade 0 after treatment. In some embodiments, bone marrow fibrosis becomes Grade 1 after treatment. In some embodiment, the spleen becomes non-palpable in the subject after treatment. In some embodiments, the subject has complete resolution of leukocytosis and/or thrombocytosis after treatment. In some embodiments, the subject has complete resolution of anemia, thrombocytopenia, and/or leukopenia after treatment. In some embodiments, the subject becomes transfusion independent after treatment. In some embodiments, the subject has complete resolution of pruritus after treatment. In some embodiments, efficacy of the treatment will be assessed by evaluation of the overall response rate (ORR) categorized according to the International Working Group (IWG) criteria modified to include stable disease with improvement in bone marrow fibrosis by at least one grade as a response. In some embodiments, efficacy of the treatment will be assessed by evaluation of improvement in bone marrow fibrosis score by at least one grade according to the European Consensus on Grading of Bone Marrow Fibrosis. In some embodiments, efficacy of the treatment will be assessed by evaluating changes in levels of circulating plasma cytokine levels including but not limited to CRP, IL-1Ra, MIP-1β, TNFα, IL-6 and VEGF. In some embodiments, efficacy of the treatment will be assessed by evaluating changes in levels of PBMC mRNA and miRNA expression levels. In some embodiments, efficacy of the treatment will be assessed by lack of progression of PV or ET to myelofibrosis. In some embodiments, efficacy of the treatment will be assessed by lack of increase in bone marrow fibrosis by at least one grade.

In some embodiments, the treatment using the methods described herein (e.g. single agent or combination therapy using a SAP polypeptide or SAP agonist) is effective in reducing spleen volume by at least 20%, at least 25%, at least 30%, at least 35%, at least 40%, at least 45%, at least 50%, at least 55%, at least 60%, at least 65%, or at least 70% compared to the level prior to commencing treatment with the methods provided herein (e.g., compared to baseline). In some embodiments, the treatment is effective in reducing spleen volume by at least 25%. In some embodiments, the treatment is effective in reducing spleen volume by at least 50%. In some embodiments, the treatment is effective in reducing spleen volume by about 20-70%, about 20-60%, about 25-60%, about 25-55%, or about 25%-50%. In some embodiments, spleen volume may be measured by manual palpation. It would be understood by one of skill in the art that other known methods to measure spleen volume may also be employed, such as measurement by magnetic resonance imaging. In certain embodiments, the disclosure provides methods for decreasing spleen volume in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to decrease spleen volume by at least 25%, at least 30%, at least 35%, at least 40%, at least 50%, or at least 55%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, spleen volume is decreased by about 25-55%, by about 25-50%, or by about 25-40%.

In some embodiments, the treatment using the methods described herein (e.g. single agent or combination therapy using a SAP polypeptide or SAP agonist) is effective in reducing the Myeloproliferative Neoplasms Symptom Assessment Form (MPN-SAF) Total Symptom Score by at least 20%, at least 25%, at least 30%, at least 35%, at least 40%, at least 45%, at least 50%, at least 55%, at least 60%, at least 65%, or at least 70% compared to the score prior to commencing treatment with the methods provided herein. See Emanuel et al., 2012, Journal of Clinical Oncology, volume 30, number 33, pages 4098-4013, for a description and discussion of the myeloproliferative neoplasm symptom assessment form total symptom score. In some embodiments, the treatment is effective in reducing the MPN-SAF Total Symptom Score by at least 25%. In some embodiments, the treatment is effective in reducing the MPN-SAF Total Symptom Score by at least 50%. In some embodiments, the symptoms were assessed using the MPN-SAF patient reported outcome tool (Emanuel et al. 2012, Journal of Clinical Oncology 30(33): 4098-4103). In certain embodiments, the disclosure provides methods for reducing the MPN-SAF Total Symptom Score in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to reduce the MPN-SAF Total Symptom Score by at least about 25%, at least 30%, at least 35%, at least 40%, at least 50%, at least 55%, or at least 60%. In certain embodiments, the SAP agonist comprises an SAP polypeptide, such as a SAP polypeptide with glycosylation that differs from that of human SAP purified from serum, and the additional anti-cancer therapeutic is a JAK kinase inhibitor. In certain embodiments, the JAK kinase inhibitor is ruxolitinib. In certain embodiments, the MPN-SAF Total Symptom Score is reduced by about 25-60%, by about 25-55%, or by about 25-50%.

In some embodiments, the treatment using the methods described herein (e.g. single agent or combination therapy using a SAP polypeptide or SAP agonist) is effective in increasing hemoglobin levels by at least about 500 mg/L, 1 g/L, 2 g/L, 3 g/L, or 5 g/L compared to the level prior to commencing treatment with the methods provided herein (e.g., compared to baseline). In some embodiments, the treatment is effective in increasing hemoglobin levels by 500-1000 mg/L, 1-2 g/L, 2-3 g/L, or 3-5 g/L compared to the level prior to commencing treatment with the methods provided herein (e.g., compared to baseline). In some embodiments, the treatment is effective in increasing hemoglobin levels by 1 g/L. In some embodiments, the treatment is effective in increasing the hemoglobin levels to at least 80 g/L, at least 90 g/L, at least 100 g/L, at least 110 g/L, at least 120 g/L, at least 130 g/L, or at least 140 g/L. In some embodiments, the treatment is effective in increasing hemoglobin levels to at least 100 g/L. In some embodiments, the hemoglobin levels are measured as part of a routine Complete Blood Count (CBC). It would be understood by one of skill in the art that other known methods to measure hemoglobin levels may also be employed. In certain embodiments, the disclosure provides methods for increasing the hemoglobin levels in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to increase the hemoglobin levels by at least about 500 mg/L, 1 g/L, 2 g/L, 3 g/L, or 5 g/L. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, the hemoglobin levels are increased by about 500-1000 mg/L, 1-2 g/L, 2-3 g/L, or 3-5 g/L. In certain embodiments, the hemoglobin levels are increased to at least about 80 g/L, 90 g/L, 100 g/L, 110 g/L, 120 g/L, 130 g/L, or 140 g/L.

In some embodiments, the treatment using the methods described herein (e.g. single agent or combination therapy using a SAP polypeptide or SAP agonist) is effective in reducing red blood cell (RBC) transfusions by at least 20%, at least 25%, at least 30%, at least 35%, at least 40%, at least 45%, at least 50%, at least 55%, or at least 60% compared to the level prior to commencing treatment with the methods provided herein. In some embodiments, the treatment is effective in reducing RBC transfusions by at least 25%. In some embodiments, the treatment is effective in reducing RBC transfusions by at least 50%. In some embodiments, the treatment is effective in achieving RBC transfusion independence. In certain embodiments, the disclosure provides methods for reducing RBC transfusions in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to reduce RBC transfusions by at least about 25%, at least 30%, at least 35%, at least 40%, at least 50%, at least 55%, or at least 60%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, RBC transfusions are reduced by about 25-60%, by about 25-55%, or by about 25-50%. In certain embodiments, the patient becomes transfusion independent following treatment.

In some embodiments, the treatment using the methods described herein (e.g. single agent or combination therapy using a SAP polypeptide or SAP agonist) is effective in ameliorating thrombocytopenia when present. In some embodiments, the treatment increases platelets by at least 50%, at least 60%, at least 70%, at least 80%, at least 90%, or at least 100% compared to the level prior to commencing treatment with the methods provided herein. In some embodiments, the treatment increases platelets by at least 20%-30%, at least 30%-40%, at least 40%-50%, at least 50%-60%, at least 60%-70%, at least 70%-80%, at least 80%-90%, or at least 90%-100% compared to the level prior to commencing treatment with the methods provided herein. In some embodiments, the treatment is effective in increasing platelets by at least 100%. In some embodiments, the treatment increases platelets to at least $40 \times 10^9$/L, $50 \times 10^9$/L, $60 \times 10^9$/L, $70 \times 10^9$/L, $80 \times 10^9$/L, $90 \times 10^9$/L, or $100 \times 10^9$/L. In some embodiments, the treatment increases platelets to at least $50$-$75 \times 10^9$/L, $75$-$100 \times 10^9$/L, or $100$-$150 \times 10^9$/L. In some embodiments, the treatment increases platelets to $50 \times 10^9$/L. In some embodiments, the treatment increases platelets to $100 \times 10^9$/L. In some embodiments, platelets are measured as part of a routine Complete Blood Count (CBC). It would be understood by one of skill in the art that other known methods to measure platelets may also be employed. In certain embodiments, the disclosure provides methods for increasing platelets in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to increase platelets by at least 25%, at least 30%, at least 40%, at least 50%, at least 60%, at least 70%, at least 80%, at least 90%, or at least 100%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, platelets are increased by about 50%-60%, 60%-70%, 70%-80%, 80%-90%, or 90%-100%.

In some embodiments, the treatment using the methods described herein (e.g. single agent or combination therapy using a SAP polypeptide or SAP agonist) is effective at decreasing platelet transfusions by at least 25%, 30%, 40%, 50%, 60%, 75%, or 100% compared to the level prior to commencing treatment with the methods provided herein. In some embodiments, the treatment decreases platelet transfusions by at least 50%. In certain embodiments, the disclosure provides methods for decreasing platelet transfusions in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to decrease platelet transfusions by at least 30%, at least 40%, at least 50%, at least 60%, or at least 70%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, platelet transfusions are decreased by about 25%-40%, 25%-50%, 50%-70%, or 70%-100%.

In some embodiments, the treatment using the methods described herein (e.g. single agent or combination therapy using a SAP polypeptide or SAP agonist) is effective in ameliorating thrombocytosis when present. In some embodiments, the treatment decreases platelets by at least 10%, at least 15%, at least 20%, at least 25%, at least 30%, at least 35%, at least 40%, or at least 50% compared to the level prior to commencing treatment with the methods provided herein. In some embodiments, the treatment decreases platelets by 25%. In some embodiment, the treatment decreases platelets to the normal levels. In some embodiments, platelets are measured as part of a routine Complete Blood Count (CBC). It would be understood by one of skill in the art that other known methods to measure platelets may also be employed. In certain embodiments, the disclosure provides methods for decreasing platelets in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to decrease platelets by at least 10%, at least 15%, at least 20%, at least 25%, at least 30%, at least 35%, at least 40%, or at least 50%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, platelets are decreased by about 10%-15%, at least 15%-25%, or at least 25%-35%.

In some embodiments, the treatment using the methods described herein (e.g. single agent or combination therapy using a SAP polypeptide or SAP agonist) is effective in ameliorating neutropenia when present. In some embodiments, the treatment increases the absolute neutrophil count (ANC) by at least 25%, at least 30%, at least 40%, at least 50%, at least 60%, at least 70%, at least 80%, at least 90%, or at least 100% compared to the level prior to commencing treatment with the methods provided herein. In some embodiments, the treatment increases ANC by at least 20%-30%, at least 30%-40%, at least 40%-50%, at least 50%-60%, at least 60%-70%, at least 70%-80%, at least 80%-90%, or at least 90%-100% compared to the level prior to commencing treatment with the methods provided herein. In some embodiments, the treatment is effective in increasing ANC by at least 50%. In some embodiments, the treatment increases ANC to at least 1000 µL, at least 1250/µL, at least 1500/µL, at least 1750/µL, or at least 2000/µL. In some embodiments, the treatment increases ANC to at least 1250-1500/µL at least 1500-1750/µL, or at least 1750-2000/4. In some embodiments, the treatment increases ANC to at least 1500/µL. In some embodiments, ANC is measured as part of a routine Complete Blood Count (CBC). It would be understood by one of skill in the art that other known methods to measure ANC may also be employed. In certain embodiments, the disclosure provides methods for increasing ANC in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to increase ANC by at least 25%, at least 30%, at least 40%, at least 50%, at least 60%, at least 70%, at least 80%, at least 90%, or at least 100%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, ANC is increased by about 20%-30%, at least 30%-40%, at least 40%-50%, at least 50%-60%, at least 60%-70%, at least 70%-80%, at least 80%-90%, or at least 90%-100%.

In some embodiments, the treatment using the methods described herein (e.g. single agent or combination therapy using a SAP polypeptide or SAP agonist) is effective in ameliorating leukopenia when present. In some embodiments, the treatment increases the white blood cells (WBC) by at least 25%, at least 30%, at least 40%, at least 50%, at least 60%, at least 70%, at least 80%, at least 90%, or at least 100% compared to the level prior to commencing treatment with the methods provided herein. In some embodiments, the treatment increases WBC by at least 20%-30%, at least 30%-40%, at least 40%-50%, at least 50%-60%, at least 60%-70%, at least 70%-80%, at least 80%-90%, or at least 90%-100% compared to the level prior to commencing treatment with the methods provided herein. In some embodiments, the treatment is effective in increasing WBC by at least 50%. In some embodiments, the treatment increases WBC to at least $4 \times 10^9$/L, $5 \times 10^9$/L, $7.5 \times 10^9$/L, or $10 \times 10^9$/L. In some embodiments, the treatment increases WBC to $10 \times 10^9$/L. In some embodiments, the treatment increases WBC to the normal range. In some embodiments, WBC is measured as part of a routine Complete Blood Count (CBC). It would be understood by one of skill in the art that other known methods to measure WBC may also be employed. In certain embodiments, the disclosure provides methods for increasing WBC in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to increase WBC by at least 25%, at least 30%, at least 40%, at least 50%, at least 60%, at least 70%, at least 80%, at least 90%, or at least 100%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, WBC is increased by about 20%-30%, at least 30%-40%, at least 40%-50%, at least 50%-60%, at least 60%-70%, at least 70%-80%, at least 80%-90%, or at least 90%-100%.

In some embodiments, the treatment using the methods described herein (e.g. single agent or combination therapy using a SAP polypeptide or SAP agonist) is effective in ameliorating leukocytosis when present. In some embodiments, the treatment decreases ANC by at least 10%, at least 15%, at least 20%, at least 25%, at least 30%, at least 35%, at least 40%, at least 50%, at least 60%, or at least 70% compared to the level prior to commencing treatment with the methods provided herein, without decreasing ANC below 1500/μL. In some embodiments, the treatment decreases ANC by 25%. In some embodiments, the treatment decreases ANC by 50%. In some embodiments, the treatment decreases ANC to normal levels. In some embodiments, the treatment decreases white blood cells (WBC) by at least 10%, at least 15%, at least 20%, at least 25%, at least 30%, at least 35%, at least 40%, at least 50%, at least 60%, or at least 70% compared to the level prior to commencing treatment with the methods provided herein, without decreasing WBC below the lower limit of normal. In some embodiments, the treatment decreases WBC by 25%. In some embodiments, the treatment decreases WBC by 50%. In some embodiments, the treatment decreases WBC to <35×10$^9$/L, <30×10$^9$/L, <25×10$^9$/L, <20×10$^9$/L, or <15×10$^9$/L. In some embodiments, the treatment decreases WBC to <25×10$^9$/L. In some embodiments, the treatment decreases WBC to the normal range. In some embodiments, ANC and WBC are measured as part of a routine Complete Blood Count (CBC). It would be understood by one of skill in the art that other known methods to measure ANC or WBC may also be employed. In certain embodiments, the disclosure provides methods for decreasing ANC or WBC in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to decrease ANC or WBC by at least 10%, at least 15%, at least 20%, at least 25%, at least 30%, at least 35%, at least 40%, at least 50%, at least 60%, or at least 70% without decreasing WBC below the lower limit of normal. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, ANC or WBC is decreased by about 20%-30%, at least 30%-40%, at least 40%-50%, at least 50%-60%, or at least 60%-70% without decreasing WBC below the lower limit of normal.

In some embodiments, the treatment using the methods described herein (e.g. single agent or combination therapy using a SAP polypeptide or SAP agonist) is effective in decreasing peripheral blood blasts by at least 20%, at least 25%, at least 30%, at least 35%, at least 40%, at least 45%, at least 50%, at least 55%, at least 60%, or at least 70% compared to the level prior to commencing treatment with the methods provided herein. In some embodiments, the treatment is effective in decreasing peripheral blood blasts by at least 50%. In some embodiments, the treatment is effective in decreasing peripheral blood blasts from ≥1 to <1. It would be understood by one of skill in the art that any of the methods known in the art to measure peripheral blood blasts may be employed. In certain embodiments, the disclosure provides methods for decreasing peripheral blood blasts in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to decrease peripheral blood blasts by at least 20%, at least 25%, at least 30%, at least 35%, at least 40%, at least 45%, at least 50%, at least 55%, at least 60%, or at least 70%. In certain embodiments, the SAP agonist comprises an SAP polypeptide, such as a SAP polypeptide with glycosylation that differs from that of human SAP purified from serum, and the additional anti-cancer therapeutic is a JAK kinase inhibitor. In certain embodiments, the JAK kinase inhibitor is ruxolitinib. In certain embodiments, peripheral blood blasts are decreased by about 20%-30%, at least 30%-40%, at least 40%-50%, at least 50%-60%, or at least 60%-70%. In certain embodiments, peripheral blood blasts are decreased from ≥1 to <1.

In some embodiments, the treatment using the methods described herein (e.g. single agent or combination therapy using a SAP polypeptide or SAP agonist) is effective in decreasing bone marrow fibrosis from Grade 3 to Grade 2 (e.g. single agent or combination therapy using a SAP polypeptide or SAP agonist). In some embodiments, the treatment is effective in decreasing bone marrow fibrosis from Grade 3 to Grade 1. In some embodiments, the treatment is effective in decreasing bone marrow fibrosis from Grade 3 to Grade 0. In some embodiments, the treatment is effective in decreasing bone marrow fibrosis from Grade 2 to Grade 1. In some embodiments, the treatment is effective in decreasing bone marrow fibrosis from Grade 2 to Grade 0. In some embodiments, the treatment is effective in decreasing bone marrow fibrosis by at least by 5, 10, 20, 30, 40, 50, 60, 70, 80, or 90% compared to the level prior to commencing treatment with the methods provided herein. It would be understood by one of skill in the art that any of the methods known in the art to evaluate bone marrow fibrosis may be employed. In certain embodiments, the disclosure provides methods for decreasing bone marrow fibrosis in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to decrease bone marrow fibrosis by at least 5, 10, 20, 30, 40, 50, 60, 70, 80, or 90%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, bone marrow fibrosis is decreased by about 20%-30%, at least 30%-40%, at least 40%-50%, at least 50%-60%, or at least 60%-70%.

In some embodiments, the treatment using the methods described herein (e.g. single agent or combination therapy using a SAP polypeptide or SAP agonist) is effective in decreasing bone marrow blasts from ≥5% to <5%. It would be understood by one of skill in the art that any of the methods known in the art to measure bone marrow blasts be employed. In certain embodiments, the disclosure provides methods for decreasing bone marrow blasts in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to decrease bone marrow blasts by at least 20%, at least 25%, at least 30%, at least 35%, at least 40%, at least 45%, at least 50%, at least 55%, at least 60%, or at least 70%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, bone marrow blasts are decreased by about 20%-30%, at least 30%-40%, at least 40%-50%, at least 50%-60%, or at least 60%-70%.

In some embodiments, the treatment is effective in improving bone marrow cellularity. The improvement can be at least by 20, 30, 40, 50, 60, or 70% compared to the level prior to commencing treatment with the methods provided herein. In certain embodiments, the disclosure provides methods for improving bone marrow cellularity in a patient in need thereof, wherein the patient in need thereof has myelofibrosis, comprising administering an amount of an SAP agonist, such as an SAP polypeptide, alone or in combination with an additional anti-cancer therapeutic (e.g., a JAK kinase inhibitor) according to a dosing schedule effective to improve bone marrow cellularity by at least 20%, at least 25%, at least 30%, at least 35%, at least 40%, at least 45%, at least 50%, at least 55%, at least 60%, or at least 70%. In certain embodiments, the SAP agonist comprises an SAP polypeptide, such as a SAP polypeptide with glycosylation that differs from that of human SAP purified from serum, and the additional anticancer therapeutic is a JAK kinase inhibitor. In certain embodiments, the JAK kinase inhibitor is ruxolitinib. In certain embodiments, bone marrow cellularity is improved by about 20%-30%, at least 30%-40%, at least 40%-50%, at least 50%-60%, or at least 60%-70%.

In certain embodiments, the treatment using the methods described herein (e.g. single agent or combination therapy using a SAP polypeptide or SAP agonist) results in at least one of the effects described herein (e.g. reduction in spleen volume, reduction in MPN-SAF Total Symptom Score, increase in hemoglobin, reduction in RBC transfusions, improvement in thrombocytopenia, decrease in platelet transfusions, improvement in thrombocytosis, improvement in neutropenia, improvement in leukocytosis, decrease in peripheral blood blasts, decrease in bone marrow fibrosis, decrease in bone marrow blasts or improvement in bone marrow cellularity). In some embodiments, the treatment using the methods described herein results in at least two of the effects described herein. In some embodiments, the treatment using the methods described above results in at least three, four, five, six, seven, eight, nine, or ten of the effects described herein. In certain embodiments of any of the foregoing, evaluation of whether a particular degree of improvement of a symptom or therapeutic effect has been achieved is evaluated at one or more points over time, such as following at least 12, 18, 20, or at least 24 weeks of treatment, or following greater than 24 weeks of treatment.

In some embodiments, treatment using one or more of the methods described herein (e.g. single agent or combination therapy using a SAP polypeptide or SAP agonist of the disclosure) results in at least one of the effects described herein (e.g. reduction in spleen volume, reduction in MPN-SAF Total Symptom Score, increase in hemoglobin, reduction in RBC transfusions, achievement of transfusion independence, improvement in thrombocytopenia, decrease in platelet transfusions, improvement in thrombocytosis, improvement in neutropenia, improvement in leukocytosis, decrease in peripheral blood blasts, decrease in bone marrow fibrosis, decrease in bone marrow blasts or improvement in bone marrow cellularity), without causing or inducing clinically significant myelosuppression. In some embodiments, treatment using one or more of the methods described herein results in at least two of the effects described herein, without causing or inducing clinically significant myelosuppression. In some embodiments, treatment using one or more of the methods described above results in at least three, four, five, six, seven, eight, nine, or ten of the effects described herein, without causing or inducing clinically significant myelosuppression. In some embodiments, treatment using one or more of the methods described herein results in no myelosuppression. It certain embodiments, any of the foregoing methods comprise administering SAP comprising an SAP polypeptide having glycosylation that differs from that of SAP purified from human serum, such as recombinant human SAP (e.g., recombinant human pentraxin-2 produced in CHO cells). In certain embodiments, any of the foregoing methods comprise administering the SAP agonist or SAP polypeptide according to a dosing schedule, wherein any of the foregoing therapeutic effects are achieved following administration according to the dosing schedule. In certain embodiments, one or more of the foregoing therapeutic effects are achieved following administration according to a dosing schedule (e.g., administering comprises administering according to a dosing schedule). Improvement in any of the foregoing parameters (e.g., reduction in symptoms) is evaluated at one or more time points during treatment, for example, following at least 12, at least 18, at least 20, at least 24, or greater than 24 weeks of treatment.

For any of the foregoing examples of improvement in a patient, such as an improvement in one or more symptoms, in certain embodiments, the disclosure provides that the treatment comprises administering a SAP agonist or SAP polypeptide at a dose and on a dosing schedule effective to have the therapeutic effect. In certain embodiments, that dose and dosing schedule also decreases one or more side effects experienced with another anti-cancer therapy.

In other embodiments, the treatment improves, instead of or in addition to, one or more other symptoms of a fibrotic cancer. In certain embodiments, treatment decrease pain, decreases tumor size, decreases weight loss, improves weight gain, increases progression free survival, or otherwise improves the quality of life of the patient.

In some embodiments, the SAP polypeptide or SAP agonist is administered to the subject at a dosing schedule comprising administration of the SAP polypeptide or SAP agonist at least once a week for at least 1 cycle, at least 2 cycles, at least 3 cycles, at least 4 cycles, at least 5 cycles, at least 6 cycles, at least 7 cycles or at least 8 cycles of a 28-day cycle. In some embodiments, the SAP polypeptide or SAP agonist is administered to the subject at least once a week for at least 6 cycles of a 28-day cycle, at least 8 cycles of a 28-day cycle, at least 10 cycles of a 28-day cycle, at least 12 cycles of a 28-day cycle, at least 15 cycles of a 28-day cycle, at least 18 cycles of a 28-day cycle, or at least 24 cycles of a 28-day cycle. In some embodiments, the compound is administered to the subject once a week for at least one month, at least two months, at least three months, at least four months, at least five months, at least six months, at least eight months, at least one year, or at least two years. In further embodiments, the compound is administered every other day in the first week of treatment. In some embodiments, the SAP polypeptide or SAP agonist is administered at a dosing schedule comprising administration of the SAP polypeptide or SAP agonist every 4 weeks for at least 1 cycle, at least 2 cycles, at least 3 cycles, at least 4 cycles, at least 5 cycles, at least 6 cycles, at least 7 cycles or at least 8 cycles of a 28-day or 4-week cycle. In some embodiments, the SAP polypeptide or SAP agonist is administered to the subject once every 4 weeks for at least 6 cycles of a 28-day cycle, at least 8 cycles of a 28-day cycle, at least 10 cycles of a 28-day cycle, at least 12 cycles of a 28-day cycle, at least 15 cycles of a 28-day cycle, at least 18 cycles of a 28-day cycle, or at least 24 cycles of a 28-day cycle. In some embodiments, the compound is administered to the subject once every 4 weeks for at least one month, at least two months, at least three months, at least four months, at least five months, at least six months, at least eight months, at least one year, or at least two years, and possibly administered chronically over the life of the patient. In a further embodiment, the SAP polypeptide or SAP agonist is administered every other day in the first week of treatment. In some embodiments, the SAP polypeptide or SAP agonist is administered several days (e.g. days 1, 3 and 5) every 4 weeks for at least 6 cycles of a 28-day cycle, at least 8 cycles of a 28-day cycle, at least 10 cycles of a 28-day cycle, at least 12 cycles of a 28-day cycle, at least 15 cycles of a 28-day cycle, at least 18 cycles of a 28-day cycle, or at least 24 cycles of a 28-day cycle. In some embodiments, the compound is administered to the subject for several days (eg days 1, 3, 5) every 4 weeks for at least one month, at least two months, at least three months, at least four months, at least five months, at least six months, at least eight months, at least one year, or at least two years, and possibly administered chronically over the life of the patient. In certain embodiments, the dosing schedule results in at least one of the effects (e.g., improvement in one or more symptoms or parameters) described herein (e.g. reduction in spleen volume, reduction in MPN-SAF Total Symptom Score, increase in hemoglobin, reduction in RBC transfusions, achievement of transfusion independence, improvement in thrombocytopenia, decrease in platelet transfusions, improvement in thrombocytosis, improvement in neutropenia, improvement in leukocytosis, decrease in peripheral blood blasts, decrease in bone marrow fibrosis, decrease in bone marrow blasts or improvement in bone marrow cellularity). In some embodiments, the dosing schedule results in at least two of the effects described herein. In some embodiments, the dosing schedule results in at least three, four, five, six, seven, eight, nine, or ten of the effects described herein. In certain embodiments, the SAP agonist comprises recombinant human SAP.

In certain embodiments, the disclosure provides methods for administering an amount of an SAP agonist, such as an SAP polypeptide, alone or in combination with an additional anti-cancer therapeutic (e.g., a JAK kinase inhibitor or a chemotherapeutic) according to a dosing schedule comprising administering an SAP polypeptide or SAP agonist using a dosage regimen comprising administering 10 mg/kg of a SAP polypeptide, such as a SAP polypeptide with glycosylation that differs from that of human SAP purified from serum, on days 1, 3, 5, 8, 15, and 22 of Cycle 1 and Days 1, 8, 15 and 22 of each subsequent 28 day cycle. In certain embodiments, the SAP agonist comprises an SAP polypeptide and the additional anticancer therapeutic is a JAK kinase inhibitor. In certain embodiments, the JAK kinase inhibitor is ruxolitinib.

In certain embodiments, the disclosure provides methods for administering an amount of an SAP agonist, such as an SAP polypeptide, alone or in combination with an additional anti-cancer therapeutic (e.g., a JAK kinase inhibitor) according to a dosing schedule comprising administering an SAP polypeptide or SAP agonist using a dosage regimen comprising administering 10 mg/kg of an SAP polypeptide or SAP agonist on Days 1, 3, and 5 of Cycle 1 and Day 1 of each subsequent 28 day cycle. In certain embodiments, the SAP agonist comprises an SAP polypeptide and the additional anticancer therapeutic is a JAK kinase inhibitor. In certain embodiments, the JAK kinase inhibitor is ruxolitinib In some embodiments, the SAP polypeptide or SAP agonist is administered multiple times during the first week (e.g. days 1, 3 and 5), followed by administration every week, every two weeks, every three weeks, or every 4 weeks. In some embodiments, the SAP agonist is administered multiple times a week every other week, every three weeks, every month, every other month, every three months, every six months, or as needed. In some embodiments, the SAP polypeptide or SAP agonist is administered by IV infusion. In some embodiments, the SAP polypeptide or SAP agonist is administered at a dose of 10 mg/kg. In some embodiments, the SAP polypeptide or SAP agonist is administered at any of the dosages described herein. In some embodiments, the SAP polypeptide or SAP agonist is administered in combination with an anti-cancer therapy. In some embodiments, the subject has been on a stable dose of the anti-cancer therapy for at least 6 months, at least 5 months, at least 4 months, at least 3 months, at least 2 months, at least 1 month, at least 3 weeks, or at least 2 weeks. In some embodiments, the subject has been on a stable dose of anti-cancer therapy for at least 3 months. In some embodiments, the subject does not show any improvement in one or more symptoms for at least 2 weeks, at least 3 weeks, at least 1 month, at least 2 months, at least 3 months, at least 4 months, at least 5 months, at least 6 months when treated with the anti-cancer therapy. In some embodiments, the anti-cancer therapy is a JAK kinase inhibitor as described herein. In some embodiments, the JAK kinase inhibitor is ruxolitinib. In some embodiments, the anti-cancer therapy is administered at a dose previously determined to be effective. In some embodiments, the dosage regimens described herein are adjusted as needed to achieve one of the treatment outcomes described herein.

In some embodiments, the methods disclosed herein comprise administering one or more additional doses of the SAP polypeptide or SAP agonist after achieving an initial response. In some embodiments, a subsequent response is achieved following the administration of one or more additional doses of the SAP polypeptide or SAP agonist after achieving an initial response in a subject. A subsequent response may be an additional response (e.g. any of the responses described herein not initially observed), the maintenance of the initial response, or an improvement upon the initial response. In some embodiments, the administration of one or more additional doses substantially maintains the initial response. In some embodiments, the administration of one or more additional doses provides further improvement relative to the initial response. In some embodiments, the administration of one or more additional doses provides one or more additional responses that were not initially observed. In certain embodiments, the SAP agonist comprises an SAP polypeptide, such as recombinant human SAP.

In some embodiments, upon administration of an SAP polypeptide or SAP agonist or a pharmaceutically acceptable salt thereof to a subject such as human subject, the C. (maximum drug concentration) of the compound is achieved within about 0.5 to about 5 hours, about 1.5 to about 4.5 hours, about 2 to about 4 hours, or about 2.5 to about 3.5 hours post-dose. In some embodiments, upon administration of the compound to a human subject, the elimination half life of the compound is about 11 to 110 hours, 20-72 hours, 12 to about 40 hours, about 16 to about 34 hours, or about 20 to about 40 hours. In some embodiments, the mean AUC of the compound increases more than proportionally with increasing doses ranging from about 0.1 mg to about 40 mg per kg. In some embodiments, the accumulation of the compound is about 1.1 to about 5 fold, about 1.25 to about 4.0 fold, about 1.5 to about 3.5 fold, about 2 to about 3 fold at steady state when the compound is dosed once weekly. In some embodiments, the compound does not accumulate when dosed weekly.

The disclosure also provides kits for treating fibrotic cancers or cancer-associated fibrosis that comprise one or more SAP polypeptides or SAP agonists. In some embodiments, the kit may include an anti-cancer therapeutic as described herein to be administered conjointly with one or more SAP polypeptides or SAP agonists. The SAP polypeptides or SAP agonists and anti-cancer therapeutic agents may be formulated to be administered conjointly. The active agents of the kit may be administered separately or in a combination formulation. The active agents may be administered simultaneously or at different dosing schedules. In certain embodiments of any of the foregoing, the SAP agonist comprises recombinant human SAP.

Pharmaceutical Preparations and Formulations

In certain embodiments, the methods described herein involve administration of at least one SAP agonist (e.g. a variant SAP polypeptide) of the invention to a subject as a therapeutic agent. The therapeutic agents of the invention may be formulated in a conventional manner using one or more physiologically acceptable carriers or excipients. For example, therapeutic agents and their physiologically acceptable salts and solvates may be formulated for administration by, for example, intravenous infusion (IV), injection (e.g. SubQ, IM, IP), inhalation or insufflation (either through the mouth or the nose) or oral, buccal, sublingual, transdermal, nasal, parenteral or rectal administration. In certain embodiments, therapeutic agents may be administered locally, at the site where the target cells are present, i.e., in a specific tissue, organ, or fluid (e.g., blood, cerebrospinal fluid, tumor mass, etc.).

The present invention further provides use of any SAP polypeptide or SAP agonist of the invention in the manufacture of a medicament for the treatment or prevention of a disorder or a condition, as described herein, in a patient, for example, the use of an SAP polypeptide or SAP agonist in the manufacture of medicament for the treatment of a disorder or condition described herein. In some aspects, an SAP polypeptide or SAP agonist of the invention may be used to make a pharmaceutical preparation for the use in treating or preventing a disease or condition described herein Therapeutic agents can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included. In some embodiments, the therapeutic agents can be administered to cells by a variety of methods know to those familiar in the art, including, but not restricted to, encapsulation in liposomes, by iontophoresis, or by incorporation into other vehicles, such as hydrogels, cyclodextrins, biodegradable nanocapsules, and bioadhesive microspheres.

For oral administration, the pharmaceutical compositions may take the form of, for example, tablets, lozenges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), therapeutic agents may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

In the methods of the invention, the pharmaceutical compounds can also be administered by intranasal or intrabronchial routes including insufflation, powders, and aerosol formulations (for examples of steroid inhalants, see Rohatagi (1995) J. Clin. Pharmacol. 35:1187-1193; Tjwa (1995) Ann. Allergy Asthma Immunol. 75:107-111). For example, aerosol formulations can be placed into pressurized acceptable propellants, such as dichlorodifluoromethane, propane, nitrogen, and the like. They also may be formulated as pharmaceuticals for non-pressured preparations such as in a nebulizer or an atomizer. Typically, such administration is in an aqueous pharmacologically acceptable buffer.

Pharmaceutical compositions suitable for respiratory delivery (e.g., intranasal, inhalation, etc.) of SAP polypeptides or SAP agonists may be prepared in either solid or liquid form.

SAP polypeptides or SAP agonists of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition, SAP polypeptides or SAP agonists of the invention may also be formulated as a depot preparation. Such long-acting formulations may be administered by implantation (for example subcutaneously or intramuscularly) or by intramuscular injection. Thus, for example, therapeutic agents may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the blood-brain-barrier in an attempt to exploit one of the endogenous transport pathways of the blood-brain-barrier); pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

In certain embodiments, SAP polypeptides or SAP agonists of the invention are incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Pharmaceutical compositions (including cosmetic preparations) may comprise from about 0.00001 to 100% such as from 0.001 to 10% or from 0.1% to 5% by weight of one or more of the SAP polypeptides or SAP agonists described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of therapeutic agents, or by insertion of a sustained release device that releases therapeutic agents. SAP polypeptides or SAP agonists of the invention may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, conjunctiva, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds may be injected directly into the vitreous and aqueous humour. In a further alternative, the compounds may be administered systemically, such as by intravenous infusion or injection, for treatment of the eye.

Therapeutic agents described herein may be stored in oxygen-free environment according to methods in the art.

Exemplary compositions comprise an SAP polypeptide or SAP agonist with one or more pharmaceutically acceptable carriers and, optionally, other therapeutic ingredients. The carrier(s) must be "pharmaceutically acceptable" in the sense of being compatible with the other ingredients of the composition and not eliciting an unacceptable deleterious effect in the subject. Such carriers are described herein or are otherwise well known to those skilled in the art of pharmacology. In some embodiments, the pharmaceutical compositions are pyrogen-free and are suitable for administration to a human patient. In some embodiments, the pharmaceutical compositions are irritant-free and are suitable for administration to a human patient. In some embodiments, the pharmaceutical compositions are allergen-free and are suitable for administration to a human patient. The compositions may be prepared by any of the methods well known in the art of pharmacy.

In some embodiments, an SAP polypeptide or SAP agonist is administered in a time release formulation, for example in a composition which includes a slow release polymer. An SAP polypeptide or SAP agonist can be prepared with carriers that will protect against rapid release. Examples include a controlled release vehicle, such as a polymer, microencapsulated delivery system, or bioadhesive gel. Alternatively, prolonged delivery of an SAP polypeptide or SAP agonist may be achieved by including in the composition agents that delay absorption, for example, aluminum monostearate hydrogels and gelatin.

Methods for delivering nucleic acid compounds are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized for the delivery of virtually any nucleic acid compound. Nucleic acid compounds can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXEMPLIFICATION

Example 1

Treatment of Myelofibrosis with α2,3-Sialic Acid-Containing Sap Alone and in Combination with Ruxolitinib: Stage 1 Results at 12 Weeks Recombinant human SAP, in this case the recombinant human SAP known as PRM-151, was administered to myelofibrosis (MF) patients, alone and in combination with ruxolitinib (RUX), to evaluate safety and efficacy in treating bone marrow fibrosis (BMF). Patients with Intermediate-1, Intermediate-2, or high risk MF with grade ≥2 BMF, either not receiving therapy or on a stable dose of RUX, were eligible for this study.

Twenty-seven patients were assigned to one of four cohorts based on administration of PRM-151 as a monotherapy or as part of a combination therapy. Cohort 1: i) patients who received no treatment for MF in at least two weeks, ii) were administered an initial loading dose of SAP at 10 mg/kg by intravenous infusion (~1 hour infusion) on days 1, 3, and 5, and iii) thereafter were administered a dose of SAP every four weeks at 10 mg/kg by intravenous infusion (~1 hour infusion). Cohort 2: i) patients who received no treatment for MF in at least two weeks, ii) were administered an initial loading dose of SAP at 10 mg/kg by intravenous infusion (~1 hour infusion) on days 1, 3, and 5, and iii) thereafter were administered a dose of SAP every week at 10 mg/kg by intravenous infusion (~1 hour infusion). Cohort 3: i) patients on a stable dose (e.g., on ruxolitinib for at least 3 months without any dose modifications) of ruxolitinib for at least 12 weeks with no improvement in spleen during the last four weeks, ii) were administered an initial loading dose of SAP at 10 mg/kg by intravenous infusion (~1 hour infusion) on days 1, 3, and 5 iii) thereafter were administered a dose of SAP every week at 10 mg/kg by intravenous infusion (~1 hour infusion), and iv) were administered RUX orally at the dose at which they entered the study. Cohort 4: i) patients on a stable dose (e.g., on ruxolitinib for at least 3 months without any dose modifications) of ruxolitinib for at least 12 weeks with no improvement in spleen during the last four weeks, ii) were administered an initial loading dose of SAP at 10 mg/kg by intravenous infusion (~1 hour infusion) on days 1, 3, and 5 iii) thereafter were administered a dose of SAP every four weeks at 10 mg/kg by intravenous infusion (~1 hour infusion), and iv) were administered RUX orally at the dose at which they entered the study.

Patients in each cohort were monitored for improvements in BMF and other MF-related complications including, for example, abnormal blood cell parameters, splenomegaly, and symptoms as assessed by the MPN-SAF. In particular, patients were monitored for overall response rate according to the International Working Group consensus criteria for treatment response in myelofibrosis with myeloid metaplasia (Tefferi A, Cervantes F, Mesa R, et al. Revised response criteria for myelofibrosis: International Working Group-Myeloproliferative Neoplasms Research and Treatment (IWG-MRT) and European LeukemiaNet (ELN) consensus report. Blood. 2013; 122:1395-1398). Patients were also monitored for incidence of adverse events, changes in bone marrow fibrosis according to the European Consensus of Grading Bone Marrow Fibrosis (Thiele J, Kvasnicka H M, Facchetti F, et al. European consensus on grading bone marrow fibrosis and assessment of cellularity. *Haematologica* 2005; 90:1128-1132.), changes in the modified Myeloproliferative Neoplasma Symptom Assessment Form (MPN-SAF) Score (Emanuel et al. 2012, Journal of Clinical Oncology 30(33): 4098-4103), as well as pharmacokinetic parameters including, for example, maximum drug concentration (Cmax), time to maximum concentration (Tmax), area under the curve (AUC), clearance, and volume of distribution.

After 24 weeks of therapy, there was no apparent treatment-related myelosuppression, and Grade ≥2 adverse events occurring in ≥2 subjects, regardless of relatedness, are listed below in Table 1. The numbers indicated in each column below the grade indicate the number of patients in which the adverse event was reported. A blank cell indicates that the adverse event was not observed in any of the subjects in that cohort.

TABLE 1

| | Cohort 2 | | | Cohort 1 | | | Cohort 3 | | | Cohort 4 | | |
| | | | | | Grade | | | | | | | |
| Adverse Event | Gr 2 | Gr 3 | Gr 4 | Gr 2 | Gr 3 | Gr4 | Gr 2 | Gr 3 | Gr4 | Gr 2 | Gr 3 | Gr4 |
| Anemia | | | | | | | | 1 | | 1 | 1 | |
| Fatigue | | | | 2 | | | | | | 2 | | |
| Neuropathy Peripheral | | | | 1 | | | | 1 | | | | |
| Upper Respiratory Infection | | | | | | | | 1 | | 2 | | |
| Alanine aminotransferase increased | 1 | | | | | | | | | | 1 | |
| Abdominal pain | | 1 | | | 1 | | | | | | | |

Bone marrow biopsies were obtained at baseline and after three months of therapy and were reviewed. Improvement in BMF was observed in 5 of 27 subjects examined. Specifically, one patient treated with SAP weekly (a Cohort 2 patient) was observed to have an improvement from Grade 3 to Grade 2 after 12 weeks of treatment, one patient treated with SAP every four weeks (a Cohort 1 patient) was observed to have an improvement from Grade 2 to Grade 0 after 12 weeks of treatment, one patient treated with SAP every 4 weeks in addition to ruxolitinib (a Cohort 4 patient) with 11 prior bone marrow biopsies showing Grade 3 fibrosis was observed to have an improvement from Grade 3 to Grade 1 at 12 weeks and Grade 2 at 24 weeks, and one patient treated with SAP every 4 weeks in addition to ruxolitinib (a Cohort 4 patient) was observed to have an improvement from Grade 3 to Grade 2 at 12 weeks and improvement from Grade 2 to Grade 1 at 24 weeks. Accordingly, MF patients have demonstrated good tolerability to SAP, both alone and in combination with RUX. The data further indicates that administration of recombinant human SAP, both as a monotherapy and as a co-therapy with RUX, can be used to improve BMF in MF patients. As detailed below, these improvements in BMF have borne out upon further analysis of the data across further treatment periods. These results support not only the use of SAP in decreasing bone marrow fibrosis in MF, but also provide more general support for the use of SAP in decreasing fibrosis and restoring normal tissue function in other fibrotic cancers.

Not only was the combination therapy efficacious, but it may be suitable for patients for whom the benefits of the additional anti-cancer therapeutic alone had begun to wane. In addition, the combination therapy also resulted in improvement in some of the side effects often experienced in patients treated with the anti-cancer therapeutic alone. In this case, for patients who were being treated with ruxolitinib (a Janus kinase inhibitor) alone prior to addition of SAP to their therapeutic regimen, we observed improvements in anemia and thrombocytopenia, as assessed by increased hemoglobin levels and platelet counts, relative to those side effects experienced in those patients prior to addition of SAP (e.g., relative to treatment with Janus kinase inhibitor alone). Representative data is shown in Example 3. We also observed improvements in symptom scores and spleen size in patients on SAP and ruxolitinib compared to their status on ruxolitinib alone. These results not only demonstrate efficacy of SAP as a monotherapy or as a combination therapy for a fibrotic cancer, but also the use of SAP to expand the therapeutic window and patient population for other therapeutics, to provide treatment modalities for patients and subpopulations of patients for whom available treatments failed or are inadequate, and to improve the safety profile of available therapies while itself having therapeutic efficacy.

Example 2

Treatment of Myelofibrosis with Prm-151 Alone and in Combination with Ruxolitinib: Stage 1 Results at 24 Weeks Demographic data for the 27 patients enrolled in the four treatment arms of the study described above in Example 1 is summarized in Table 2 below. The patients enrolled in the study included those with primary myelofibrosis (PMF), post polycythemia vera myelofibrosis (Post-PV MF) or post essential thrombocythemia myelofibrosis (Post-ET MF), classified as Intermediate-1, Intermediate-2, or high risk MF according to the Dynamic International Prognostic Scoring System (DIPSS). 15 of the 27 patients had been treated with a JAK inhibitor prior to the current study. Of the 27 patients who enrolled in the study and started treatment, 18 patients completed 24 weeks and evaluation was ongoing for 3 patients who had not reached the 24-week mark. Patient cohorts are as described above.

TABLE 2

| Demographic Info | PRM-151 QW (Cohort 2) | PRM-151 Q4W (Cohort 1) | PRM-151 QW + RUX (Cohort 3) | PRM-151 Q4W + RUX (Cohort 4) |
|---|---|---|---|---|
| N | 8 | 7 | 6 | 6 |
| Median Age, years | 62 | 71 | 68 | 65.5 |
| (range) | (51-85) | (60-78) | (52-72) | (57-78) |
| Gender (M, F) | 3M, 5F | 5M, 2F | 3M, 3F | 1M, 5F |
| Median years since | 1.25 | 6.4 | 2.8 | 4.7 |
| Diagnosis (range) | (0-3) | (1-11) | (1-8) | (1-9) |
| DIPPS Stage | | | | |
| Intermediate-1, n | 3 | 2 | 2 | 1 |
| Intermediate-2, n | 5 | 4 | 2 | 5 |
| High, n | 0 | 1 | 2 | 0 |
| Type of MF | | | | |
| PMF, n | 6 | 3 | 3 | 2 |
| post-PV MF, n | 1 | 2 | 3 | 3 |
| post-ET MF, n | 1 | 2 | 0 | 1 |
| Fibrosis grade | | | | |
| Grade 2, n | 3 | 3 | 1 | 1 |
| Grade 3, n | 5 | 4 | 5 | 5 |
| Prior JAK inhibitor | 5 | 4 | 3 | 2 |
| Hgb < 100 g/L (n) | 4 | 5 | 3 | 3 |
| Platelets < 50 × $10^9$/L (n) | 2 | 5 | 1 | 2 |
| Median spleen, cm | 21 | 14.5 | 12.5 | 16 |
| (range) | (0-30) | (0-24) | (0-20) | (0-23) |

Clinical response assessment, including assessment of spleen size, MPN-SAF, and CBC, was carried out every 4 weeks. BM biopsies were carried out at baseline, 12 weeks, and 24 weeks. The IWG-MRT symptom and bone marrow responses observed at 24 weeks of this study are summarized below in Table 3. One or more IWG-MRT symptom responses occurred in each of the four treatment arms, with a total of 5 confirmed IWG-MRT symptom responses as of the date of this 24 week analysis. We note that the magnitude of the response required to score the response as confirmed IWG-MRT is very high (50% reduction in symptoms score lasting at least 12 weeks), and 6 additional patients achieved improvement in one or more parameters that was meaningful but did not achieve this particular threshold. Even despite the high threshold set in this experiment, the response rate is consistent with that achieved for other cancer therapeutics and is indicative of therapeutic efficacy across a clinically meaningful percentage of patients. In addition, all of the patients evaluated had significant disease at the time of treatment and all but two had already been exposed to and failed at least one prior therapy. In this context, the level of responsiveness achieved is particularly noteworthy.

In five patients, reductions in bone marrow fibrosis by ≥1 grade were observed. One or more bone marrow responses, i.e., decrease of at least 1 grade in bone marrow fibrosis, was observed in three out of the four treatment arms. For example, 2 bone marrow responses each were seen in the group treated with recombinant human SAP every four weeks (Cohort 1) and in the group treated with recombinant human SAP every 4 weeks in addition to ruxolitinib (Cohort 4). A ≥20% reduction in spleen volume was observed in five patients, with one 50% reduction lasting 8 weeks in the group treated weekly with recombinant human SAP (Cohort 2).

TABLE 3

| Treatment Arm | Response |
| --- | --- |
| Cohort 2 | 2 confirmed symptom responses (≥12 weeks) |
| | 1 symptom response ≥8 weeks |
| | 1 spleen response ≥8 weeks |
| | 1 bone marrow response |
| Cohort 1 | 2 bone marrow responses |
| | 1 symptom response ≥8 weeks |
| Cohort 3 | 1 confirmed symptom response (≥12 weeks) |
| Cohort 4 | 2 confirmed symptom responses (≥12 weeks) |
| | 2 confirmed bone marrow responses (≥12 weeks) |

Stage 1: 27 Patients; Criteria for Moving to Stage 2 = ≥1 response

FIG. 1 shows the percentage change in spleen size in subjects with palpable spleen who were followed to C6D29 (Cycle 6, Day 29) or beyond. Most of the evaluated patients (10 out of 13 patients, from all four treatment arms) showed a reduction in spleen size compared to baseline. Of the 10 patients who showed a measurable decrease in spleen size, 2 patients were from the group treated weekly with rhSAP (Cohort 2), 3 patients were from the group treated every 4 weeks with rhSAP (Cohort 1), 1 patient was from the group treated weekly with rhSAP in combination with ruxolitinib (Cohort 3) and 4 patients were from the group treated with every 4 weeks with rhSAP in combination with ruxolitinib (Cohort 4). Patients in Cohorts 3 and 4 were on a stable dose (e.g., on ruxolitinib for at least 3 months without any dose modifications) of ruxolitinib for at least 12 weeks prior to the study and had ceased to show improvement in spleen size in the last four weeks prior to the start of SAP therapy. Therefore, it should be noted that the responsive patients in Cohorts 3 and 4 (101-012, 103-001, 101-010, 101-002, and 103-004) had previously already achieved their maximal response on prior therapy (ruxolitinib) but nevertheless showed further improvement in symptoms upon treatment with SAP therapy used in combination with ruxolitinib. Indeed, patients 101-012, 103-001, and 101-010 experienced an improvement of ≥20% in spleen size on the combination therapy.

Figure 2:
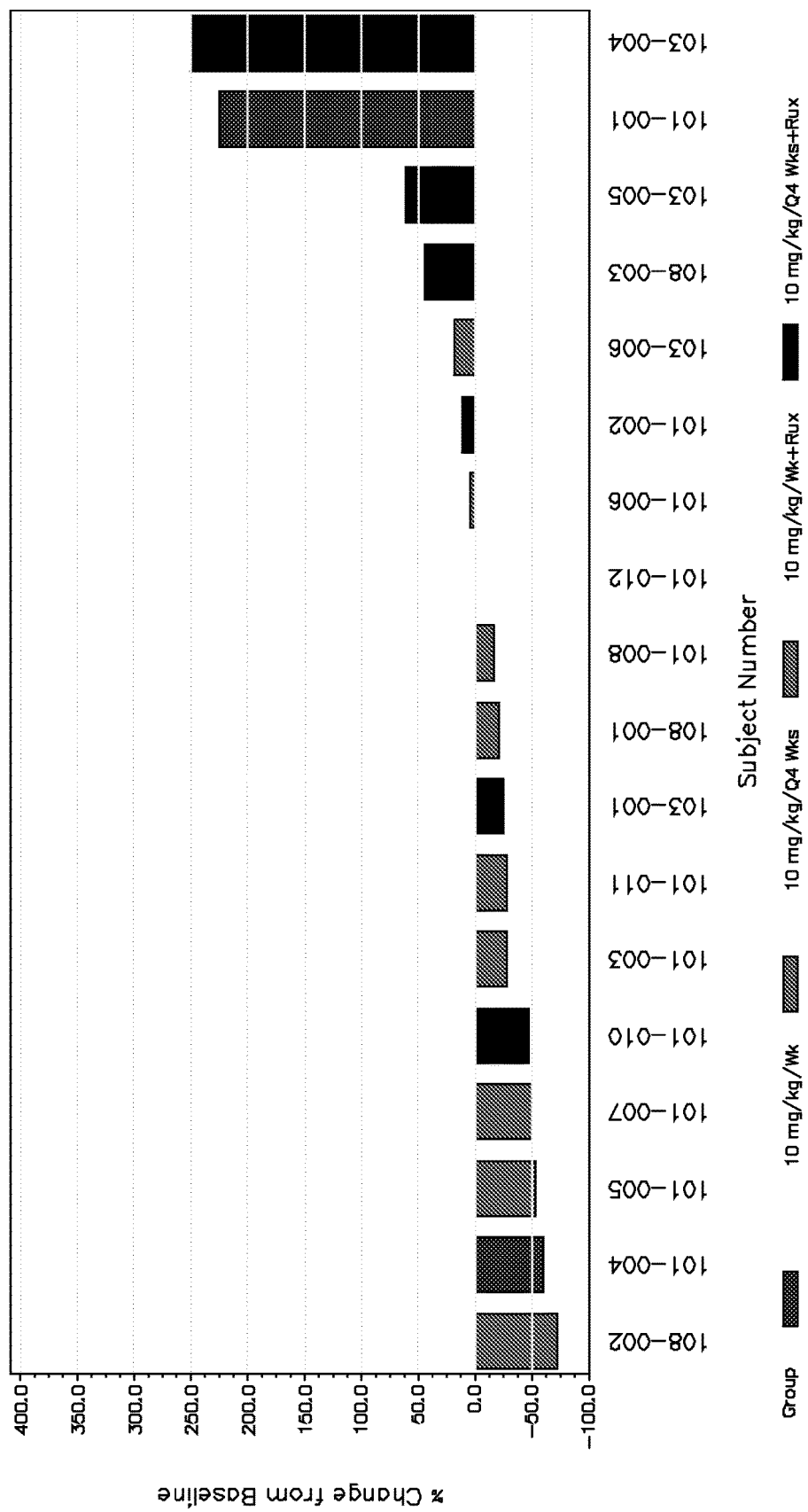
FIG. 2 is a waterfall plot depicting the percentage change in MPN-SAF Total Symptom Score (TSS) in subjects who were followed to C6D29 (Cycle 6, Day 29) or end of study. The Y-axis indicates the percentage change in MPN-SAF TSS from baseline. The evaluated subjects are shown on the X-axis. As is evident from FIG. 2, improvement in clinical assessment from baseline, even over this time period, was observed in at least one patient from each treatment group (e.g., mono- and combination therapy on two different dosing schedules).

FIG. 2 shows the percentage change in the MPN-SAF Total Symptom Score (TSS) in subjects who were followed to C6D29 (Cycle 6, Day 29), end of study, or beyond. A majority of the evaluated patients (10 out of 18 patients, from all four treatment arms) showed a reduction in TSS compared to baseline and a ≥50% reduction in the Total Symptom Score was observed for 5 of these patients on Cycle 6 Day 29. Two additional subjects had a 50% decrease in symptom score that lasted ≥8 weeks but was less than 50% on Cycle 6 Day 29. Of the 10 patients who showed a measurable symptom response, 1 patient was from the group treated weekly with rhSAP (Cohort 2), 4 patients were from the group treated every 4 weeks with rhSAP (Cohort 1), 3 patients were from the group treated weekly with rhSAP in combination with ruxolitinib (Cohort 3) and 2 patients were from the group treated every 4 weeks with rhSAP in combination with ruxolitinib (Cohort 4). As mentioned above, the responsive patients in Cohorts 3 and 4 (108-002, 101-011, 108-001, 101-010, and 103-001) had previously already achieved their maximal response on prior therapy (ruxolitinib) but nevertheless showed further improvement in symptoms upon treatment with SAP in addition to ruxolitinib. Indeed, patients 108-002 and 101-010, from Cohorts 3 and 4 respectively, were amongst the patients who showed an improvement of ≥50% in TSS.

Improvement in hemoglobin and platelet levels, decrease in red blood cell transfusions, and decrease in bone marrow fibrosis were also observed for a number of patients in all 4 treatment arms. A decrease in bone marrow fibrosis by ≥1 grade has been observed in 5 patients at 12 or 24 weeks or both.

Analysis of the results following 24 weeks indicates therapeutic efficacy of rhSAP, alone or in combination with another anti-cancer agent, with a very good safety profile. The results demonstrated biologic activity in myelofibrosis patients with improvements across clinically relevant measures including bone marrow fibrosis, hemoglobin, platelets, symptoms, and spleen volume on both weekly and every 4 week dosing schedules. Despite the severity of the disease in the evaluated patients, positive responses were observed in all 4 treatment arms, even at this early stage of the study and even when using high thresholds for evaluating confirmed responses. Treatment with rhSAP was safe and well tolerated alone and in combination with ruxolitinib, with no evidence of clinically significant myelosuppression induced or as a result of SAP therapy, as commonly observed with other treatments (e.g., treatment-related myelosuppression). The response rate seen was consistent with the efficacy seen with other cancer therapeutics. Improvements were seen in patients who had either progressed after treatment with one or more prior JAK inhibitors or were deriving no further benefit from a stable dose of ruxolitinib. Reversal of fibrosis pathology in patients receiving SAP validates the central mechanism of this protein and supports the use of SAP agonists across other fibrotic cancers.

Furthermore, 3 bone marrow responses were observed in 10 additional patients evaluated at 36 weeks of rhSAP therapy, and patients identified as responsive to therapy at the 12- or 24-week mark continued to respond following 36 weeks of treatment. This provides additional validation that prolonged rhSAP therapy, alone, or in combination with another anti-cancer agent, produces a durable response (e.g., continues to confer beneficial effects). Moreover, the longer patients are treated and observed, the more positive responses are identified; indicative of an even higher response rate than estimated based on observations following 24 weeks of treatment.

Example 3

Representative Individual Patient Data

A representative example of response data from one responsive patient is shown here. The hemoglobin, platelet, MPN-SAF TSS, and spleen response trends to treatment with rhSAP over the course of 24 weeks for patient 101-005 are shown in FIGS. 3A-D. Patient 101-005 was treated with SAP every 4 weeks (Cohort 1). Patient characteristics are summarized in Table 4 below.

TABLE 4

| Type | DIPSS risk group | Years since initial diagnosis | # prior therapies |
|---|---|---|---|
| PMF | Intermediate-2 | 7 | 3 |

Figure 3:
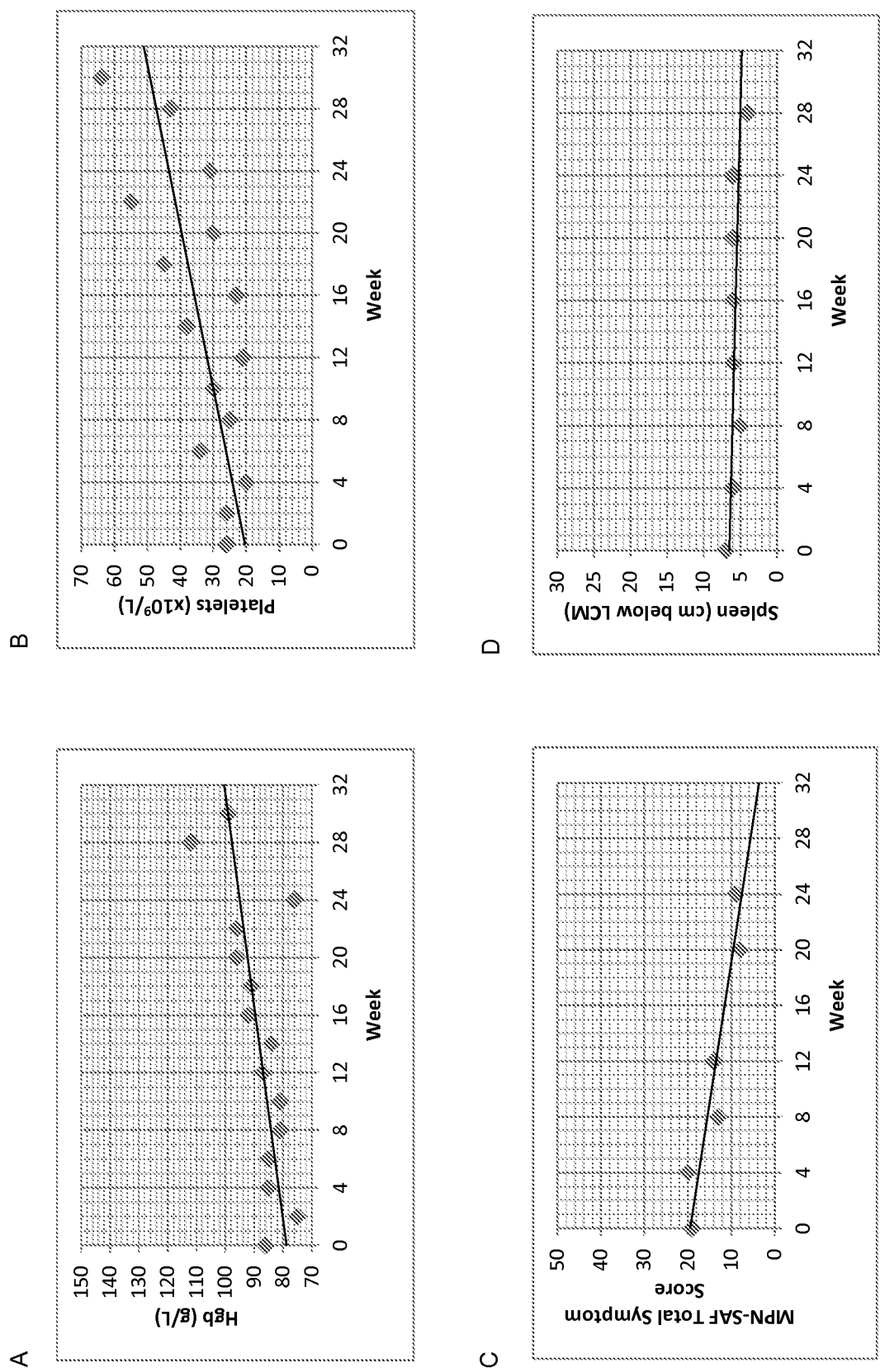
FIG. 3 shows scatter graphs with trend lines depicting (A) hemoglobin response, (B) platelet response, (C) MPN-SAF Total Symptom Score (TSS) response, and (D) spleen size response in patient 101-005 over the course of 24-30 weeks of treatment with PRM-151 as a monotherapy. Over the course of treatment, this patient experienced increase in hemoglobin and platelets and a decrease in MPN-SAF TSS score and spleen size, as assessed over the indicated period.
Figure 4:
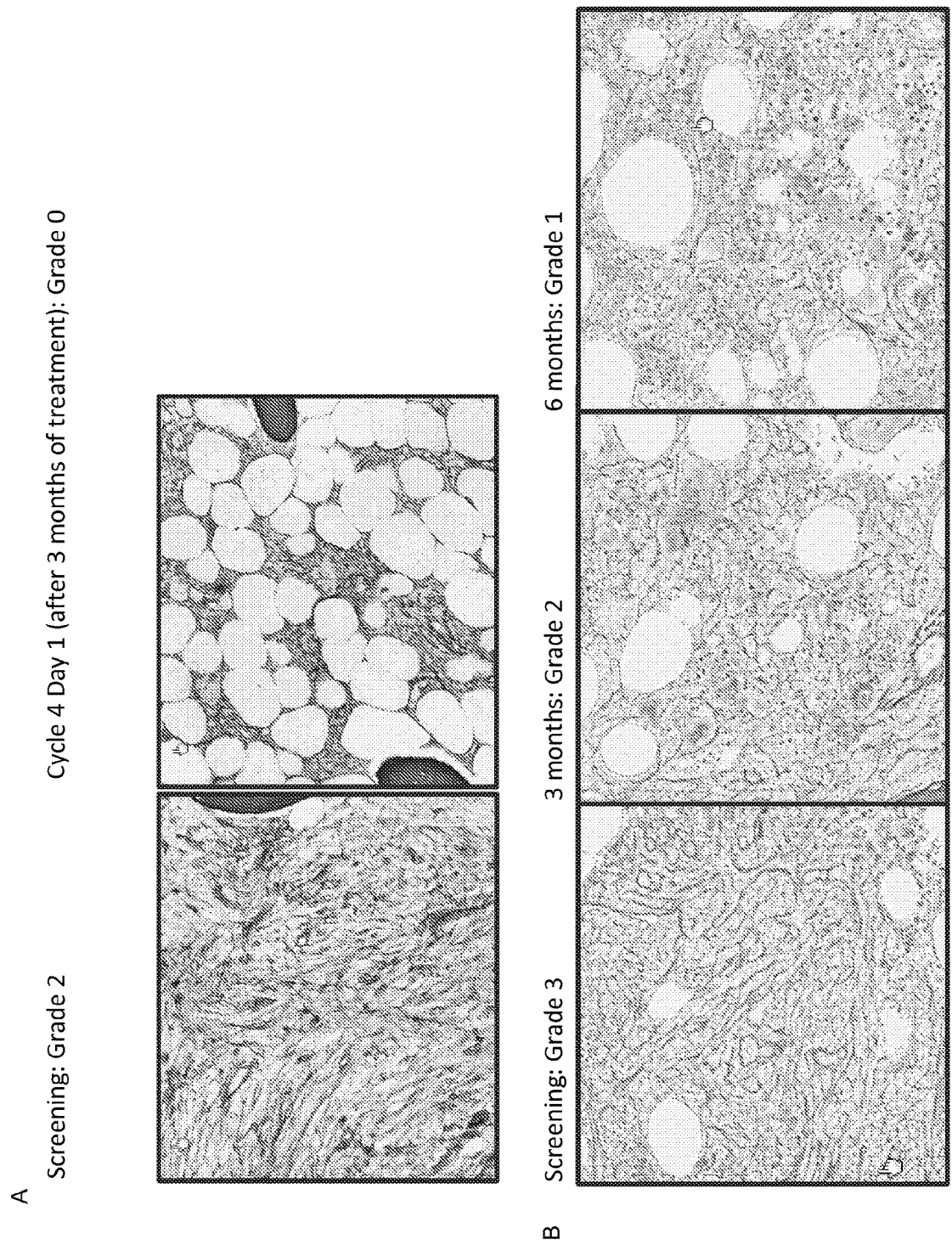
FIG. 4A shows reticulin staining of bone marrow biopsies from patient 101-005 at baseline (left panel of 4A) and after three months of treatment with PRM-151 as a monotherapy (right panel of 4A). Over the course of treatment, this patient experienced a decrease in bone marrow fibrosis from Grade 2 to Grade 0, as assessed at these two time points.
FIG. 4B shows reticulin staining of bone marrow biopsies from patient 108-003 at baseline (left panel of 4B), after three months of treatment with PRM-151 (center panel of 4B), and after 6 months of treatment with PRM-151 (right panel of 4B). Over the course of treatment, this patient experienced a decrease in bone marrow fibrosis from Grade 3 to Grade 2 and then from Grade 2 to Grade 1, as assessed at these three time points.

As seen in FIG. 3, patient 101-005 showed an improvement in hemoglobin and platelet levels, a reduction in MPN-SAF TSS and a reduction in spleen size over the course of treatment. In addition, patient 101-005 showed a decrease in bone marrow fibrosis from Grade 2 to Grade 0 at 12 weeks (FIG. 4).

Example 4

Representative Bone Marrow Fibrosis Data

A decrease in bone marrow fibrosis by ≥1 grade was observed in 5 patients. Representative reticulin staining data from patients 101-005 and 108-003 are shown in FIGS. 4A and 4B, respectively. Patients 101-005 and 108-003 were part of Cohorts 1 and 4, respectively. Bone marrow biopsies were obtained at baseline and after three and six months of therapy. The results of reticulin staining to evaluate bone marrow fibrosis in Patient 101-005 at baseline and after three months of treatment are shown in FIG. 4A. As seen in FIG. 4A, a decrease in bone marrow fibrosis from Grade 2 to Grade 0 at three months was observed in patient 101-005. The results of reticulin staining to evaluate bone marrow fibrosis in Patient 108-003 at baseline, after three months of treatment, and after six months of treatment are shown in FIG. 4B. As seen in FIG. 4B, a decrease in bone marrow fibrosis from Grade 3 to Grade 2 at three months and a further decrease from Grade 2 to Grade 1 at six months were observed in patient 108-003. Fibrosis is the formation of excess fibrous connective tissue in an organ or tissue in a reparative or reactive process. The primary component of fibrosis is collagen. Collagen appears as pink, amorphous tissue in standard hematoxylin and eosin pathology. Reticulin staining shows the fibers of Type 3 collagen as black strands and is used to by pathologists to identify the presence of fibrosis in all organs. Reticulin staining is a core element of the grading of bone marrow fibrosis (Thiele et al, Hematologica 2005; 90: 1128-1132.) Some reticulin staining is present in normal bone marrow, particularly in blood vessel walls.

The observed reversal of (e.g., decreasing of) bone marrow fibrosis is indicative of restoration and/or improvement of organ function, in this case of bone marrow function. Restoration of bone marrow function is further evidenced by improvement in the complete blood counts (CBC) of this and other patients.

Example 5

Treatment of Myelofibrosis with Recombinant Human Sap (Rhsap) and Ruxolitinib Conjoint Therapy Patients diagnosed as having myelofibrosis, including PMF, post-PV MF, or post ET-MF and who have been on a stable dose of ruxolitinib for at least three months with no improvement in spleen receive human, α2,3-sialic-containing SAP recombinantly expressed in CHO cells (rhSAP expressed in CHO cells; SAP comprising at least one α2,3 linkage and differing in glycosylation from SAP derived from human serum) in combination with ruxolitinib. Efficacy will be assessed by evaluation of the overall response rate (ORR) categorized according to the International Working Group (IWG) Criteria modified to include stable disease with improvement in bone marrow fibrosis by at least one grade as a response. Subjects responding to therapy will continue receiving it as long as there is a benefit.

Example 6

Treatment of Myelofibrosis with Recombinant Human Sap (Rhsap)

Patients diagnosed as having myelofibrosis, including PMF, post-PV MF, or post ET-MF receive human, α2,3-sialic-containing SAP recombinantly expressed in CHO cells (rhSAP expressed in CHO cells; SAP comprising at least one α2,3 linkage and differing in glycosylation from SAP derived from human serum). Efficacy will be assessed by evaluation of the overall response rate (ORR) categorized according to the International Working Group (IWG) Criteria modified to include stable disease with improvement in bone marrow fibrosis by at least one grade as a response. Subjects responding to therapy will continue receiving it as long as there is a benefit.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will be apparent to those skilled in the art upon review of this specification and the below-listed claims. The full scope of the invention should be determined by reference to the claims, along with their full scope of equivalents, and the specification, along with such variations.

SEQUENCE LISTING human serum amyloid protein P
SEQ ID NO: 1
HTDLSGKVFVFPRESVTDHVNLITPLEKPLQNFTLCFRAYSDLSRAYSLF
SYNTQGRDNELLVYKERVGEYSLYIGRHKVTSKVIEKFPAPVHICVSWES
SSGIAEFWINGTPLVKKGLRQGYFVEAQPKIVLGQEQDSYGGKFDRSQSF
VGEIGDLYMWDSVLPPENILSAYQGTPLPANILDWQALNYEIRGYVIIKP
LVWV Gallus gallus serum amyloid protein P
SEQ ID NO: 2
QEDLYRKVFVFREDPSDAYVLLQVQLERPLLNFTVCLRSYTDLTRPHSLF
SYATKAQDNEILLFKPKPGEYRFYVGGKYVTFRVPENRGEWEHVCASWES
GSGIAEFWLNGRPWPRKGLQKGYEVGNEAVVMLGQEQDAYGGGFDVYNSF
TGEMADVHLWDAGLSPDKMRSAYLALRLPPAPLAWGRLRYEAKGDVVVKP
RLREALGA Bos taurus serum amyloid protein P
SEQ ID NO: 3
QTDLRGKVFVFPRESSTDHVTLITKLEKPLKNLTLCLRAYSDLSRGYSLF
SYNIHSKDNELLVFKNGIGEYSLYIGKTKVTVRATEKFPSPVHICTSWES
STGIAEFWINGKPLVKRGLKQGYAVGAHPKIVLGQEQDSYGGGFDKNQSF
MGEIGDLYMWDSVLSPEEILLVYQGSSSISPTILDWQALKYEIKGYVIVK
PMVWG Cricetulus migratorius serum amyloid protein P
SEQ ID NO: 4
QTDLTGKVFVFPRESESDYVKLIPRLEKPLENFTLCFRTYTDLSRPHSLF
SYNTKNKDNELLIYKERMGEYGLYIENVGAIVRGVEEFASPVHFCTSWES -continued SSGIADFWVNGIPWVKKGLKKGYTVKTQPSIILGQEQDNYGGGFDKSQSF
VGEMGDLNMWDSVLTPEEIKSVYEGSWLEPNILDWRALNYEMSGYAVIRP
RVWH

We claim:

1. A method for treating a fibrotic cancer or improving the efficacy of an anti-cancer therapeutic in a patient having fibrotic cancer, comprising administering to said patient a therapeutically effective amount of a serum amyloid P (SAP) agonist, wherein the SAP agonist is an SAP polypeptide that binds to Fcγ receptors and provides an inhibitory signal to fibrocytes and fibrocyte precursors in vitro, wherein the SAP agonist is administered one or more times in an initial loading dose during a first week of administration followed by one time every one to four weeks, wherein each administration of the SAP agonist is 0.1-40 mg/kg, wherein the fibrotic cancer is not pancreatic cancer, and wherein either
   (i) the efficacy of a Jak kinase inhibitor has decreased in the patient prior to initiation of treatment with the SAP agonist, or
   (ii) the patient or the cancer is, prior to initiation of treatment with the SAP agonist, unresponsive to, resistant to, or refractory to treatment with a JAK kinase inhibitor.

2. The method of claim 1, wherein the SAP agonist is a glycosylated human SAP polypeptide comprising an N-linked oligosaccharide chain, wherein at least one branch of the oligosaccharide chain terminates with a α2,3-linked sialic acid moiety.

3. The method of claim 2, wherein all branches of the oligosaccharide chain terminate with α2,3-linked sialic acid moieties.

4. The method of claim 2, wherein the oligosaccharide chain is substantially free of α2,6-linked sialic acid moieties.

5. The method of claim 1, wherein the polypeptide comprises an amino acid sequence at least 95% identical to SEQ ID NO: 1.

6. The method of claim 1, wherein the polypeptide is a fusion protein comprising an SAP domain and one or more heterologous domains, wherein the one or more heterologous domains enhance one or more of in vivo stability, in vivo half-life, uptake/administration, tissue localization or distribution, formation of protein complexes, and/or purification.

7. The method of claim 1, wherein the polypeptide comprises one or more modified amino acid residues.

8. The method of claim 7, wherein the one or more modified amino acid residues comprise a PEGylated amino acid, a prenylated amino acid, an acetylated amino acid, a biotinylated amino acid, and/or an amino acid conjugated to an organic derivatizing agent.

9. The method of claim 1, wherein the method further comprises administering to the patient the anti-cancer therapeutic.

10. The method of claim 9, wherein the anti-cancer therapeutic is selected from: chemotherapy agents, antibody-based agents, tyrosine kinase inhibitors, immunomodulatory agents, biologic agents, and combinations thereof.

11. The method of claim 10, wherein the chemotherapy agent is selected from: actinomycin D, aldesleukin, alitretinoin, all-trans retinoic acid/ATRA, altretamine, amascrine, asparaginase, azacitidine, azathioprine, *bacillus* calmette-guerin/BCG, bendamustine hydrochloride, bexarotene, bicalutamide, bleomycin, bortezomib, busulfan, capecitabine, carboplatin, carfilzomib, carmustine, chlorambucil, cisplatin/cisplatinum, cladribine, cyclophosphamide/cytophosphane, cytabarine, dacarbazine, daunorubicin/daunomycin, denileukin diftitox, dexrazoxane, docetaxel, doxorubicin, epirubicin, etoposide, fludarabine, fluorouracil (5-FU), gemcitabine, goserelin, hydrocortisone, hydroxyurea, idarubicin, ifosfamide, interferon alfa, irinotecan CPT-11, lapatinib, lenalidomide, leuprolide, mechlorethamine/chlormethine/mustine/HN2, mercaptopurine, methotrexate, methylprednisolone, mitomycin, mitotane, mitoxantrone, octreotide, oprelvekin, oxaliplatin, paclitaxel, pamidronate, pegaspargase, pegfilgrastim, PEG interferon, pemetrexed, pentostatin, phenylalanine mustard, plicamycin/mithramycin, prednisone, prednisolone, procarbazine, raloxifene, romiplostim, sargramostim, streptozocin, tamoxifen, temozolomide, temsirolimus, teniposide, thalidomide, thioguanine, thiophosphoamide/thiotepa, thiotepa, topotecan hydrochloride, toremifene, tretinoin, valrubicin, vinblastine, vincristine, vindesine, vinorelbine, vorinostat, zoledronic acid, and combinations thereof;
  wherein the antibody-based agent is selected from: alemtuzumab, bevacizumab, cetuximab, fresolimumab, gemtuzumab ozogamicin, ibritumomab tiuxetan, ipilimumab, ofatumumab, panitumumab, rituximab, tositumomab, trastuzumab, trastuzumab DM1, and combinations thereof;
  wherein tyrosine kinase inhibitor is selected from: axitinib, bafetinib, bosutinib, cediranib, crizotinib, dasatinib, erlotinib, gefitinib, imatinib, lapatinib, neratinib, nilotinib, pazopanib, ponatinib, quizartinib, regorafenib, sorafenib, sunitinib, vandetanib, vatalanib, and combinations thereof;
  wherein the immunomodulatory agent is selected from: thalidomide, lenalidomide, pomalidomide, methotrexate, leflunomide, cyclophosphamide, cyclosporine A, minocycline, azathioprine, tacrolimus, methylprednisolone, mycophenolate mofetil, rapamycin, mizoribine, deoxyspergualin, brequinar, 5,6-dimethylxanthenone-4-acetic acid (DMXAA), lactoferrin, poly AU, polyI:polyC 12U, poly-ICLC, imiquimod, resiquimod, unmethylated CpG dinucleotide (CpG-ODN), and ipilumumab; or
  wherein the biologic agent is selected from: IL-2, IL-3, erythropoietin, G-CSF, filgrastim, interferon alfa, bortezomib and combinations thereof.

12. The method of claim 10, wherein the tyrosine kinase inhibitor is a Janus kinase inhibitor selected from: AC-430, AZD1480, baricitinib, BMS-911453, CEP-33779, CYT387, GLPG-0634, INCB18424, lestaurtinib, LY2784544, NS-018, pacritinib, ruxolitinib, TG101348 (SAR302503), tofacitinib, VX-509, R-348, R723 and combinations thereof.

13. The method of claim 9, wherein the anti-cancer therapeutic is selected from: AB0024, AZD1480, AT-9283, BMS-911543, CYT387, everolimus, givinostat, imetelstat, lestaurtinib, LY2784544, NS-018, oral arsenic, pacritinib, panobinostat, peginterferon alfa-2a, pomalidomide, pracinostat, ruxolitinib, TAK-901, and TG101438 (SAR302503).

14. The method of claim 9, wherein the anti-cancer therapeutic is ruxolitinib.

15. The method of claim 1, wherein the cancer is myelofibrosis.

16. The method of claim 15, wherein the myelofibrosis is primary myelofibrosis, post-polycythemia vera myelofibrosis, or post-essential thrombocythemia myelofibrosis.

17. The method of claim 15, wherein the SAP agonist, alone or in combination with the anti-cancer therapeutic, is administered according to a dosage regimen effective to reduce spleen volume by at least 25% relative to baseline.

18. The method of claim 15, wherein the SAP agonist, alone or in combination with the anti-cancer therapeutic, is administered according to a dosage regimen effective to increase hemoglobin levels by at least 1 g/L relative to baseline.

19. The method of claim 15, wherein the SAP agonist, alone or in combination with the anti-cancer therapeutic, is administered according to a dosage regimen effective to reduce red blood cell (RBC) transfusions by at least 25% relative to baseline.

20. The method of claim 15, wherein the SAP agonist, alone or in combination with the anti-cancer therapeutic, is administered according to a dosage regimen effective to reduce platelet transfusions by at least 25%.

21. The method of claim 15, wherein the method comprises administering the SAP agonist and the anti-cancer therapeutic according to a dosage regimen such that one or more side effects are reduced relative to treatment with the anti-cancer therapeutic alone.

22. The method of claim 15, wherein administration of the SAP agonist does not result in or induce treatment related myelosuppression.

23. The method of claim 1, wherein the patient or the cancer is, prior to initiation of treatment with the SAP agonist, unresponsive to, resistant to, or refractory to chemotherapy.

24. A method for treating a fibrotic cancer or improving the efficacy of an anti-cancer therapeutic in a patient having fibrotic cancer, comprising administering to said patient a therapeutically effective amount of one or more SAP agonists in combination with one or more additional active agents, wherein the one or more SAP agonists are SAP polypeptides that bind to Fcγ receptors and provide an inhibitory signal to fibrocytes and fibrocyte precursors in vitro, wherein the fibrotic cancer is not pancreatic cancer, and wherein either
  (i) the efficacy of a Jak kinase inhibitor has decreased in the patient prior to initiation of treatment with the one or more SAP agonists, or
  (ii) the patient or the cancer is, prior to initiation of treatment with the one or more SAP agonists, unresponsive to, resistant to, or refractory to treatment with a JAK kinase inhibitor.

25. The method of claim 24, wherein all sialylated branches of the oligosaccharide chain terminate with α2,3-linked sialic acid moieties wherein the oligosaccharide chain is substantially free of α2,6-linked sialic acid moieties, and wherein the SAP polypeptides comprise the amino acid sequence of SEQ ID NO:1.

26. The method of claim 24, wherein the one or more SAP agonists include is-a glycosylated human SAP polypeptide comprising an N-linked oligosaccharide chain, wherein all the sialylated branches of the oligosaccharide chain terminate with α2,3-linked sialic acid moieties, wherein the N-linked oligosaccharide chain is free of α2,6-linked sialic acid moieties, and wherein the glycosylated human SAP polypeptide comprises the amino acid sequence of SEQ ID NO:1 .

27. A method for treating a fibrotic cancer, comprising administering to a patient in need thereof a therapeutically effective amount of an SAP agonist, wherein the SAP agonist is an SAP polypeptide which binds to Fcγ receptors and provides an inhibitory signal to fibrocytes and fibrocyte precursors in vitro, wherein the SAP agonist is administered one or more times in an initial loading dose during a first week of administration followed by one time every one to four weeks, wherein each administration of the SAP agonist is 0.1-40 mg/kg, wherein the fibrotic cancer is not pancreatic cancer, and wherein either
- (i) the efficacy of a Jak kinase inhibitor has decreased in the patient prior to initiation of treatment with the SAP agonist, or
- (ii) the patient or the cancer is, prior to initiation of treatment with the SAP agonist, unresponsive to, resistant to, or refractory to treatment with a JAK kinase inhibitor.

28. The method of claim 27, wherein the fibrotic cancer is myelofibrosis.

29. The method of claim 27, wherein the Jak kinase inhibitor is ruxolitinib.

30. The method of claim 27, wherein the SAP polypeptide comprises an amino acid sequence that is at least 95% identical to SEQ ID NO:1.

31. The method of claim 27, wherein the SAP polypeptide comprises an amino acid sequence that is at least 96% identical to SEQ ID NO:1.

32. The method of claim 27, wherein the SAP polypeptide comprises an amino acid sequence that is at least 97% identical to SEQ ID NO:1.

33. The method of claim 27, wherein the SAP polypeptide comprises an amino acid sequence that is at least 98% identical to SEQ ID NO:1.

34. The method of claim 27, wherein the SAP polypeptide comprises an amino acid sequence that is at least 99% identical to SEQ ID NO:1.

35. The method of claim 27, wherein the SAP polypeptide comprises the amino acid sequence of SEQ ID NO:1.

36. The method of claim 27, wherein the SAP agonist is a glycosylated human SAP polypeptide comprising an N-linked oligosaccharide chain, wherein at least one branch of the oligosaccharide chain terminates with a α2,3-linked sialic acid moiety.

37. The method of claim 36, wherein all branches of the oligosaccharide chain terminate with α2,3-linked sialic acid moieties.

38. The method of claim 36, wherein the oligosaccharide chain is substantially free of α2,6-linked sialic acid moieties.

39. The method of claim 35, wherein the SAP agonist is a glycosylated human SAP polypeptide comprising an N-linked oligosaccharide chain, wherein at least one branch of the oligosaccharide chain terminates with a α2,3-linked sialic acid moiety.

40. The method of claim 39, wherein all branches of the oligosaccharide chain terminate with α2,3-linked sialic acid moieties.

41. The method of claim 39, wherein the oligosaccharide chain is substantially free of α2,6-linked sialic acid moieties.

42. A method for treating a fibrotic cancer, comprising administering to a patient in need thereof a therapeutically effective amount of an SAP agonist, wherein the SAP agonist an SAP polypeptide comprising SEQ ID NO:1, wherein the SAP agonist is administered one or more times in an initial loading dose during a first week of administration followed by one time every one to four weeks, wherein each administration of the SAP agonist is 0.1-40 mg/kg, wherein the fibrotic cancer is myelofibrosis, and wherein either
- (i) the efficacy of ruxolitinib has decreased in the patient prior to initiation of treatment with the SAP agonist, or
- (ii) the patient or the cancer is, prior to initiation of treatment with the SAP agonist, unresponsive to, resistant to, or refractory to treatment with ruxolitinib.

43. The method of claim 42, wherein the SAP polypeptide comprises an N-linked oligosaccharide chain, wherein at least one branch of the oligosaccharide chain terminates with a α2,3-linked sialic acid moiety.

44. The method of claim 43, wherein all branches of the oligosaccharide chain terminate with α2,3-linked sialic acid moieties.

45. The method of claim 43, wherein the oligosaccharide chain is substantially free of α2,6-linked sialic acid moieties.

* * * * *